(12) United States Patent
Ricciardi et al.

(10) Patent No.: US 9,233,921 B2
(45) Date of Patent: Jan. 12, 2016

(54) POTENT POXVIRUS INHIBITOR

(71) Applicant: The Trustees of the University of Pennsylvania, Philadelphia, PA (US)

(72) Inventors: Robert P. Ricciardi, East Marlborough, PA (US); Manunya Nuth, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 14/202,078

(22) Filed: Mar. 10, 2014

(65) Prior Publication Data

US 2014/0343114 A1    Nov. 20, 2014

Related U.S. Application Data

(60) Provisional application No. 61/774,781, filed on Mar. 8, 2013.

(51) Int. Cl.
*C07D 209/12* (2006.01)
*C07D 209/30* (2006.01)
*C07D 209/42* (2006.01)

(52) U.S. Cl.
CPC ............ *C07D 209/30* (2013.01); *C07D 209/12* (2013.01); *C07D 209/42* (2013.01)

(58) Field of Classification Search
CPC ..................................................... C07D 209/12
USPC .......................................... 548/484; 514/418
See application file for complete search history.

(56) References Cited

U.S. PATENT DOCUMENTS

| 5,527,819 | A | 6/1996 | Williams et al. |
| 2002/0068014 | A1 | 6/2002 | Haught et al. |
| 2006/0052418 | A1 | 3/2006 | Beaulieu et al. |
| 2007/0021442 | A1 | 1/2007 | Saggar et al. |

OTHER PUBLICATIONS

Poxviruses [online] retrieved from the internet on Jan. 12, 2015; last updated Sep. 30, 2013; URL;http://emedicine.medscape.com/article/226239-overview.*
Poxviruses treatment & Management [online] retrieved from the internet on Jan. 12, 2015; last updated Sep. 30, 2013; URL; http://emedicine.medscape.com/article/226239-treatment.*
Abad-Zapatero et al. "Ligand efficiency indices as guideposts for drug discovery", Drug Discov. Today 2005, 10, 464-469.
Abagyan et al. "Icm—a New Method for Protein Modeling and Design—Applications to Docking and Structure Prediction from the Distorted Native Conformation", J Comput Chem 1994, 15, 488-506.
Abuchowski et al. "Alteration of the circulating life and antigenic properties of bovine deaminase in mice by attachment of polyethylene glycol", Clin Exp Immunol. Dec. 1981;46(3):649-52.

Agulnick et al. "Identification of a DNA-binding protein of human herpesvirus 6, a putative DNA polymerase stimulatory factor", J. Gen. Virol. 1993, 74 ( Pt 6), 1003-1009.
Berge et al. "Pharmaceutical salts", Journal of Pharmaceutical Science, 66, 1-19 (1977).
Bisht, et al. "Vaccinia virus L1 protein is required for cell entry and membrane fusion", J. Virol. 2008, 82, 8687-8694.
Blasco et al. "Extracellular Vaccinia Virus Formation and Cell-to-Cell Virus Transmission Are Prevented by Deletion of the Gene Encoding the 37,000-Dalton Outer Envelope Protein", J. Virol. 1991, 65, 5910-5920.
Bonneau et al. "De novo prediction of three-dimensional structures for major protein families", J. Mol. Biol. 2002, 322, 65-78.
Bonneau et al. "Improving the performance of Rosetta using multiple sequence alignment information and global measures of hydrophobic core formation", Proteins 2001, 43, 1-11.
Boyle et al. "Evaluation of the role of the vaccinia virus uracil DNA glycosylase and A20 proteins as intrinsic components of the DNA polymerase holoenzyme", J. Biol. Chem. 2011, 286, 24702-24713.
Brenke et al. "Fragment-based identification of druggable 'hot spots' of proteins using Fourier domain correlation techniques", Bioinformatics 2009, 25, 621-627.
Buchwald et al., "Long-term, continuous heparin administration by an implantable infusion pump in ambulatory patients with recurrent venous thrombosis", Surgery, 88 (1980), pp. 507-516.
Chang et al. "The E3I Gene of Vaccinia Virus Encodes an Inhibitor of the Interferon-Induced, Double-Stranded Rna-Dependent Protein-Kinase", Proc. Natl. Acad. Sci. U.S.A. 1992, 89, 4825-4829.
Ciustea et al. "Identification of nonnucleoside DNA synthesis inhibitors of vaccinia virus by high-throughput screening", J. Med. Chem. 2008, 51, 6563-6570.
Druck Shudofsky et al. "Vaccinia Virus D4 Mutants Defective in Processive DNA Synthesis Retain Binding to A20 and DNA", J. Virol. 2010, 84, 12325-12335.
Duraffour et al. "Activity of the anti-orthopoxvirus compound ST-246 p. 46 of 48 ACS Paragon Plus Environment Journal of Medicinal Chemistry against vaccinia, cowpox and camelpox viruses in cell monolayers and organotypic raft cultures", Antivir. Ther. (Lond.) 2007, 12, 1205-1216.
Ellison et al. "Opening of the clamp: an intimate view of an ATP-driven biological machine", Cell 2001, 106, 655-660.
Goodson, in Medical Applications of Controlled Release, supra, vol. 2, pp. 115-138 (1984).
Gottlieb et al. "The herpes simplex virus type 1 UL42 gene product: a subunit of DNA polymerase that functions to increase processivity", J. Virol. 1990, 64, 5976-5987.
Ishii et al. "Mapping interaction sites of the A2OR protein component of the vaccinia virus DNA replication complex", Virology 2002, 303, 232-239.
Katre et al. "Chemical modification of recombinant interleukin 2 by polyethylene glycol increases its potency in the murine Meth A sarcoma model", Proc. Natl. Acad. Sci. USA, vol. 84, pp. 1487-1491, Mar. 1987.

(Continued)

*Primary Examiner* — Shawquia Jackson
(74) *Attorney, Agent, or Firm* — Mark S. Cohen; Pearl Cohen Zedek Latzer Baratz LLP

(57) ABSTRACT

This invention provides compounds of formulas (I), (II), (III), and (IV) as defined in the specification, and pharmaceutical compositions comprising the same, and methods of inhibiting, treating, or abrogating a poxvirus infection in a subject using the compounds or compositions.

35 Claims, 8 Drawing Sheets

(56) References Cited

OTHER PUBLICATIONS

Kiehl et al. "Cooperation of EBV DNA polymerase and EA-D(BMRF1) in vitro and colocalization in nuclei of infected cells", Virology 1991, 184, 330-340.

Klemperer et al. "The A2OR protein is a stoichiometric component of the processive form of vaccinia virus DNA polymerase", J. Virol. 2001, 75, 12298-12307.

Kong et al. "Three-dimensional structure of the beta subunit of E. coli DNA polymerase III holoenzyme: a sliding DNA clamp", Cell 1992, 69, 425-437.

Krishna et al. "Crystal structure of the eukaryotic DNA polymerase processivity factor PCNA", Cell 1994, 79, 1233-1243.

Langer "New methods of drug delivery", Science, 249 (1990), pp. 1527-1533.

Lin et al. "The 41-kDa protein of human herpesvirus 6 specifically binds to viral DNA polymerase and greatly increases DNA synthesis", Virology 1998, 250, 210-219.

Lin et al. "Cloning and functional analysis of Kaposi's sarcomaassociated herpesvirus DNA polymerase and its processivity factor", J. Virol. 1998, 72, 6228-6232.

Longini et al. "Containing a large bioterrorist smallpox attack: a computer simulation approach", Int. J. Infec. Dis. 2007, 11, 98-108.

Lopez-Berestein, in Liposomes in the Therapy of Infectious Disease and Cancer, Lopez- Berestein and Fidler (eds.), Liss, New York, pp. 317-327 (1989).

Maa et al. "Structural and Functional-Studies of a 39,000-Mr-Immunodominant Protein of Vaccinia Virus", J. Virol. 1987, 61, 3910-3919.

Mirocha et al. "Fungus metabolites toxic to animals", Annual review of phytopathology, 1974, vol. 12, pp. 303-330.

Newmark et al. "Tuberous sclerosis evaluated by computerized tomography", vol. 6, Issue 5, Sep.-Oct. 1982, pp. 287-293.

Nuth et al. "R. P. Identification of inhibitors that block vaccinia virus infection by targeting the DNA synthesis processivity factor D4", J. Med. Chem. 2011, 54, 3260- 3267. Page 44 of 48 ACS Paragon Plus Environment Journal of Medicinal Chemistry.

Okazaki et al. "Antiviral activity of macrocyclic trichothecene mycotoxins and related compounds baccharinoids B-4 and B-5 against Herpes", Agric. Biol. Chem., 1989, vol. 53 (5), pp. 1141-1143.

Pettersen et al. "UCSF Chimera—a visualization system for exploratory research and analysis", J Comput Chem 2004, 25, 1605-1612.

Quenelle et al. "Cutaneous infections of mice with vaccinia or cowpox viruses and efficacy of cidofovir", Antiviral Res. 2004, 63, 33-40.

Quenelle et al. "Oral treatment of cowpox and vaccinia virus infections in mice with ether lipid esters of cidofovir", Antimicrob. Agents Chemother. 2004, 48, 404-412.

Ragno et al. "Docking and 3D-QSAR studies in indolyl aryl sulfones, binding mode exploration at the HIV reverse transcriptase non-nucleoside binding site and design of highly active N-(2-hydroxyethyl)carboxamide and N-(2- hydroxyethyl)carbohydrazide derivatives", J. Med. Chem. 2005, vol. 48, pp. 218-223.

Risco et al. "The vaccinia virus 39-kDa protein forms a stable complex with the p4a/4a major core protein early in morphogenesis" Virology 1999, 265, 375-386.

Saudek et al. "A Preliminary Trial of the Programmable Implantable Medication System for Insulin Delivery", N. Engl. J. Med. 321:574 (1989).

Schormann et al. "Crystal structure of vaccinia virus uracil-Dna glycosylase reveals dimeric assembly", BMC Struct. Biol. 2007, 7, 45.

Schormann et al. "Identification of protein-protein interaction inhibitors targeting vaccinia virus processivity factor for development of antiviral agents", Antimicrob. Agents Chemother. 2011, 55, 5054-5062.

Sefton "Implantable Pumps", CRC Press, Boca Raton, FL, ETATS-UNIS (1981) (Revue) 1987, vol. 14, No. 3, pp. 201-240.

Simons et al. "Improved recognition of native-like protein structures using a combination of sequence-dependent and sequence-independent features of proteins", Proteins 1999, 34, 82-95.

Smith et al. "In Vitro Efficacy of ST246 against Smallpox and Monkeypox. Antimicrob. Agents", Chemother. 2009, 53, 1007-1012.

Stanitsa et al. "Vaccinia virus uracil Dna glycosylase interacts with the A20 protein to form a heterodimeric processivity factor for the viral DNA polymerase", J. Biol. Chem. 2006, 281, 3439-3451.

Treat et al., in Liposomes in the Therapy of Infectious Disease and Cancer, Lopez-Berestein and Fidler (eds.), Liss, New York, pp. 353-365 (1989).

Tsurumi et al. "Functional interaction between Epstein-Barr virus DNA polymerase catalytic subunit and its accessory subunit in vitro", J. Virol. 1993, 67, 7648-7653.

Weiland et al. "Functional analysis of human cytomegalovirus polymerase accessory protein", Virus Res. 1994, 34, 191-206. Page 43 of 48 ACS Paragon Plus Environment Journal of Medicinal Chemistry.

Yang et al. "An orally bioavailable antipoxvirus compound (ST-246) inhibits extracellular virus formation and protects mice from lethal orthopoxvirus challenge", J. Virol. 2005, 79, 13139-13149.

\* cited by examiner

```
VACV        MTSSADLTNLEELLSLYRSIKPSDSAAIEKYNGLVEKGSTIWKIGVQKVANVETSISDYYDEVENKP
VARV (98%)  MTSSADLTNLEELLSLYRSLRTSDSAAIEKYNGLVEKGSTIWKIGVQKVANVETSISDYYDEVENKP
MPXV (97%)  MTSSADLTNLEELLSLYRSLRTSDSVAIEKYNGLVEKGSTIWKIGVQKNTWVETSISDYYDKVENKP
CPXV (99%)  MTSSADLTNLEELLSLYRSLRTSDSAAIEKYNGLVEKGSTIWKIGVQKVANVETSISDYYDEVENKP
MCV  (29%)  MSKEPDLTFLKELLRLQQQLARAEPADTTRKNALVDKARPEWHVKYRECGIQSELLVEFFEQHETRA

VACV        PNIDPGYYIPLEVYTGSVFIYSPGKNMVELGSGNSRQIPDDMQSVCQKVLDSDNGIDFLRFVLLNNKW
VARV        PNIDPGYYIPLEVYTGSVFIYSRGKNMVELGSGNSRQIPDDMQSVCQKVLDGDNGIDFLRFVLLNNKW
MPXV        PNIDPGYYIPLEVYTGSVFIYSRGKNMVELGSGNSRQIPDEIESACQKVLDSDNGIDFLRFVLLNNKW
CPXV        PNIDPGYYIPLEVYTGSVFIYSRGKNMVELGSGNSRQIPDDMQSACQKVLDSDNGIDFLRFVLLNNKW
MCV         PTLARSTYTRSALHRGTALLKAGRQ-LLELGSSAARGAREELRAPCRAMLARYADVEALRFCNFEERY

VACV        IMEDAISKYQSPVNIF-RLASEYGLNIPRYLETEIEDTLPDELYSIIERST---DDKFPKISISYI
VARV        IMEDAISKYQSPVNIF-RLASEYGLNIPRYLETEIEDTLPDELYSIIERST---DDNFPKISISYI
MPXV        IMEDAISKYQSPVNIF-RLASEYGLNIPRYLETEIEDTLPDELYSIIMERST---DDTFPKISISYI
CPXV        IMEDAISKYQSPVNIF-RLASEYGLNIPRYLETEIEDTLPDELYSIIERST---DDKFPKISISYI
MCV         VLRQVHARARPAPHVWLPLAAAERSVAQHTRVEVRPESEKYFGVLVRYLRARQAALHVEAVCCV

VACV        KLSELPRQVVDFKPSFRYIESIKVDRIGDNIFIPSVIPSSGKRILVKDVDHLIRSKVASHTVKVRP
VARV        KLSELPRQVVDFKPSFRYIESIKVDRIGDNIFIPSVIPSSGKRILVKDVDHLIRSKVASHTVKVRP
MPXV        KLSELPRQVVDFKPFLPRYIESIKVDRIGDNIFIPSVIPSSGKRILVKDVDHLIRSKVASHTVKVRP
CPXV        KLSELPRQVVDFKPSFRYIESIKVDRIGDNIFIPSVIPSSGKRILVKDVDHLIRSKVASHTVKVRP
MCV         RDKRAERWRIAEGRPVYSCVDRLELEQVRPKRLRCLIRFARDRVLARDLEHLVQAHVRVGAKIVMRR

VACV        KNFPSILYDYDKSGTETRGEVIKRTIDTIGRDYVNGKYFSKVGSAGLRQLTNELDTR-ECAYVDELV
VARV        KNFPSILYDYDKSGTETRGEVIKRTIDTIGRDYVNGKYFSKVGSAGLRQLTNELDTR-RCTTVDELV
MPXV        KNFPSILYDYDKSGTETRGEVIKRTIDTIGRDYVNGKYFSKVGSAGLRQLTNELDTR-RCAYVDELV
CPXV        KNFPSILYDYDKSGTETRGEVIKRTIDTIGRDYVNGKYFSKVGSAGLRQLTNELDTR-RCTTVDELV
MCV         LREATVRVAAAEASTEKRATALPRNMQALGGESFARGAYVRRLAQVSVEQLAURMGVSLPDRTPAREC

VACV        QEINKRGTVKRIKNGSAFDLSRCLGYPEADFITLVNNRFRIENCRVNFNIESTNGI-SNFSIET
VARV        QEINKRGTVKRIKTQSAFDLSRCLGYPEADFITLVNNRFRIENCRVNFNIESTNGI-SNFSIET
MPXV        QEINKRGTVKRIKNGSVFDLSRCLGYPEADFITLVNNRFRIENCRVNFNIESTNGI-SNFSIET
CPXV        QEINKRGTVKRIKNGSAFDLSRCLGYPEADFITLVNNRFRIENCRVNFNIESTNGI-SNFSIET
MCV         AALREDAKLREPVLRTEDRDNACKYLSKQRARVVAVIRSKKEEIKQRKINSPELRSAGERRDQTLER

VACV        IGREDQVSIENIVTDVKERLPS--------------------------------
VARV        IGREDQVSIENIVTDVKERLPS--------------------------------
MPXV        IGREDQVSIENTVTDVKERLPS--------------------------------
CPXV        IGREDQVSIENAVTDVKERLPS--------------------------------
MCV         RSHROQRVAVERFLAEERLAEECDASGVKELPGGEARNAAESAVAGHGPDAEPREETEPESEE
```

Figure 8

```
VACV        -MNSVTVSHAPYTITYHDDNFPVKSQLVEFYNEVASWK-----LRDETSPIPDK----FPIQIKQPL
VARV (99%)  -MNSVTVSHAPYTITYHDDNFPVNSQLVEFYNEVASWK-----LRDETSPIPDK----FPIQIKQPL
MPXV (99%)  -MNSVTVSHAPYTITYHDDNFPVKSQLVEFYNEVASWK-----LRDETSPIPDK----FPIQIKQPL
CPXV (99%)  -MNSVTVS

POTENT POXVIRUS INHIBITOR

CROSS REFERENCE TO RELATED APPLICATIONS

This application claims the benefit of U.S. Ser. No. 61/774,781, filed on Mar. 8, 2014, which is incorporated in its entirety herein by reference.

GOVERNMENT INTEREST STATEMENT

This invention was made with government support under Grant Number 1U01AI082211-01 awarded by the National Institutes of Health. The government has certain rights in the invention.

FIELD OF THE INVENTION

The invention relates to compounds or compositions for and methods of inhibiting, treating, or abrogating a poxvirus infection.

BACKGROUND OF THE INVENTION

Smallpox can be considered the most deadly of all human infectious diseases, having killed hundreds of millions over the course of history. In 1980, smallpox became the only known human infectious disease to have been completely eradicated through a vaccination campaign conducted by the World Health Organization. However, illicit and surreptitious stocks of the virus pose a bioterrorism threat to the current population (Longini, et al. *Int. J. Infec. Dis.* 2007, 11, 98-108), the vast majority of whom have never been vaccinated due to its general discontinuance since 1980. In addition, the vaccine is contraindicated for the immune compromised segment of the population that has expanded in more recent times with the advent of AIDS and transplant recipients. In the event of a smallpox outbreak, the timing required to develop immunity by vaccination might not be sufficient for a large portion of the population. Therefore, effective therapeutics are needed to safeguard the largely immunologically naïve human population by providing immediate protection.

SUMMARY OF THE INVENTION

In one aspect, the invention provides a compound of formula (I):

(I)

wherein $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R^m$ and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 3-7 membered heterocycloalkyl group; and n is 1, 2, 3, 4, or 5;

or a pharmaceutically acceptable salt thereof.

In some embodiments, n is 1, 2, or 3.

In another aspect, the present invention provides a composition comprising a compound of formula (I), in which variables $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In another aspect, the present invention provides a composition comprising a compound of formula (II), in which variables $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In another aspect, the present invention provides a composition comprising a compound of formula (BI), in which variables $R^1$, $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In another aspect, the present invention provides a composition comprising a compound of formula (IV), in which variables $R^1$, $R^2$, $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In yet another aspect, the present invention provides a method of inhibiting, treating, or abrogating a poxvirus infection in a subject, the method comprising administering to said subject a compound of formula (II), (II)

wherein $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, heteroarylalkyl;

$R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 4-7 membered heterocycloalkyl group; and n is 0, 1, 2, 3, 4, or 5;

or a composition thereof, or a pharmaceutically acceptable salt thereof, wherein said compound can reduce, inhibit, or abrogate activity of a DNA polymerase of said poxvirus.

In some embodiments, n is 1, 2, or 3.

In yet another aspect, the present invention provides a method of inhibiting, treating, or abrogating a poxvirus infection in a subject, the method comprising administering to said subject a compound of formula (III), (III)

in which variables $R^1$, $R^2$, $R^4$, $R^5$, $R^6$, $R^7$, $R^{2'}$, $R^{3'}$, $R^{4'}$, $R^{5'}$, $R^{6'}$, and n are as defined anywhere herein, or a composition thereof, or a pharmaceutically acceptable salt thereof, wherein said compound can reduce, inhibit, or abrogate activity of a DNA polymerase of said poxvirus.

In yet another aspect, the present invention provides a method of inhibiting, treating, or abrogating a poxvirus infection in a subject, the method comprising administering to said subject a compound of formula (IV), (IV)

in which variables $R^1$, $R^2$, $R^4$, $R^5$, $R^6$, $R^7$, $R^{2'}$, $R^{3'}$, $R^{4'}$, $R^{5'}$, $R^{6'}$, and n are as defined anywhere herein, or a composition thereof, or a pharmaceutically acceptable salt thereof, wherein said compound can reduce, inhibit, or abrogate activity of a DNA polymerase The details of one or more embodiments of the invention are set forth in the accompanying description below. Other features, objects, and advantages of the invention will be apparent from the description and drawings, and from the claims.

BRIEF DESCRIPTION OF THE DRAWINGS

The invention will be better understood from a reading of the following detailed description taken in conjunction with the drawings in which like reference designators are used to designate like elements, and in which:

FIG. 8 illustrates a protein sequence alignment of the A20 protein. Vaccinia virus (VACV) (Seq ID No: 12); Variola (VARV) (Seq ID No: 13); Monkeypox (MPXV) (Seq ID No: 14); Cowpox (CPXV) (Seq ID No: 15); Molluscum contagiosum virus (MCV) (Seq ID No: 16). Percent identities are shown in parentheses.

FIG. 9 illustrates a protein sequence alignment of the D4 protein. Vaccinia virus (VACV) (Seq ID No: 17); Variola (VARV) (Seq ID No: 18); Monkeypox (MPXV) (Seq ID No: 19); Cowpox (CPXV) (Seq ID No: 20); Molluscum contagiosum virus (MCV) (Seq ID No: 21); Epstein-Ban virus (EBV) (Seq ID No: 22). Percent identities are shown in parentheses.

Figure 1:
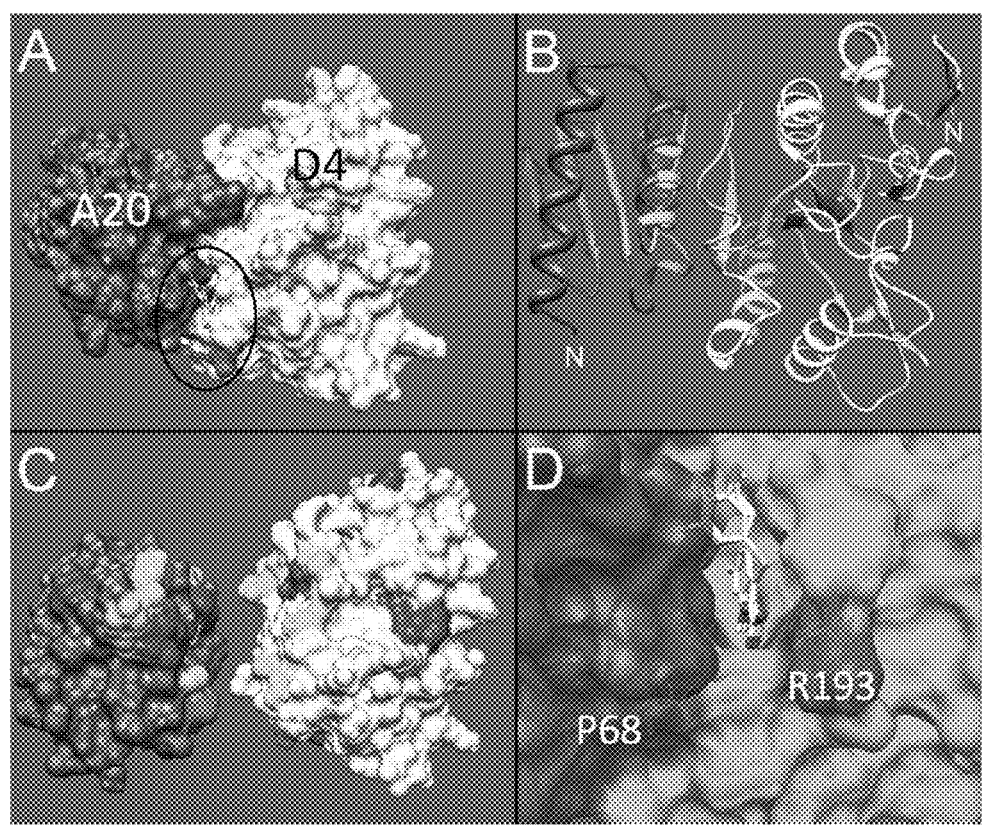
FIG. 1 illustrates a molecular docking. (A) Surface depiction of the receptor used for the study was obtained by docking the de no designed A20NT100 (green) with D4 (white). The circle represents the docking site preference by compounds. (B) Ribbon diagrams of A20NT100 (green) and D4 (white) with regions responsible for the protein-protein interface contacts depicted in yellow. Contact residues are further described in Table 6. (C) Surface depictions of A20NT100 (green) and D4 (white) with hot spots (red), interface contact residues (yellow), and amino acids P68 of A20NT100 and R193 of D4 (magenta) highlighted. (D) The docked poses of 1 and 24 with respect to amino acids P68 of A20NT100 and R193 of D4. Images are visualized using UCSF Chimera.
Figure 2:
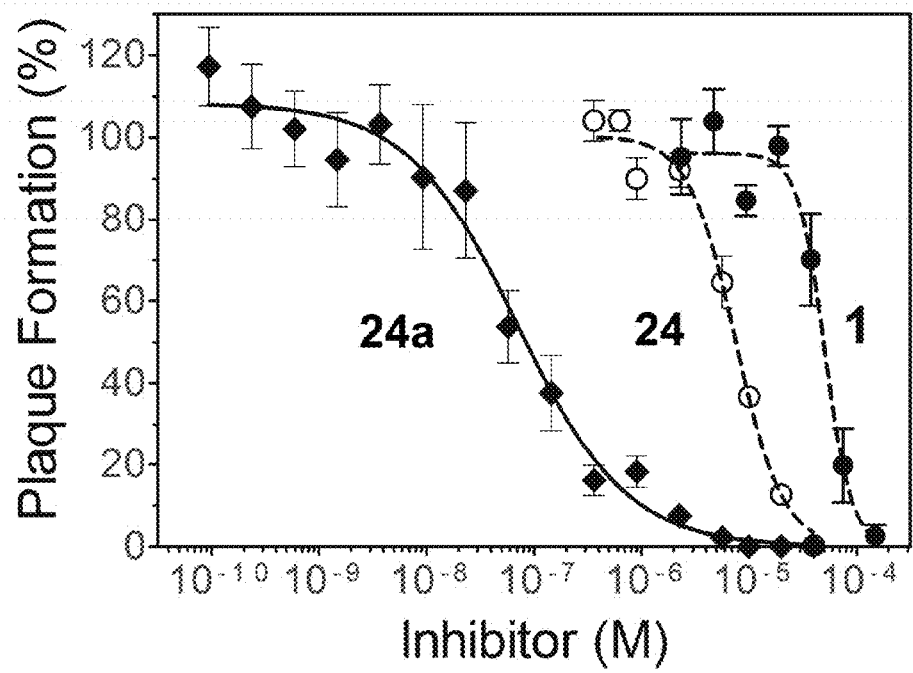
FIG. 2 depicts Dose-response curves comparing the antiviral activities of parent 1 ($IC_{50}$=82000 nM) with the medicinal chemistry derived 24 ($IC_{50}$=7000 nM) and rationally designed 24a ($IC_{50}$=42 nM).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention is directed to, in some embodiments, to a compound of formula (I)

(I)

wherein
$R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R^m$ and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 3-7 membered heterocycloalkyl group; and n is 1, 2, 3, 4, or 5;

or a pharmaceutically acceptable salt thereof.

In some embodiments, n is 1, 2, or 3. In other embodiments, n is 2. In certain embodiments, n is 1.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $C_1$-$C_6$ haloalkyl, $OR^a$, $NR^mR^n$, $NR^aCOR^b$, and $SO_2R^b$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $C_1$-$C_6$ haloalkyl, $OR^a$, and $NR^mR^n$.

In some embodiments, $R^4$, $R^5$, $R^6$, $R^7$, $R^{2'}$, $R^{3'}$, $R^{4'}$, $R^{5'}$ and $R^{6'}$ are independently selected from the group consisting of H, $C_1$-$C_6$ alkyl, halo, $CF_3$, OH, $OCH_3$, and $NH_2$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $CF_3$, OH, $OCH_3$, and $NH_2$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $CF_3$, and $OCH_3$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $CH_3$, halo, and $OCH_3$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $CH_3$, and chloro.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, aryl, heteroaryl, $C_3$-$C_7$ cycloalkyl, and 3-7 membered heterocycloalkyl.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, cycloalkylalkyl, heterocycloalkylalkyl, arylalkyl, and heteroarylalkyl.

In some embodiments, $R^4$, $R^5$, $R^6$, $R^7$, $R^{2'}$, $R^{3'}$, $R^{4'}$, $R^{5'}$, and $R^{6'}$ each independently are H, $C_1$-$C_6$ alkyl, or halo. In other embodiments, $R^4$, $R^5$, $R^6$, $R^7$, $R^{2'}$, $R^{3'}$, $R^{4'}$, $R^{5'}$, and $R^{6'}$ each independently are H, $C_1$-$C_6$ alkyl, or chloro.

In some embodiments, $R^4$, $R^5$, $R^6$, $R^7$, $R^{2'}$, $R^{3'}$, $R^{4'}$, $R^{5'}$, and $R^{6'}$ each independently are H, $CH_3$, or chloro.

In some embodiments, $R^4$, $R^5$, $R^6$, and $R^7$ each independently are H or $CH_3$. In other embodiments, one of $R^4$, $R^5$, $R^6$, and $R^7$ is $CH_3$. In certain embodiments, $R^6$ is $CH_3$. In other embodiments, two of $R^4$, $R^5$, $R^6$, and $R^7$ are $CH_3$. In certain embodiments, $R^5$ and $R^6$ are $CH_3$. In other embodiments, $R^4$, $R^5$, $R^6$, and $R^7$ all are $CH_3$.

In some embodiments, $R^4$, $R^5$, and $R^7$ are H, and $R^6$ is $CH_3$.

In some embodiments, $R^4$, $R^5$, $R^6$, and $R^7$ each independently are H or $OR^a$. In other embodiments, one of $R^4$, $R^5$, $R^6$, and $R^7$ is $OCH_3$. In certain embodiments, $R^6$ is $OCH_3$. In other embodiments, two of $R^4$, $R^5$, $R^6$, and $R^7$ are $OCH_3$. In certain embodiments, $R^5$ and $R^6$ are $OCH_3$. In other embodiments, $R^4$, $R^5$, $R^6$, and $R^7$ all are $OCH_3$.

In some embodiments, $R^4$, $R^5$, and $R^7$ are H, and $R^6$ is $OCH_3$.

In some embodiments, $R^4$, $R^5$, $R^6$, and $R^7$ each independently are H or halo. In other embodiments, one of $R^4$, $R^5$, $R^6$, and $R^7$ is halo, for example, fluoro, chloro, or bromo. In certain embodiments, $R^6$ is halo. In some embodiments, $R^6$ is chloro. In other embodiments, two of $R^4$, $R^5$, $R^6$, and $R^7$ are halo, for example fluoro. In some embodiments, two of $R^4$, $R^5$, $R^6$, and $R^7$ are chloro. In certain embodiments, $R^5$ and $R^6$ can both be halo, for example, fluoro. In other embodiments, $R^5$ and $R^6$ can both be chloro.

In some embodiments, three of $R^4$, $R^5$, $R^6$, and $R^7$ are halo. In certain embodiments, three of $R^4$, $R^5$, $R^6$, and $R^7$ are chloro. In other embodiments, $R^4$, $R^5$, $R^6$, and $R^7$ all are halo. In certain embodiments, $R^4$, $R^5$, $R^6$, and $R^7$ all are chloro.

In some embodiments, $R^4$, $R^5$, $R^6$, and $R^7$ are H.

In some embodiments, $R^{2'}$, $R^{3'}$, $R^{4'}$, $R^{5'}$, and $R^{6'}$ each independently are H or halo. In other embodiments, $R^{2'}$, $R^{3'}$, $R^{4'}$, $R^{5'}$, and $R^{6'}$ each independently are H or chloro. In some embodiments, two of $R^{2'}$, $R^{3'}$, $R^{4'}$, $R^{5'}$, and $R^{6'}$ each independently are chloro. In some embodiments, three of $R^{2'}$, $R^{3'}$, $R^{4'}$, $R^{5'}$, and $R^{6'}$ are halo. In certain embodiments, three of $R^{2'}$, $R^{3'}$, $R^{4'}$, $R^{5'}$, and $R^{6'}$ are chloro. In other embodiments, four of $R^{2'}$, $R^{3'}$, $R^{4'}$, $R^{5'}$, and $R^{6'}$ are halo. In certain embodiments, four of $R^{2'}$, $R^{3'}$, $R^{4'}$, $R^{5'}$, and $R^{6'}$ are chloro. In some embodiments, $R^{2'}$, $R^{3'}$, $R^{4'}$, $R^{5'}$, and $R^{6'}$ all are halo. In certain embodiments, $R^{2'}$, $R^{3'}$, $R^{4'}$, $R^{5'}$, and $R^{6'}$ all are chloro.

In some embodiments, $R^{3'}$ and $R^{5'}$ are halo. In other embodiments, $R^{3'}$ and $R^{5'}$ are chloro.

In some embodiments, $R^{2'}$, $R^{4'}$, and $R^{6'}$ are H, and $R^{3'}$ and $R^{5'}$ are halo. In certain embodiments, $R^{2'}$, $R^{4'}$, and $R^{6'}$ are H, and $R^{3'}$ and $R^{5'}$ are chloro.

In some embodiments, $R^{2'}$, $R^{3'}$, $R^{5'}$, and $R^{6'}$ are H, and $R^{4'}$ is halo. In certain embodiments, $R^{2'}$, $R^{3'}$, $R^{5'}$, and $R^{6'}$ are H, and $R^{4'}$ are chloro.

In some embodiments, $R^{2'}$, $R^{3'}$, $R^{4'}$, $R^{5'}$, and $R^{6'}$ are H.

In some embodiments, the compound is 3-(3-((3,5-dichlorophenyl)thio)-6-methyl-1H-indol-2-yl)propanamide; 2-(3-((3,5-dichlorophenyl)thio)-6-methyl-1H-indol-2-yl)acetamide; or 4-(3-((3,5-dichlorophenyl)thio)-6-methyl-1H-indol-2-yl)butanamide.

In some embodiments, the compound is 3-(3-((3,5-dichlorophenyl)thio)-6-methyl-1H-indol-2-yl)propanamide. In some embodiments, the compound is -(3-((3,5-dichlorophenyl)thio)-6-methyl-1H-indol-2-yl)acetamide. In other embodiments, the compound is 4-(3-((3,5-dichlorophenyl)thio)-6-methyl-1H-indol-2-yl)butanamide In some embodiments, the compound is 2-(6-methyl-3-(phenylthio)-1H-indol-2-yl)acetamide; 3-(6-methyl-3-(phenylthio)-1H-indol-2-yl)propanamide; or 4-(6-methyl-3-(phenylthio)-1H-indol-2-yl)butanamide.

In some embodiments, the compound is 2-(3-((4-chlorophenyl)thio)-6-methyl-1H-indol-2-yl)acetamide; 3-(3-((4-chlorophenyl)thio)-6-methyl-1H-indol-2-yl)propanamide; or 4-(3-((4-chlorophenyl)thio)-6-methyl-1H-indol-2-yl)butanamide It is another aspect of the present invention that the compound can have formula (II)

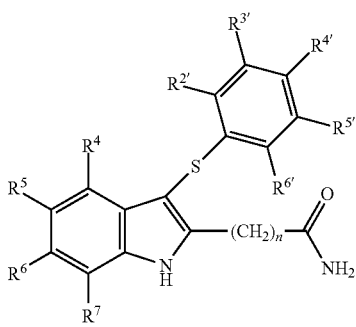

(II)

wherein
$R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, heteroarylalkyl;

$R^m$ and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 4-7 membered heterocycloalkyl group; and n is 0, 1, 2, 3, 4, or 5;

or a composition thereof, or a pharmaceutically acceptable salt thereof.

In some embodiments, n is 1, 2, 3, 4, or 5. In other embodiments, n is 1, 2, or 3.

The present invention also provides a compound of formula (III),

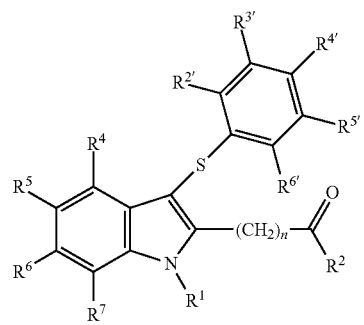

(III)

wherein
$R^1$ is H, $C_1$-$C_3$ alkyl, $C(O)OR^a$, $C(O)R^b$, $C(O)NR^mR^n$, $SOR^b$, or $SO_2R^b$;

$R^2$ is $NR^pR^q$;

$R^4$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^5$ is $C_1$-$C_6$ alkyl, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R^p$, $R^q$, $R^m$, and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 3-7 membered heterocycloalkyl group;

n is 0, 1, 2, 3, 4, or 5;

or a composition thereof, or a pharmaceutically acceptable salt thereof.

In some embodiments, n is 1, 2, 3, 4, or 5. In other embodiments, n is 1, 2, or 3.

In some embodiments, $R^1$ is $C_1$-$C_3$ alkyl, for example, methyl. In other embodiments, $R^1$ is $C(O)OR^a$, for example, $C(O)OCH_3$, or $C(O)OCH_2CH_3$.

In some embodiments, $R^2$ is $NHR^q$. In certain embodiments, $R^2$ is $NHCH_3$, or $NHCH_2CH_3$.

In some embodiments, one of $R^4$, $R^5$, $R^6$, $R^7$, $R^{2'}$, $R^{3'}$, $R^{4'}$, $R^{5'}$, and $R^{6'}$ is not H.

In some embodiments, the compound is 3-(3-((3,5-Dichlorophenyl)thio)-6-methyl-1H-indol-2-yl)-N-hexylpropanamide.

The present invention also provides a compound of formula (IV),

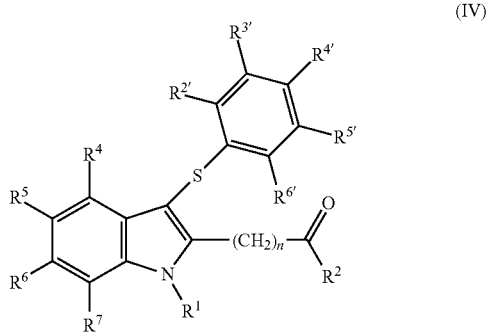

wherein
$R^1$ is H, $C_1$-$C_3$ alkyl, $C(O)OR^a$, $C(O)R^b$, $C(O)NR^mR^n$, $SOR^b$, or $SO_2R^b$;
$R^2$ is $C_1$-$C_5$ alkyl, OH, or $OC_1$-$C_5$ alkyl;
$R^4$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;
$R^5$ is $C_1$-$C_6$ alkyl, cyano, nitro, $C_1$-$C_6$ haloalkyl, $OR^a$, $SR^a$, $NR^mR^n$, $NR^aCOR^6$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;
$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;
$R^m$ and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 3-7 membered heterocycloalkyl group;
n is 0, 1, 2, 3, 4, or 5;
or a pharmaceutically acceptable salt thereof.

In some embodiments, n is 1, 2, 3, 4, or 5. In other embodiments, n is 1, 2, or 3.

In some embodiments, $R^1$ is $C_1$-$C_3$ alkyl, for example, methyl. In other embodiments, $R^1$ is $C(O)OR^a$, for example, $C(O)OCH_3$, or $C(O)OCH_2CH_3$.

In some embodiments, $R^2$ is COOH. In other embodiments, $R^2$ is $OC_1$-$C_5$ alkyl, for example, $OCH_2CH_3$.

At various places in the present specification, substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

In some embodiments, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

In some embodiments, "alkenyl" refers to an alkyl group having one or more double carbon-carbon bonds. Example alkenyl groups include ethenyl, propenyl, and the like.

In some embodiments, "alkynyl" refers to an alkyl group having one or more triple carbon-carbon bonds. Example alkynyl groups include ethynyl, propynyl, and the like.

In some embodiments, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. A cycloalkyl group having one or more fused aromatic rings are attached through either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

In some embodiments, "cycloalkylalkyl" refers to an alkyl group substituted by a cycloalkyl group. Example cycloalkylalkyl groups include cyclopropylalkyl, cyclohexylalkyl, and the like.

In some embodiments, "heterocycloalkyl" refers to a non-aromatic heterocycle where one or more of the ring-forming atoms can be a heteroatom such as an O, N, or S atom. Heterocycloalkyl groups can include mono- or polycyclic (e.g., having 2, 3 or 4 fused rings) ring systems as well as spirocycles. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl can be moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings are attached though either the aromatic or non-aromatic portion. Also included in the definition of heterocycloalkyl can be moieties where one or more ring-forming atoms can be substituted by 1 or 2 oxo or sulfido groups. In some embodiments, the to heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

In some embodiments, "heterocycloalkylalkyl" refers to an alkyl group substituted by a heterocycloalkyl group. Example heterocycloalkylalkyl groups include morpholinoalkyl and piperazinylalkyl, and the like.

In some embodiments, "aryl" refers to monocyclic or polycyclic (e.g., having 2, 3 or 4 fused rings) aromatic hydrocarbons such as, for example, phenyl, naphthyl, anthracenyl, phenanthrenyl, and the like. In some embodiments, an aryl group has from 6 to about 20 carbon atoms.

In some embodiments, "arylalkyl" refers to an alkyl group substituted by an aryl group. Example arylalkyl groups include benzyl and phenylethyl.

In some embodiments, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

In some embodiments, a "heteroarylalkyl" group refers to an alkyl group substituted by a heteroaryl group. An example of a heteroarylalkyl group is pyridylmethyl.

In some embodiments, "halo" or "halogen" includes fluoro, chloro, bromo, and iodo.

In some embodiments, "haloalkyl" refers to an alkyl group substituted by one or more halogen atoms. Examples of haloalkyl groups include $CF_3C_2F_5$, $CHF_2$, $CCl_3$, $CHCl_2$, $C_2Cl_5$, and the like.

The present invention also includes pharmaceutically acceptable salts of the compounds described herein. In some embodiments, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention are synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts can be found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

In some embodiments, examples of suitable inorganic acids include hydrochloric acid, sulphuric acid, phosphoric acid, or hydrobromic acid, while examples of suitable organic acids can include carboxylic acid, sulpho acid, or sulphonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, maleic acid, salicylic acid, 3-aminosalicylic acid, ascorbic acid, embonic acid, nicotinic acid, isonicotinic acid, oxalic acid, gluconic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Examples of suitable inorganic bases can include sodium hydroxide, potassium hydroxide and ammonia, while examples of suitable organic bases are amines, e.g., tertiary amines, such as trimethylamine, triethylamine, pyridine, N,N-dimethylaniline, quinoline, isoquinoline, α-picoline, β-picoline, γ-picoline, quinaldine, or pyrimidine.

In some embodiments, the phrase "pharmaceutically acceptable" is employed herein to refer to those compounds, materials, compositions, and/or dosage forms which can be, within the scope of sound medical judgment, suitable for use in contact with the tissues of human beings and animals without excessive toxicity, irritation, allergic response, or other problem or complication, commensurate with a reasonable benefit/risk ratio.

In some embodiments, the compound of the present invention, for example, a compound of formula (I), a compound of formula (II), a compound of formula (III), or a compound of formula (IV), can be linked to a lipid, or a derivative or analog thereof. The presence of a lipid, or a derivative or analog thereof, may promote disruption of biological membranes to facilitate intracellular delivery of the compound of the invention. The lipid includes, but is not limited to, (1) uncharged lipid components, for example, cholesterol, ceramide, diacylglycerol, acyl(polyethers) or alkylpoly(ethers); (2) neutral phospholipids, for example, diacylphosphatidylcholines, sphingomyelins, and diacylphosphatidylethanolamines, (3) anionic lipids, for example, diacylphosphatidylserine, diacylphosphatidylglycerol, diacylphosphatidate, cardiolipin, diacylphosphatidylinositol, diacylglycerolhemisuccinate, diaclyglycerolhemigluratate, cholesterylhemisuccinate, cholesterylhemiglutarate, and the like; (4) polymer-conjugated lipids, for example, N-[methoxy-(poly(ethylene glycol)diacylphosphatidylethanolamine, poly(ethylene glycol)-diacylglycerol, poly(ethylene glycol)-ceramide; and (5) cationic lipids, for example, 1,2,-diacyl-3-trimethylammonium-propane (DOTAP), dimethyldioctadecylammonium bromide (DDAB), and 1,2-diacyl-sn-glycero-3-ethylphosphocholine.

It is an important aspect that the compounds of the present invention can be used to inhibit, treat, or abrogate a poxvirus infection in a subject.

The present invention provides a method of inhibiting, treating, or abrogating a poxvirus infection in a subject, the method comprising administering to said subject a compound of formula (II), (II)

[Chemical structure of indole compound with substituents R4, R5, R6, R7 on indole ring, linked via S to phenyl with R2', R3', R4', R5', R6', and (CH2)n-C(O)NH2 side chain]

wherein $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR'''R''$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, heteroarylalkyl;

$R'''$ and $R''$ are independently selected from the group consisting of H, $C_1$-$C_6$ alkyl, cycloalkyl, cycloalkylalkyl, heterocycloalkylalkyl, arylalkyl, and heteroarylalkyl; or $R'''$ and $R''$, together with the nitrogen atom to which they are attached, form a 4-7 membered heterocycloalkyl group; and n is 0, 1, 2, 3, 4, or 5;

or a composition thereof, or a pharmaceutically acceptable salt thereof, wherein said compound can reduce, inhibit, or abrogate activity of a DNA polymerase of said poxvirus.

In some embodiments, n is 1, 2, or 3.

In some embodiments, n is 0.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $C_1$-$C_6$ haloalkyl, $OR^a$, $NR^{m}R^{n}$, $NR^aCOR^b$, and $SO_2R^b$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $C_1$-$C_6$ haloalkyl, $OR^a$, and $NR^{m}R^{n}$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $CF_3$, OH, $OCH_3$, and $NH_2$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $CF_3$, OH, $OCH_3$, and $NH_2$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, $CF_3$, and $OCH_3$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $CH_3$, halo, and $OCH_3$.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, $CH_3$, and chloro.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, aryl, heteroaryl, $C_3$-$C_7$ cycloalkyl, and 3-7 membered heterocycloalkyl.

In some embodiments, $R^4$, $R^5$, $R^6$, $R^7$, $R^{2'}$, $R^{3'}$, $R^{4'}$, $R^{5'}$, and $R^{6'}$ are independently selected from the group consisting of H, cycloalkylalkyl, heterocycloalkylalkyl, arylalkyl, and heteroarylalkyl.

In some embodiments, $R^4$, $R^5$, $R^6$, $R^7$, $R^{2'}$, $R^{3'}$, $R^{4'}$, $R^{5'}$, and $R^{6'}$ each independently are H, $C_1$-$C_6$ alkyl, or halo. In other embodiments, $R^4$, $R^5$, $R^6$, $R^7$, $R^{2'}$, $R^{3'}$, $R^{4'}$, $R^{5'}$, and $R^{6'}$ each independently are H, $C_1$-$C_6$ alkyl, or chloro.

In some embodiments, $R^4$, $R^5$, $R^6$, $R^7$, $R^{2'}$, $R^{3'}$, $R^{4'}$, $R^{5'}$, and $R^{6'}$ each independently are H, $CH_3$, or chloro.

In some embodiments, $R^4$, $R^5$, $R^6$, and $R^7$ each independently are H or $CH_3$. In other embodiments, one of $R^4$, $R^5$, $R^6$, and $R^7$ is $CH_3$. In certain embodiments, $R^6$ is $CH_3$. In other embodiments, two of $R^4$, $R^5$, $R^6$, and $R^7$ are $CH_3$. In certain embodiments, $R^5$ and $R^6$ are $CH_3$. In other embodiments, $R^4$, $R^5$, $R^6$, and $R^7$ all are $CH_3$.

In some embodiments, $R^4$, $R^5$, and $R^7$ are H, and $R^6$ is $CH_3$.

In some embodiments, $R^4$, $R^5$, $R^6$, and $R^7$ each independently are H or $OR^a$. In other embodiments, one of $R^4$, $R^5$, $R^6$, and $R^7$ is $OCH_3$. In certain embodiments, $R^6$ is $OCH_3$. In other embodiments, two of $R^4$, $R^5$, $R^6$, and $R^7$ are $OCH_3$. In certain embodiments, $R^5$ and $R^6$ are $OCH_3$. In other embodiments, $R^4$, $R^5$, $R^6$, and $R^7$ all are $OCH_3$.

In some embodiments, $R^4$, $R^5$, and $R^7$ are H, and $R^6$ is $OCH_3$.

In some embodiments, $R^4$, $R^5$, $R^6$, and $R^7$ each independently are H or halo. In other embodiments, one of $R^4$, $R^5$, $R^6$, and $R^7$ is halo, for example, fluoro, chloro, or bromo. In certain embodiments, $R^6$ is halo. In some embodiments, $R^6$ is chloro. In other embodiments, two of $R^4$, $R^5$, $R^6$, and $R^7$ are halo, for example fluoro. In some embodiments, two of $R^4$, $R^5$, $R^6$, and $R^7$ are chloro. In certain embodiments, $R^5$ and $R^6$ both are halo, for example, fluoro. In other embodiments, $R^5$ and $R^6$ both are chloro.

In some embodiments, three of $R^4$, $R^5$, $R^6$, and $R^7$ are halo. In certain embodiments, three of $R^4$, $R^5$, $R^6$, and $R^7$ are chloro. In other embodiments, $R^4$, $R^5$, $R^6$, and $R^7$ all are halo. In certain embodiments, $R^4$, $R^5$, $R^6$, and $R^7$ all are chloro.

In some embodiments, $R^4$, $R^5$, $R^6$, and $R^7$ are H.

In some embodiments, $R^{2'}$, $R^{3'}$, $R^{4'}$, $R^{5'}$, and $R^{6'}$ each independently are H or halo. In other embodiments, $R^{2'}$, $R^{3'}$, $R^{4'}$, $R^{5'}$, and $R^{6'}$ each independently are H or chloro. In some embodiments, two of $R^{2'}$, $R^{3'}$, $R^{4'}$, $R^{5'}$, and $R^{6'}$ each independently are chloro. In some embodiments, three of $R^{2'}$, $R^{3'}$, $R^{4'}$, $R^{5'}$, and $R^{6'}$ are halo. In certain embodiments, three of $R^{2'}$, $R^{3'}$, $R^{4'}$, $R^{5'}$, and $R^{6'}$ are chloro. In other embodiments, four of $R^{2'}$, $R^{3'}$, $R^{4'}$, $R^{5'}$, and $R^{6'}$ are halo. In certain embodiments, four of $R^{2'}$, $R^{3'}$, $R^{4'}$, $R^{5'}$, and $R^{6'}$ are chloro. In some embodiments, $R^{2'}$, $R^{3'}$, $R^{4'}$, $R^{5'}$, and $R^{6'}$ all are halo. In certain embodiments, $R^{2'}$, $R^{3'}$, $R^{4'}$, $R^{5'}$, and $R^{6'}$ all are chloro.

In some embodiments, $R^{3'}$ and $R^{5'}$ are halo. In other embodiments, $R^{3'}$ and $R^{5'}$ are chloro.

In some embodiments, $R^{2'}$, $R^{4'}$, and $R^{6'}$ are H, and $R^{3'}$ and $R^{5'}$ are halo. In certain embodiments, $R^{2'}$, $R^{4'}$, and $R^{6'}$ are H, and $R^{3'}$ and $R^{5'}$ are chloro.

In some embodiments, $R^{2'}$, $R^{3'}$, $R^{5'}$, and $R^{6'}$ are H, and $R^{4'}$ is halo. In certain embodiments, $R^{2'}$, $R^{3'}$, $R^{5'}$, and $R^{6'}$ are H, and $R^{4'}$ is chloro.

In some embodiments, $R^{2'}$, $R^{3'}$, $R^{4'}$, $R^{5'}$, and $R^{6'}$ are H.

In some embodiments, the compound is 3-(3-((3,5-dichlorophenyl)thio)-6-methyl-1H-indol-2-yl)propanamide; 2-(3-((3,5-dichlorophenyl)thio)-6-methyl-1H-indol-2-yl)acetamide; or 4-(3-((3,5-dichlorophenyl)thio)-6-methyl-1H-indol-2-yl)butanamide.

In some embodiments, the compound is 3-(3-((3,5-dichlorophenyl)thio)-6-methyl-1H-indol-2-yl)propanamide. In some embodiments, the compound is 2-(3-((3,5-dichlorophenyl)thio)-6-methyl-1H-indol-2-yl)acetamide. In other embodiments, the compound is 4-(3-((3,5-dichlorophenyl)thio)-6-methyl-1H-indol-2-yl)butanamide In some embodiments, the compound is 2-(6-methyl-3-(phenylthio)-1H-indol-2-yl)acetamide; 3-(6-methyl-3-(phenylthio)-1H-indol-2-yl)propanamide; or 4-(6-methyl-3-(phenylthio)-1H-indol-2-yl)butanamide.

In some embodiments, the compound is 2-(3-((4-chlorophenyl)thio)-6-methyl-1H-indol-2-yl)acetamide; 3-(3-((4-chlorophenyl)thio)-6-methyl-1H-indol-2-yl)propanamide; or 4-(3-((4-chlorophenyl)thio)-6-methyl-1H-indol-2-yl)butanamide.

In some embodiments, the compound of formula (II) has formula (I):

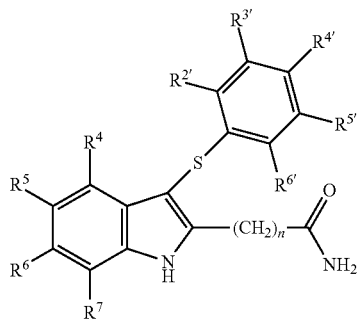

(I)

in which variables $R^4$, $R^5$, $R^6$, $R^7$, $R^{2'}$, $R^{3'}$, $R^{4'}$, $R^{5'}$, $R^{6'}$, and n are as defined anywhere herein.

In some embodiments, the poxvirus is a vaccinia virus. In other embodiments, the poxvirus is a variola virus. In certain embodiments, the poxvirus is a molluscum contagiosum virus.

In some embodiments, the step of inhibiting a poxvirus infection in a subject can include the step of inhibiting DNA synthesis of said poxvirus.

In some embodiments, the DNA polymerase is an E9 DNA polymerase or a homologue thereof from a different species.

In some embodiments, the compound can reduce, inhibit, or abrogate interaction of said DNA polymerase with a processivity factor. In some embodiments, the processivity factor is an A20 or D4R processivity factor or a homologue thereof from a different species.

In some embodiments, the subject is a human.

The method of inhibiting, treating, or abrogating a poxvirus infection in a subject comprises the step of administering to said subject an effective amount compound of the present invention. The term "an effective amount" refers to the amount of active compound or pharmaceutical agent that elicits the biological or medicinal response that is being sought in a tissue, system, animal, individual or human by a researcher, veterinarian, medical doctor or other clinician.

In some embodiments, the present invention provides a method of inhibiting, treating, or abrogating a poxvirus infection in a subject, the method comprising administering to said subject a compound of formula (III),

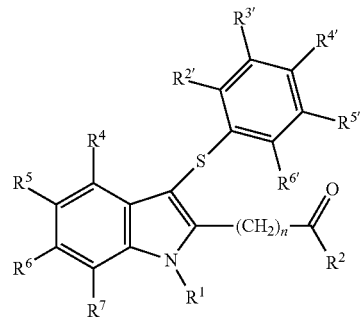

(III)

in which variables $R^1$, $R^2$, $R^4$, $R^5$, $R^6$, $R^7$, $R^{2'}$, $R^{3'}$, $R^{4'}$, $R^{5'}$, $R^{6'}$, and n are as defined anywhere herein, or a composition thereof, or a pharmaceutically acceptable salt thereof, wherein said compound can reduce, inhibit, or abrogate activity of a DNA polymerase of said poxvirus.

In some embodiments, the present invention provides a method of inhibiting, treating, or abrogating a poxvirus infection in a subject, the method comprising administering to said to subject a compound of formula (IV),

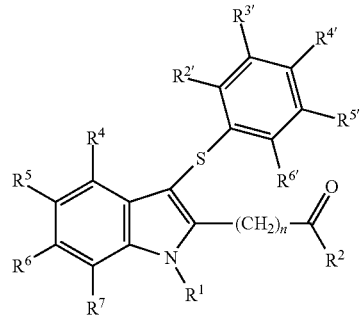

(IV)

$R^1$ is H, $C_1$-$C_3$ alkyl, C(O)OR$^a$, C(O)R$^b$, C(O)NR$^m$R$^n$, SOR$^b$, or SO$_2$R$^b$;

$R^2$ is $C_1$-$C_5$ alkyl, OH, or OC$_1$-$C_5$ alkyl;

$R^4$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, OR$^a$, SR$^a$, NR$^m$R$^n$, NR$^a$COR$^b$, SOR$^b$, SO$_2$R$^b$, COR$^b$, COOR$^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^5$ is $C_1$-$C_6$ alkyl, cyano, nitro, $C_1$-$C_6$ haloalkyl, OR$^a$, SR$^a$, NR$^m$R$^n$, NR$^a$COR$^b$, SOR$^b$, SO$_2$R$^b$, COR$^b$, COOR$^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R^m$ and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 3-7 membered heterocycloalkyl group;

n is 0, 1, 2, 3, 4, or 5;

or a pharmaceutically acceptable salt thereof.

wherein said compound can reduce, inhibit, or abrogate activity of a DNA polymerase.

In some embodiments, n is 0. In other embodiments, n is 1, 2, or 3.

In some embodiments, $R^1$ is H. In other embodiments, $R^1$ is $C_1$-$C_3$ alkyl, for example, $CH_3$.

In some embodiments, $R^2$ is OH or $OC_1$-$C_5$ alkyl. In other embodiments, $R^2$ is OH. In certain embodiments, $R^2$ is $OCH_3$. In some embodiments, $R^2$ is $OC_2H_5$.

In some embodiments, $R^4$, $R^6$, and $R^7$, $R^{2'}$, $R^{3'}$, $R^{4'}$, $R^{5'}$, and $R^{6'}$ each independently are H, $C_1$-$C_6$ alkyl, or halo.

In some embodiments, $R^4$, $R^6$, and $R^7$ each independently are H or $CH_3$.

In some embodiments, $R^4$, and $R^7$ are H, and $R^6$ is $CH_3$.

In some embodiments, $R^5$ is $C_1$-$C_6$ alkyl, cyano, $C_1$-$C_6$ haloalkyl, or $OR^a$.

In some embodiments, $R^5$ is $C_1$-$C_6$ alkyl or $OR^a$. In other embodiments, $R^5$ is $CH_3$ or $OCH_3$. In certain embodiments, $R^5$ is $CH_3$.

In some embodiments, wherein $R^{2'}$, $R^{3'}$, $R^{4'}$, $R^{5'}$, and $R^{6'}$ each independently are H or halo.

In some embodiments, $R^{2'}$, $R^{3'}$, $R^{4'}$, $R^{5'}$, and $R^{6'}$ are H.

In some embodiments, $R^{2'}$, $R^{4'}$, and $R^{6'}$ are H, and $R^{3'}$ and $R^{5'}$ are chloro.

In some embodiments, the compound is 3-((3,5-Dichlorophenyl)thio)-6-methyl-1H-indole-2-carboxylic acid.

In some embodiments, the compound is 3-(3-((3,5-Dichlorophenyl)thio)-6-methyl-1H-indol-2-yl)propanoic acid.

In some embodiments, the compound of the present invention can be used for inhibiting, treating, or abrogating a poxvirus infection in a subject.

In some embodiments, the poxvirus is a vaccinia virus. In other embodiments, the poxvirus is a variola virus. In certain embodiments, the poxvirus is a molluscum contagiosum virus.

In some embodiments, the step of inhibiting a poxvirus infection in a subject can include the step of inhibiting DNA synthesis of said poxvirus.

In some embodiments, the DNA polymerase is an E9 DNA polymerase or a homologue thereof from a different species.

In some embodiments, the compound can reduce, inhibit, or abrogate interaction of said DNA polymerase with a processivity factor. In some embodiments, the processivity factor is an A20 or D4R processivity factor or a homologue thereof from a different species.

In some embodiments, the subject is a human.

In certain embodiments, the poxvirus as described herein infects vertebrates. In certain embodiments, the poxvirus as described herein infects invertebrates. In certain embodiments, the poxvirus of the present causes a variety of diseases of veterinary and medical importance. In certain embodiments, the poxvirus as described herein belongs to the chordopoxyirinae subfamily. In another embodiment, the poxvirus as described herein is variola virus (smallpox virus). In another embodiment, the poxvirus is vaccinia virus. In another embodiment, the poxvirus is molluscum contagiosum virus. In other embodiments, the poxvirus is selected from an orthopoxvirus, parapoxvirus, and yatapoxvirus.

In another embodiment, the poxvirus is a cowpox virus. In another embodiment, the poxvirus is a monkeypox virus. In another embodiment, the poxvirus is a raccoonpox virus. In another embodiment, the poxvirus is a camelpox virus. In another embodiment, the poxvirus is a skunkpox virus. In another embodiment, the poxvirus is a volepox virus. In another embodiment, the poxvirus is an ectromelia virus. In another embodiment, the poxvirus is a taterapox virus.

In another embodiment, the poxvirus is a parapoxvirus. In another embodiment, the poxvirus is an orf virus. In another embodiment, the poxvirus is a pseudocowpox virus In another embodiment, the poxvirus is an avipoxvirus. In another embodiment, the poxvirus is a canarypox virus. In another embodiment, the poxvirus is a fowlpox virus.

In another embodiment, the poxvirus is a capripoxvirus. In another embodiment, the poxvirus is a goatpox virus. In another embodiment, the poxvirus is a lumpy skin disease virus.

In another embodiment, the poxvirus is a leporipoxvirus. In another embodiment, the poxvirus is a myxoma virus. In another embodiment, the poxvirus is a fibroma virus.

In another embodiment, the poxvirus is a molluscipoxvirus. In another embodiment, the poxvirus is a molluscum contagiosum virus.

In another embodiment, the poxvirus is a yatapoxvirus. In another embodiment, the poxvirus is a tanapox virus. In another embodiment, the poxvirus is a Yaba monkey tumor virus.

In certain embodiments, methods of inhibiting replication of a poxvirus comprise methods of inhibiting the DNA thereof. In certain embodiments, inhibiting the DNA replication is achieved by inhibiting activity of a DNA polymerase protein. In certain embodiments, inhibiting a DNA polymerase protein activity comprises reducing the processivity of a DNA polymerase.

In another embodiment, the DNA polymerase that is inhibited is an E9 protein. In another embodiment, the DNA polymerase is a variola DNA polymerase. In another embodiment, the DNA polymerase has a sequence set forth in 1 of the following GenBank Accession Numbers: DQ437580; DQ437581; DQ437582; DQ437583-92, inclusive; DQ441416-48, inclusive.

In certain embodiments, DNA polymerase protein processive activity is inhibited in the presence of an accessory protein. In another embodiment, interaction of a DNA polymerase with an accessory protein is inhibited or reduced. In another embodiment, interaction of a DNA polymerase with a processivity factor is inhibited or reduced. In another embodiment, an E9 DNA polymerase processivity accessory protein or processivity factor is a stoichiometric component of the processive form of poxvirus DNA polymerase. In another embodiment, the accessory protein is an A20 protein. In another embodiment, the accessory protein is a D4R (D4; UDG). In another embodiment, the accessory protein is a D5 gene product. In another embodiment, the accessory protein is an H5 gene product. In another embodiment, the accessory protein is a homologue of A20 from another species. In another embodiment, the accessory protein is a homologue of D4 from another species. In another embodiment, the accessory protein is a homologue of D5 from another species. In another embodiment, the accessory protein is a homologue of H5 from another species.

In certain embodiments, the poxvirus E9 DNA polymerase protein is at least 70% homologous to a vaccinia virus E9 DNA polymerase protein sequence. In another embodiment, the homology is at least 75%. In another embodiment, the homology is at least 80%. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In another embodiment, the E9 DNA polymerase protein is a variola virus E9 DNA polymerase protein. In another embodiment, the E9 DNA polymerase protein is at least 80% homologous to variola virus E9 DNA polymerase protein. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In certain embodiments, the poxvirus E9 DNA polymerase processivity accessory protein is at least 70% homologous to vaccinia virus A20 protein sequence. In another embodiment, the homology is at least 75%. In another embodiment, the homology is at least 80%. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In another embodiment, the poxvirus E9 DNA polymerase processivity accessory protein is an A20 variola virus processivity accessory protein. In another embodiment, the poxvirus E9 DNA polymerase processivity accessory protein is at least 80% homologous to variola virus A20 protein sequence. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In certain embodiments, the poxvirus E9 DNA polymerase processivity accessory protein is at least 70% homologous to vaccinia virus D4R protein sequence. In another embodiment, the homology is at least 75%. In another embodiment, the homology is at least 80%. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In another embodiment, the poxvirus E9 DNA polymerase processivity accessory protein is a D4R variola virus processivity accessory protein. In another embodiment, the poxvirus E9 DNA polymerase processivity accessory protein is at least 80% homologous to a variola virus D4R protein sequence. In another embodiment, the homology is at least 85%. In another embodiment, the homology is at least 88%. In another embodiment, the homology is at least 90%. In another embodiment, the homology is at least 92%. In another embodiment, the homology is at least 95%. In another embodiment, the homology is at least 97%. In another embodiment, the homology is at least 98%.

In certain embodiments, contacting a poxvirus with a compound as described herein comprises the step of adding the compound to a petri dish comprising cells infected with a poxvirus. In certain embodiments, contacting a poxvirus with a compound as described herein comprises adding the compound to a petri dish comprising an organ culture infected with a poxvirus. In certain embodiments, contacting a poxvirus with a compound as described herein comprises administering the compound to an animal and/or subject infected with a poxvirus.

In certain embodiments, a compound as described herein is solubilized in a buffer compatible with the media comprising cells or a tissue culture. In another embodiment, a compound as described herein is solubilized in the media comprising cells or a tissue culture. In certain embodiments, a compound as described herein is suspended or otherwise emulsified by methods known to one skilled in the art.

In certain embodiments, the present invention provides methods of inhibiting, a poxvirus infection in an animal and/or subject comprising administering to an animal and/or subject a compound of the present invention. In certain embodiments, the term inhibiting comprises restraining, holding back, repressing, or preventing.

In some embodiments, the compound of the present invention utilized in methods as described herein can have an $IC_{50}$ for a poxvirus of about 30 nM. In some embodiments, the $IC_{50}$ are about 100 nM. In other embodiments, the $IC_{50}$ are about 200 nM.

In some embodiments, the compound of the present invention utilized in methods as described herein can have an $IC_{50}$ for a poxvirus of about 10,000 nM or less. In some embodiments, the compound of the invention can have an $IC_{50}$ of about 5,000 nM or less. In some embodiments, the compound of the invention can have an $IC_{50}$ of about 1,000 nM or less. In some embodiments, the compound of the invention can have an $IC_{50}$ of about 750 nM or less. In some embodiments, the compound of the invention can have an $IC_{50}$ of about 500 nM or less. In some embodiments, the compound of the invention can have an $IC_{50}$ of about 250 nM or less. In some embodiments, the compound of the invention can have an $IC_{50}$ of about 200 nM or less. In other embodiments, the compound of the invention can have an $IC_{50}$ of about 175 nM or less. In other embodiments, the compound of the invention can have an $IC_{50}$ of 150 nM or less. In some embodiments, the compound of the invention can have an $IC_{50}$ of about 125 nM or less. In some embodiments, the compound of the invention can have an $IC_{50}$ of about 100 nM or less. In certain embodiments, the compound of the invention can have an $IC_{50}$ of about 75 nM or less. In other embodiments, the compound of the invention can have an $IC_{50}$ of about 50 nM or less. In certain embodiments, the compound of the invention can have an $IC_{50}$ of about 30 nM or less. In other embodiments, the compound of the invention can have an $IC_{50}$ of about 20 nM or less.

In some embodiments, the compound of the present invention utilized in methods as described herein can have an $IC_{50}$ for a poxvirus of about 40 nM. In some embodiments, the compound of the present invention utilized in methods as described herein can have an $IC_{50}$ for a poxvirus of about 50 nM. In some embodiments, the compound of the present invention utilized in methods as described herein can have an $IC_{50}$ for a poxvirus of about 200 nM. In some embodiments, the compound of the present invention utilized in methods as described herein can have an $IC_{50}$ for a poxvirus of about 250 nM.

In some embodiments, the compound of the present invention utilized in methods as described herein can have an $IC_{50}$ for a poxvirus of from about 100,000 nM or less. In some embodiments, the compound of the invention can have an $IC_{50}$ of about 75,000 nM or less. In some embodiments, the compound of the invention can have an antiviral $IC_{50}$ of about 50,000 nM or less. In some embodiments, the compound of the invention can have an $IC_{50}$ of about 25,000 nM or less. In some embodiments, the compound of the invention can have an $IC_{50}$ of about 10,000 nM or less. In some embodiments, the compound of the invention can have an $IC_{50}$ of about 7,500 nM or less. In some embodiments, the compound of the invention can have an $IC_{50}$ of about 5,000 nM or less. In some embodiments, the compound of the invention can have an $IC_{50}$ of about 2,500 nM or less. In some embodiments, the compound of the invention can have an $IC_{50}$ of about 1,000 nM or less. In some embodiments, the compound of the invention can have an $IC_{50}$ of about 750 nM or less. In some embodiments, the compound of the invention can have an $IC_{50}$ of about 500 nM or less. In some embodiments, the compound of the invention can have an $IC_{50}$ of about 250 nM or less. In some embodiments, the compound of the invention can have an $IC_{50}$ of about 225 nM or less. In some embodiments, the compound of the invention can have an $IC_{50}$ of about 200 nM or less. In some embodiments, the compound of the invention can have an $IC_{50}$ of about 150 nM or less. In some embodiments, the compound of the invention can have an $IC_{50}$ of about 125 nM or less. In some embodiments, the compound of the invention can have an $IC_{50}$ of about 100 nM or less. In some embodiments, the compound of the invention can have an $IC_{50}$ of about 75 nM or less. In some embodiments, the compound of the invention can have an $IC_{50}$ of about 50 nM or less. In some embodiments, the compound of the invention can have an $IC_{50}$ of about 40 nM or less.

In some embodiments, the compound of the invention can have an $IC_{50}$ for a poxvirus of from about 20 nM to about 1,000 nM. In some embodiments, the compound of the invention can have an $IC_{50}$ of from about 20 nM to about 750 nM. In some embodiments, the compound of the invention can have an $IC_{50}$ of from about 20 nM to about 500 nM. In some embodiments, the compound of the invention can have $IC_{50}$ of from about 20 nM to about 250 nM. In some embodiments, the compound of the invention can have an $IC_{50}$ of from about 20 nM to about 225 nM. In some embodiments, the compound of the invention can have an $IC_{50}$ of from about 20 nM to about 200 nM. In some embodiments, the compound of the invention can have an $IC_{50}$ of from about 20 nM to about 150 nM. In some embodiments, the compound of the invention can have an $IC_{50}$ of from about 20 nM to about 125 nM. In some embodiments, the compound of the invention can have an $IC_{50}$ of from about 20 nM to about 100 nM. In some embodiments, the compound of the invention can have an $IC_{50}$ of from about 20 nM to about 75 nM. In some embodiments, the compound of the invention can have an $IC_{50}$ of from about 20 nM to about 50 nM.

In some embodiments, the compound of the invention can have an $IC_{50}$ for a poxvirus of from about 30 nM to about 1,000 nM. In some embodiments, the compound of the invention can have an $IC_{50}$ of from about 30 nM to about 750 nM. In some embodiments, the compound of the invention can have an $IC_{50}$ of from about 30 nM to about 500 nM. In some embodiments, the compound of the invention can have an $IC_{50}$ of from about 30 nM to about 250 nM. In some embodiments, the compound of the invention can have an $IC_{50}$ of from about 30 nM to about 225 nM. In some embodiments, the compound of the invention can have an $IC_{50}$ of from about 30 nM to about 200 nM. In some embodiments, the compound of the invention can have an $IC_{50}$ of from about 30 nM to about 150 nM. In some embodiments, the compound of the invention can have an $IC_{50}$ of from about 30 nM to about 125 nM. In some embodiments, the compound of the invention can have an $IC_{50}$ of from about 30 nM to about 100 nM. In some embodiments, the compound of the invention can have an $IC_{50}$ of from about 30 nM to about 75 nM. In some embodiments, the compound of the invention can have an $IC_{50}$ of from about 30 nM to about 50 nM.

In some embodiments, the compound of the present invention can have a selectivity index (SI) of about 120. In some embodiments, the compound of the present invention can have a selectivity index (SI) of about 150. In some embodiments, the compound of the present invention can have a selectivity index (SI) of about 370. In some embodiments, the compound of the present invention can have a selectivity index (SI) of about 570.

In some embodiments, the compound of the present invention can have a selectivity index (SI) of about 10 or more. In some embodiments, the compound of the present invention can have a selectivity index (SI) of about 50 or more. In some embodiments, the compound of the present invention can have a selectivity index (SI) of about 100 or more. In some embodiments, the compound of the present invention can have a selectivity index (SI) of about 150 or more. In some embodiments, the compound of the present invention can have a selectivity index (SI) of about 200 or more. In some embodiments, the compound of the present invention can have a selectivity index (SI) of about 250 or more. In some embodiments, the compound of the present invention can have a selectivity index (SI) of about 300 or more. In some embodiments, the compound of the present invention can have a selectivity index (SI) of about 350 or more. In some embodiments, the compound of the present invention can have a selectivity index (SI) of about 400 or more. In some embodiments, the compound of the present invention can have a selectivity index (SI) of about 450 or more. In some embodiments, the compound of the present invention can have a selectivity index (SI) of about 500 or more. In some embodiments, the compound of the present invention can have a selectivity index (SI) of about 600 or more. In some embodiments, the compound of the present invention can have a selectivity index (SI) of about 700 or more. In some embodiments, the compound of the present invention can have a selectivity index (SI) of about 800 or more. In some embodiments, the compound of the present invention can have a selectivity index (SI) of about 900 or more.

In some embodiments, the compound of the present invention can have a selectivity index (SI) of from about 50 to about 600. In some embodiments, the compound of the present invention can have a selectivity index (SI) of from about 100 to about 600. In some embodiments, the compound of the present invention can have a selectivity index (SI) of from about 150 to about 600. In some embodiments, the compound of the present invention can have a selectivity index (SI) of from about 200 to about 600. In some embodiments, the compound of the present invention can have a selectivity index (SI) of from about 250 to about 600. In some embodiments, the compound of the present invention can have a selectivity index (SI) of from about 300 to about 600. In some embodiments, the compound of the present invention can have a selectivity index (SI) of from about 350 to about 600. In some embodiments, the compound of the present invention can have a selectivity index (SI) of from about 400 to about 600. In some embodiments, the compound of the present invention can have a selectivity index (SI) of from about 450 to about 600. In some embodiments, the compound of the present invention can have a selectivity index (SI) of from about 500 to about 600.

In some embodiments, the compound of the present invention can have a binding efficiency index (BEI) of about 15. In other embodiments, the compound of the invention can have a binding efficiency index of about 17. In other embodiments, the compound of the invention can have a binding efficiency index of about 18. In other embodiments, the compound of the invention can have a binding efficiency index of about 19. In other embodiments, the compound of the invention can have a binding efficiency index of about 20.

In some embodiments, the compound of the invention can have a binding efficiency index of about 10 or more. In some embodiments, the compound of the invention can have a binding efficiency index of about 12 or more. In some embodiments, the compound of the invention can have a binding efficiency index of about 14 or more. In some embodiments, the compound of the invention can have a binding efficiency index of about 15 or more. In some embodiments, the compound of the invention can have a binding efficiency index of about 16 or more. In some embodiments, the compound of the invention can have a binding efficiency index of about 17 or more. In some embodiments, the compound of the invention can have a binding efficiency index of about 18 or more. In some embodiments, the compound of the invention can to have a binding efficiency index of about 19 or more. In some embodiments, the compound of the invention can have a binding efficiency index of about 20 or more. In other embodiments, the compound of the invention can have a binding efficiency index of about 21 or more. In some embodiments, the compound of the invention can have a binding efficiency index of about 22 or more. In some embodiments, the compound of the invention can have a binding efficiency index of about 23 or more. In some embodiments, the compound of the invention can have a binding efficiency index of about 24 or more. In some embodiments, the compound of the invention can have a binding efficiency index of about 25 or more.

The present invention provides methods of inhibiting, treating, or abrogating a poxvirus infection in a subject; inhibiting replication of a poxvirus; inhibiting activity of a poxvirus DNA polymerase; and decreasing processivity of a poxvirus DNA polymerase, comprising contacting a poxvirus with a compound of the present invention.

In certain embodiments, the present invention provides methods of treating a poxvirus infection in an animal and/or subject comprising administering to an animal and/or subject a compound of the present invention.

In certain embodiments, the present invention provides methods of abrogating a poxvirus infection in an animal and/or subject comprising administering to an animal and/or subject a compound of the present invention. In certain embodiments, the term abrogating comprises abolishing or terminating.

The present invention, in some embodiments, provides a composition that includes a compound of formula (I), in which variables $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In some embodiments, the present invention provides a composition comprising a compound of formula (II) in which variables $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In some embodiments, the present invention provides a composition comprising a compound of formula (BI) in which variables $R^1$, $R^2$, $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In some embodiments, the present invention provides a composition comprising a compound of formula (IV) in which variables $R^1$, $R^2$, $R^4$, $R^5$, $R^6$, $R^7$, $R^{2'}$, $R^{3'}$, $R^{4'}$, $R^{5'}$, $R^{6'}$, and n are as defined anywhere herein, or a pharmaceutically acceptable salt thereof, and at least one pharmaceutically acceptable carrier.

In some embodiments, the compounds of this invention are formulated into a pharmaceutical dosage form. In certain embodiments, the pharmaceutical dosage form further comprises pharmaceutically acceptable carriers, excipients, emollients, stabilizers, etc., as are known in the pharmaceutical industry. In some embodiments the pharmaceutical dosage will include other active agents such immune system modifiers. In another embodiment, other compounds for stabilizing, preserving, the formulation and the like, but are not involved directly in the therapeutic effect of the indicated active ingredient, are included.

In certain embodiments, the pharmaceutical compositions containing the compounds as described herein are administered to a subject by any method known to a person skilled in the art, such as parenterally, paracancerally, transmucosally, transdermally, intramuscularly, intravenously, intradermally, subcutaneously, intraperitonealy, intraventricularly, intracranially, intravaginally or intratumorally.

Various embodiments of dosage ranges are contemplated by this invention. In one embodiment, the dosage of the compounds as described herein is in the range of 0.1-100 mg/day. In another embodiment, the dosage is in the range of 0.1-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day.

If the preferred mode is administered orally, in another embodiment, a unit dosage form comprises tablets, capsules, lozenges, chewable tablets, suspensions, emulsions and the like. In certain embodiments, such unit dosage forms comprise a safe and effective amount of the desired compound, or compounds, each of which is in another embodiment, from about 0.5 or 10 mg to about 300 mg/70 kg, or in another embodiment, about 0.5 or 10 mg to about 210 mg/70 kg. In certain embodiments, the pharmaceutically-acceptable carrier suitable for the preparation of unit dosage forms for peroral administration is well-known in the art. In certain embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In certain embodiments, glidants such as silicon dioxide are used to improve flow characteristics of the powder-mixture. In certain embodiments, coloring agents, such as the FD&C dyes, are added for appearance. In certain embodiments, sweeteners and flavoring agents, such as aspartame, saccharin, menthol, peppermint, and fruit flavors, are useful adjuvants for chewable tablets. In certain embodiments, capsules typically comprise one or more solid diluents disclosed above. In certain embodiments, the selection of carrier components depends on secondary considerations like taste, cost, and shelf stability, which are not critical for the purposes of this invention, and are readily made by a person skilled in the art.

In certain embodiments, peroral compositions comprise liquid solutions, emulsions, suspensions, and the like. In certain embodiments, the pharmaceutically-acceptable carriers suitable for preparation of such compositions are well known in the art. In certain embodiments, liquid oral compositions comprise, in certain embodiments, from about 0.012% to about 0.933% of the desired compound or compounds, or in another embodiment, from about 0.033% to about 0.7%.

In another embodiment, the dosage is 10-20 μg/tablet. In another embodiment, the dosage is 20-30 μg/tablet. In another embodiment, the dosage is 20-40 μg/tablet. In another embodiment, the dosage is 30-60 μg/tablet. In another embodiment, the dosage is 40-80 µg/tablet. In another embodiment, the dosage is 50-100 µg/tablet. In another embodiment, the dosage is 50-150 µg/tablet. In another embodiment, the dosage is 100-200 µg/tablet. In another embodiment, the dosage is 200-300 µg/tablet. In another embodiment, the dosage is 300-400 µg/tablet. In another embodiment, the dosage is 400-600 µg/tablet. In another embodiment, the dosage is 500-800 µg/tablet. In another embodiment, the dosage is 800-1000 µg/tablet. In another embodiment, the dosage is 1000-1500 µg/tablet. In another embodiment, the dosage is 1500-2000 µg/tablet. In another embodiment, the dosage is 2-3 mg/tablet. In another embodiment, the dosage is 2-5 mg/tablet. In another embodiment, the dosage is 2-10 mg/tablet. In another embodiment, the dosage is 2-20 mg/tablet. In another embodiment, the dosage is 2-30 mg/tablet. In another embodiment, the dosage is 2-50 mg/tablet. In another embodiment, the dosage is 2-80 mg/tablet. In another embodiment, the dosage is 2-100 mg/tablet. In another embodiment, the dosage is 3-10 mg/tablet. In another embodiment, the dosage is 3-20 mg/tablet. In another embodiment, the dosage is 3-30 mg/tablet. In another embodiment, the dosage is 3-50 mg/tablet. In another embodiment, the dosage is 3-80 mg/tablet. In another embodiment, the dosage is 3-100 mg/tablet. In another embodiment, the dosage is 5-10 mg/tablet. In another embodiment, the dosage is 5-20 mg/tablet. In another embodiment, the dosage is 5-30 mg/tablet. In another embodiment, the dosage is 5-50 mg/tablet. In another embodiment, the dosage is 5-80 mg/tablet. In another embodiment, the dosage is 5-100 mg/tablet. In another embodiment, the dosage is 10-20 mg/tablet. In another embodiment, the dosage is 10-30 mg/tablet. In another embodiment, the dosage is 10-50 mg/tablet. In another embodiment, the dosage is 10-80 mg/tablet. In another embodiment, the dosage is 10-100 mg/tablet.

In some embodiments, compositions for use in the methods of this invention comprise solutions or emulsions, which in another embodiment are aqueous solutions or emulsions comprising a safe and effective amount of a compound as described herein and in yet another embodiment, other compounds. In one embodiment, such compositions comprise from about 0.01% to about 10.0% w/v of a subject compound, more preferably from about 0.1% to about 5.0, which in another embodiment, is used for the systemic delivery of compounds by a route known to one skilled in the art.

In certain embodiments, the compositions comprise dry powders. In certain embodiments, compositions are formulated for atomization and/or inhalation administration. In certain embodiments, such compositions are contained in a container with attached atomizing means.

Further, in another embodiment, the pharmaceutical compositions are administered by intravenous, intra-arterial, or intramuscular injection of a liquid preparation. In certain embodiments, suitable liquid formulations include solutions, suspensions, dispersions, emulsions, oils and the like. In another embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

In another embodiment, the active compound is delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327).

In another embodiment, the pharmaceutical composition delivered in a controlled release system is formulated for intravenous infusion, implantable osmotic pump, transdermal patch, liposomes, or other modes of administration. In another embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used. In yet one embodiment, a controlled release system are placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In certain embodiments, the preparation of pharmaceutical compositions which contain active components is well understood in the art, for example by mixing, granulating, or tablet-forming processes. In certain embodiments, the active therapeutic ingredients are mixed with excipients which are pharmaceutically acceptable and compatible with the active ingredient. In certain embodiments, for oral administration, the compounds as described herein or their physiologically tolerated derivatives such as salts, esters, N-oxides, and the like and additional therapeutic agent or agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions.

In certain embodiments, an active component as described herein is formulated into the composition as neutralized pharmaceutically acceptable salt forms. In certain embodiments, pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. In certain embodiments, salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In certain embodiments, for use in medicine, the salts of the compounds as described herein will be pharmaceutically acceptable salts. In certain embodiments, other salts may, however, be useful in the preparation of the compounds used in the methods described herein, or of their pharmaceutically acceptable salts. In certain embodiments, suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

In certain embodiments, the compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acids and bases to adjust the pH of these aqueous compositions as needed. In certain embodiments, the compositions may also comprise local anesthetics or other actives. In certain embodiments, the compositions are used as sprays, mists, drops, and the like.

In certain embodiments, substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. In certain embodiments, the choice of a pharmaceutically-acceptable carrier to be used in conjunction with the compound is basically determined by the way the compound is to be administered. In certain embodiments, wherein the subject compound is to be injected, the preferred pharmaceutically-acceptable carrier is sterile, physiological saline, with a blood-compatible suspending agent, the pH of which has been adjusted to about 7.4.

In certain embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In certain embodiments, typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. AVICEL™, RC-591), tragacanth and sodium alginate; typical wetting agents include lecithin and polyethylene oxide sorbitan (e.g. polysorbate 80). In certain embodiments, typical preservatives include methyl paraben and sodium benzoate. In certain embodiments, peroral liquid compositions also contain one or more components such as sweeteners, flavoring agents and colorants disclosed above.

In certain embodiments, dry powder compositions may comprise propellants such as chlorofluorocarbons 12/11 and 12/114, or, in another embodiment, other fluorocarbons, non-toxic volatiles; solvents such as water, glycerol and ethanol, these include co-solvents as needed to solvate or suspend the active; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin.

In certain embodiments, the compositions also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In certain embodiments, also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In certain embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). In certain embodiments, such modifications may also increase the compounds solubility in aqueous solution, eliminate aggregation, enhance the physical and chemical stability of the compound, and greatly reduce the immunogenicity and reactivity of the compound. In certain embodiments, the desired in vivo biological activity may be achieved by the administration of such polymer-compound abducts less frequently or in lower doses than with the unmodified compound.

In certain embodiments, the compounds of the invention are administered as the sole active pharmaceutical agent, they can also be used in combination with one or more other compound as described herein, and/or in combination with other agents used in the treatment and/or prevention of diseases, disorders and/or conditions, associated with a poxvirus infection, as will be understood by one skilled in the art. In another embodiment, the compounds as described herein are administered sequentially with one or more such agents to provide sustained therapeutic and prophylactic effects. In another embodiment, the compounds may be administered via different routes, at different times, or a combination thereof. It is to be understood that any means of administering combined therapies which include the compounds of this invention are to be considered as part of this invention.

In another embodiment, the additional active agents are generally employed in therapeutic amounts as indicated in the PHYSICIANS' DESK REFERENCE (PDR) 53rd Edition (1999), which is incorporated herein by reference, or such therapeutically useful amounts as would be known to one of ordinary skill in the art. In another embodiment, the compounds of the invention and the other therapeutically active agents are administered at the recommended maximum clinical dosage or at lower doses. In certain embodiments, dosage levels of the active compounds in the compositions of the invention may be varied to obtain a desired therapeutic response depending on the route of administration, severity of the disease and the response of the patient. In another embodiment, the combination is administered as separate compositions or in other embodiments as a single dosage form containing both agents. In certain embodiments, when administered as a combination, the therapeutic agents is formulated, in another embodiment, as separate compositions that are given at the same time or different times, or in other embodiments the therapeutic agents are given as a single composition.

In certain embodiments, the compositions and methods described herein are employed in the treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value.

The following examples are presented in order to more fully illustrate the preferred embodiments of the invention. They should in no way be construed, however, as limiting the broad scope of the invention.

EXAMPLES

The compounds of the present invention that are used to inhibit, treat, or abrogate a poxvirus infection in a subject are prepared as shown in the following examples.

All compound syntheses were carried out at Organix Inc. (Woburn, Mass.). All solvents and reagents were used as obtained. Air and moisture sensitive reactions were carried out in oven-dried glassware sealed with rubber septa under a positive pressure of dry $N_2$. Reactions were stirred using Teflon-coated magnetic stir bars. Elevated temperatures were maintained using Thermostat controlled silicone oil baths. Organic solutions were concentrated using a rotary evaporator with a diaphragm vacuum pump. Melting points were obtained on a MeI-Temp apparatus and are uncorrected. Proton NMR spectra were recorded on a Jeol Eclipse 300 and expressed in δ (ppm) with TMS as an internal standard. HPLC and MS data were obtained on an Agilent 1100 Series LC/MS system. Thin layer chromatography (TLC) was carried out on Baker Si 250 F plates. Flash chromatography was carried out on Baker Silica Gel 40 µM or ISCO columns packed with 230-400 mesh and pore size 60 Å silica gel. Purity in two solvent systems ($H_2O$—$CH_3CN$ or $H_2O$-MeOH) was determined using an Agilent 1100 HPLC instrument, and all final compounds were >95% pure. Elemental analyses were carried out by Atlantic Microlab (Norcross, Ga.).

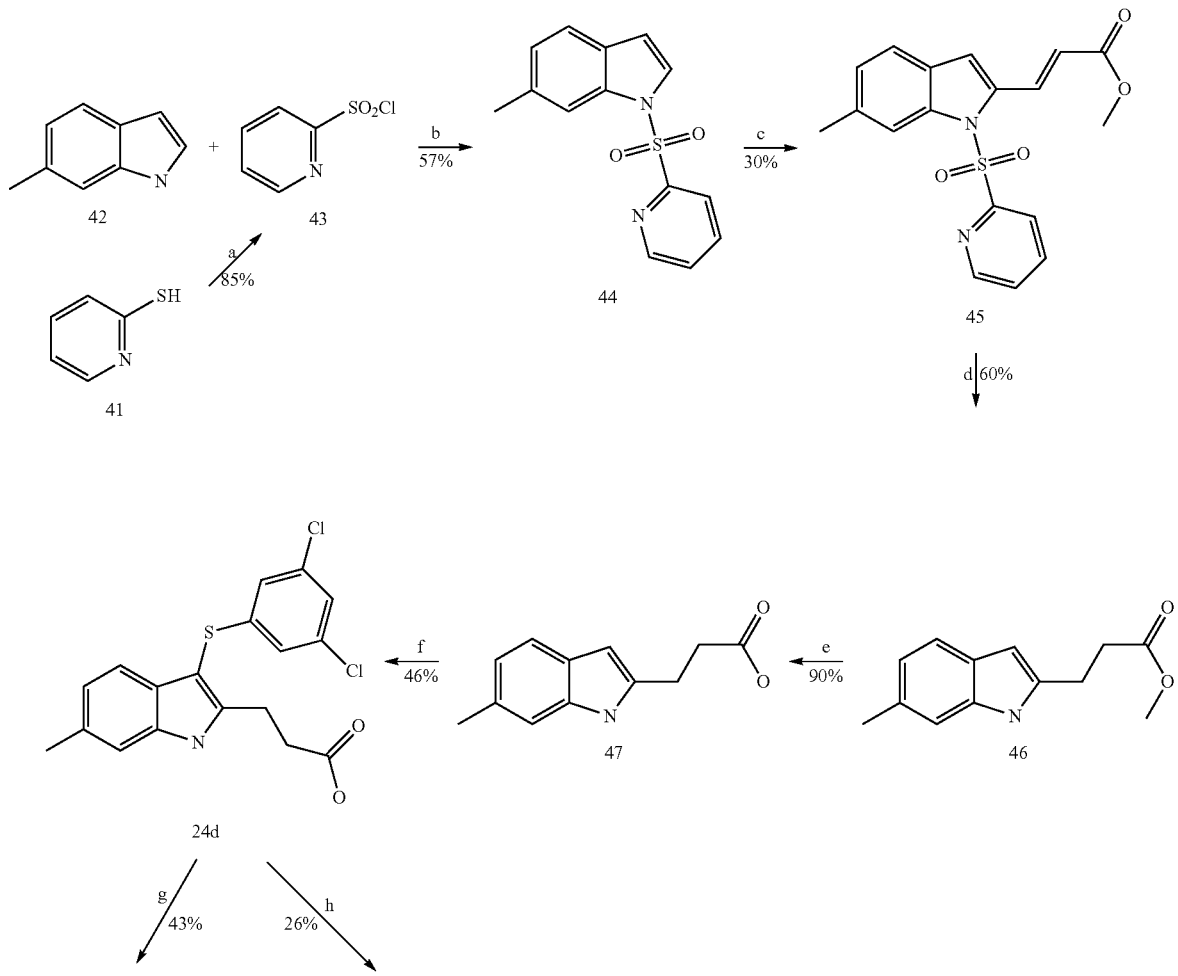

Scheme 1. Preparation of the acid analog 24d and the alkylamides 24a and 24e[a]

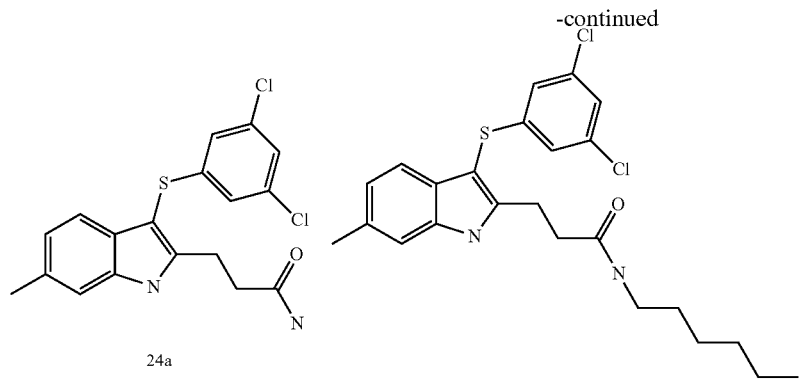
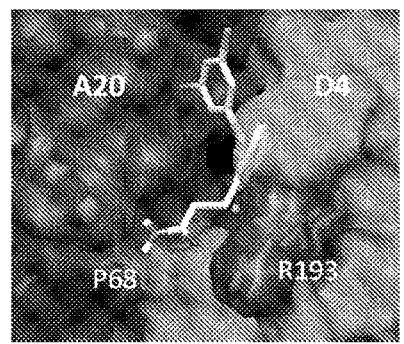

*Reagents and conditions: (a) HCl, H₂O, Cl₂, 0° C.; (b) NaH, THF, 0° C. to rt; (c) PdCl₂(MeCN)₂, Cu(OAc)₂, H₂O, methyl acrylate, MeCN, 110° C. to rt; (d) Mg, MeOH, 0° C.; (e) LiOH, (1:1:1) THF, MeOH, H₂O, rt; (f) NaH, DMF, 3,3′,5,5′-tetrachlorodiphenyl disulfide, 0° C., 50° C., rt; (g) oxalyl chloride, CH₂Cl₂, DMF, then aq NH₃, 0° C. to rt; (h) oxalyl chloride, CH₂Cl₂, DMF, then aq NH₃, 0° C. to rt; (h) oxalyl chloride, CH₂Cl₂, DMF, then n-hexylamine, CH₂Cl₂, Et₃N, 0° C. to rt. (Inset) Docked post of 24a.

Example 1

Pyridine-2-sulfonyl chloride (43)

A solution of 2-mercaptopyridine (41) (20.0 g, 180.0 mmol) in 140 mL of conc. HCl and 20 mL of water was cooled to 0° C. Cl$_2$ was bubbled through this solution for 2 h. A stream of N$_2$ was then used to remove excess Cl$_2$. The mixture was poured onto ice-water and dichloromethane was added. The reaction mixture was neutralized with solid NaHCO$_3$ while maintaining the temperature at 0° C. by addition of ice. Two phases were separated and the aqueous layer was extracted with cold dichloromethane. The organics were dried over MgSO$_4$, and concentrated in vacuo to provide 27.2 g (85%) of product 43 as a colorless oil which was used immediately. $^1$H NMR (300 MHz, CDCl$_3$) δ 7.68-7.70 (m, 1H), 8.05-8.10 (m, 2H), 8.82-8.83 (m, 3H).

Example 2

6-Methyl-1-(pyridin-2-ylsulfonyl)-1H-indole (44)

6-Methylindole (42) (7.34 g, 56.0 mmol) was added in portions to a mixture of sodium hydride (3.36 g, 84.0 mmol) in THF (80 mL) at 0° C. After 15 min, pyridine-2-sulfonyl chloride (43) (10.0 g, 56.0 mmol) was added, and the reaction was allowed to warm to rt and stirred overnight under N$_2$. The reaction mixture was then quenched with ice water and extracted with EtOAc. The organic layers were combined, dried over MgSO$_4$, and concentrated in vacuo. The crude product was purified by flash column chromatography eluting with a linear gradient ranging from 0 to 40% EtOAc-hexanes to provide 8.8 g (57%) of product 44 as a brown gum. $^1$H NMR (300 MHz, CDCl$_3$) δ 2.44 (s, 3H), 6.62 (dd, J=1, 4 Hz, 1H), 7.03-7.06 (m, 1H), 7.41 (d, J=8 Hz, 1H), 7.41-7.45 (m, 1H), 7.59 (d, J=4 Hz, 1H), 7.79-7.81 (m, 1H), 7.84-7.90 (m, 1H), 8.10 (dt, J=1, 8 Hz, 1H), 8.58-8.60 (m, 1H). LC-MS (CI): m/z 273.0 [(M+H)$^+$ C$_{14}$H$_{12}$N$_2$O$_2$S requires 272.06].

Example 3

Methyl 3-(6-methyl-1-(pyridin-2-ylsulfonyl)-1H-indol-2-yl)acrylate (45)

In a sealed tube, 44 (9.60 g, 35.2 mmol), copper (II) acetate monohydrate (14.05 g, 70.4 mmol), and PdCl$_2$(CH$_3$CN)$_2$ (0.91 g, 3.5 mmol) were placed under a nitrogen atmosphere. Acetonitrile (60 mL) was added followed by methyl acrylate (9.52 mL, 105.6 mmol). The mixture was heated at 110° C. for 20 h, allowed to reach rt, diluted with EtOAc, and washed with water and brine. The combined organic layers were dried over MgSO$_4$, and concentrated in vacuo. The crude product was purified by flash column chromatography eluting with a linear gradient ranging from 0 to 20% EtOAc-hexanes to provide 3.86 g (30%) of product 45 as a pale yellow solid. $^1$H NMR (300 MHz, CDCl$_3$) δ 2.46 (s, 3H), 3.81 (s, 3H), 6.39 (d, J=16 Hz, 1H), 6.97 (s, 1H), 7.06-7.08 (m, 1H), 7.39 (d, J=8 Hz, 1H), 7.40-7.45 (m, 1H), 7.84-7.90 (m, 1H), 7.94-7.96 (m, 1H), 8.06 (dt, J=1, 8 Hz, 1H), 8.42 (d, J=16 Hz, 1H), 8.52-8.54 (m, 1H). LC-MS (CI): m/z 357.1 [(M+H)$^+$ C$_{18}$H$_{16}$N$_2$O$_4$S requires 356.08].

Example 4

Methyl 3-(6-methyl-1H-indol-2-yl)propanoate (46)

A suspension of 45 (1.86 g, 5.22 mmol) and Mg (2.54 g, 104.4 mmol) in MeOH (40 mL) was stirred at 0° C. for 2 h. The mixture was diluted with EtOAc and filtered through a pad of Celite. The filtrate was washed with a sat. NaHCO$_3$ solution, brine, dried over MgSO$_4$, and concentrated in vacuo. The residue was purified by flash column chromatography eluting with a linear gradient ranging from 0 to 10% EtOAc-hexanes to provide 0.69 g (60%) of product 46 as a pale yellow solid. $^1$H NMR (300 MHz, CDCl$_3$) δ 2.43 (s, 3H), 2.74 (t, J=7 Hz, 2H), 3.06 (t, J=7 Hz, 2H), 3.71 (s, 3H), 6.17 (m, 1H), 6.90 (d, J=8 Hz, 1H), 7.10 (s, 1H), 7.40 (d, J=8 Hz, 1H), 8.36 (brs, 1H). LC-MS (CI): m/z 218.1 [(M+H)$^+$ C$_{13}$H$_{15}$NO$_2$ requires 217.11].

Example 5

3-(6-Methyl-1H-indol-2-yl)propanoic acid (47)

To a solution of 46 (0.69 g, 3.17 mmol) in THF:MeOH:H$_2$O (1:1:1) (9 mL) was added LiOH.H$_2$O (0.25 g, 5.96 mmol). The reaction was stirred at rt for 16 h, diluted with water, acidified to pH 3 with 1 N HCl, and extracted with EtOAc. The combined organic layers were washed with water, brine, dried over MgSO$_4$, and concentrated in vacuo to provide 0.58 g (90%) of product 47 as an off-white solid. $^1$H NMR (300 MHz, DMSO-d$_6$) δ 2.35 (s, 3H), 2.65 (t, J=8 Hz, 2H), 2.93 (t, J=8 Hz, 2H), 6.05 (s, 1H), 6.75 (d, J=8 Hz, 1H), 7.04 (s, 1H), 7.27 (d, J=8 Hz, 1H), 10.74 (brs, 1H), 12.19 (brs, 1H). LC-MS (CI): m/z 202.0 [(M−H)$^-$ C$_{12}$H$_{13}$NO$_2$ requires 203.09].

Example 6

3-(3-((3,5-Dichlorophenyl)thio)-6-methyl-1H-indol-2-yl)propanoic acid (24d)

Following the method used to prepare 1, the use of 47 (0.58 g, 2.85 mmol) and 54 (1.52 g, 4.27 mmol) provided 0.50 g (46%) of product 24d as a pale yellow solid, mp 162-164° C. $^1$H NMR (300 MHz, CDCl$_3$) δ 2.45 (s, 3H), 2.75 (t, J=6 Hz, 2H), 3.18 (t, J=6 Hz, 2H), 6.84 (s, 1H), 6.83 (s, 1H) 6.97-7.01 (m, 2H), 7.18 (s, 1H), 7.38 (d, J=8 Hz, 1H), 8.90 (s, 1H). LC-MS (CI): m/z 377.9, 379.9 [(M−H)$^-$ C$_{18}$H$_{15}$Cl$_2$NO$_2$S requires 379.02]. Purity (100%). Calcd for C$_{18}$H$_{15}$Cl$_2$NO$_2$S.0.07C$_6$H$_{14}$: C, 57.27; H, 4.17; N, 3.63; S, 8.30; Cl, 18.35. Found: C, 57.26; H, 4.05; N, 3.69; S, 7.96; Cl, 18.04.

Example 7

3-(3-((3,5-Dichlorophenyl)thio)-6-methyl-1H-indol-2-yl)propanamide (24a)

To a 0° C. solution of 24d (200 mg, 0.52 mmol) in CH$_2$Cl$_2$ (4 mL) was added oxalyl chloride (66 µL, 0.79 mmol) followed by a drop of DMF. The mixture was stirred for 2 h at 0° C. under N$_2$. The solvent was removed in vacuo and CH$_2$Cl$_2$ (1 mL) was added. The solvent was again removed and dried in vacuo to provide the intermediate acid chloride as a brown gum. To a 0° C. solution of this acid chloride in dioxane (1 mL) was added aqueous ammonia (2 mL). The reaction was allowed to warm to rt and stirred for 2 h, and then was extracted with EtOAc. The combined organics were washed with brine, dried over MgSO$_4$, and concentrated in vacuo. The crude product was purified by flash column chromatography eluting with a linear gradient ranging from 0 to 100% EtOAc-hexanes to provide 83 mg (43%) of product 24a as an off-white solid, mp 152° C. $^1$H NMR (300 MHz, CDCl$_3$) δ 2.46 (s, 3H), 2.53-2.57 (m, 2H), 3.15-3.19 (m, 2H), 5.41 (brs, 2H), 6.83-6.84 (m, 2H), 6.99 (d, J=8 Hz, 1H), 7.00-7.02 (m, 1H), 7.19 (s, 1H), 7.38 (d, J=8 Hz, 1H), 9.61 (s, 1H). LC-MS (CI): m/z 379.0, 381.0 [(M+H)$^+$ C$_{18}$H$_{16}$Cl$_2$N$_2$OS requires 378.04]. Purity (100%). Calcd for C$_{18}$H$_{16}$Cl$_2$N$_2$OS: C, 57.00; H, 4.25; N, 7.39; S, 8.45; Cl, 18.69. Found: C, 56.77; H, 4.46; N, 7.22; S, 8.65; Cl, 18.88.

Example 8

3-(3-((3,5-Dichlorophenyl)thio)-6-methyl-1H-indol-2-yl)-N-hexylpropanamide (24e)

Following the method used to prepare 24a, the use of 24d (0.22 g, 0.59 mmol) and oxalyl chloride (100 µL, 1.18 mmol) followed by allowing the intermediate acid chloride to react with n-hexylamine (0.15 mL, 1.18 mmol) in presence of Et$_3$N (0.16 mL, 1.18 mmol) provided 70 mg (26%) of product 24e as a yellow gum. $^1$H NMR (300 MHz, CDCl$_3$) δ 0.86 (t, J=7 Hz, 3H), 1.20-1.31 (m, 6H), 1.40-1.51 (m, 2H), 2.45 (s, 3H), 2.43-2.49 (m, 2H), 3.14-3.18 (m, 2H), 3.22-3.29 (m, 2H), 5.45 (brs, 1H), 6.82-6.84 (m, 2H), 6.97 (d, J=8 Hz, 1H), 6.98-7.01 (m, 1H), 7.18 (brs, 1H), 7.38 (d, J=8 Hz, 1H), 9.91 (s, 1H). LC-MS (CI): m/z 463.1, 465.1 [(M+H)$^+$ C$_{24}$H$_{28}$Cl$_2$N$_2$OS requires 463.13]. Purity (100%). Calcd for C$_{24}$H$_{28}$Cl$_2$N$_2$O$_2$S.0.06C$_6$H$_{14}$: C, 62.43; H, 6.20; N, 5.98; Cl, 15.13. Found: C, 62.72; H, 6.01; N, 6.01; Cl, 15.17.

Scheme 2. Preparation of the alkylamides 24d and 24c$^a$

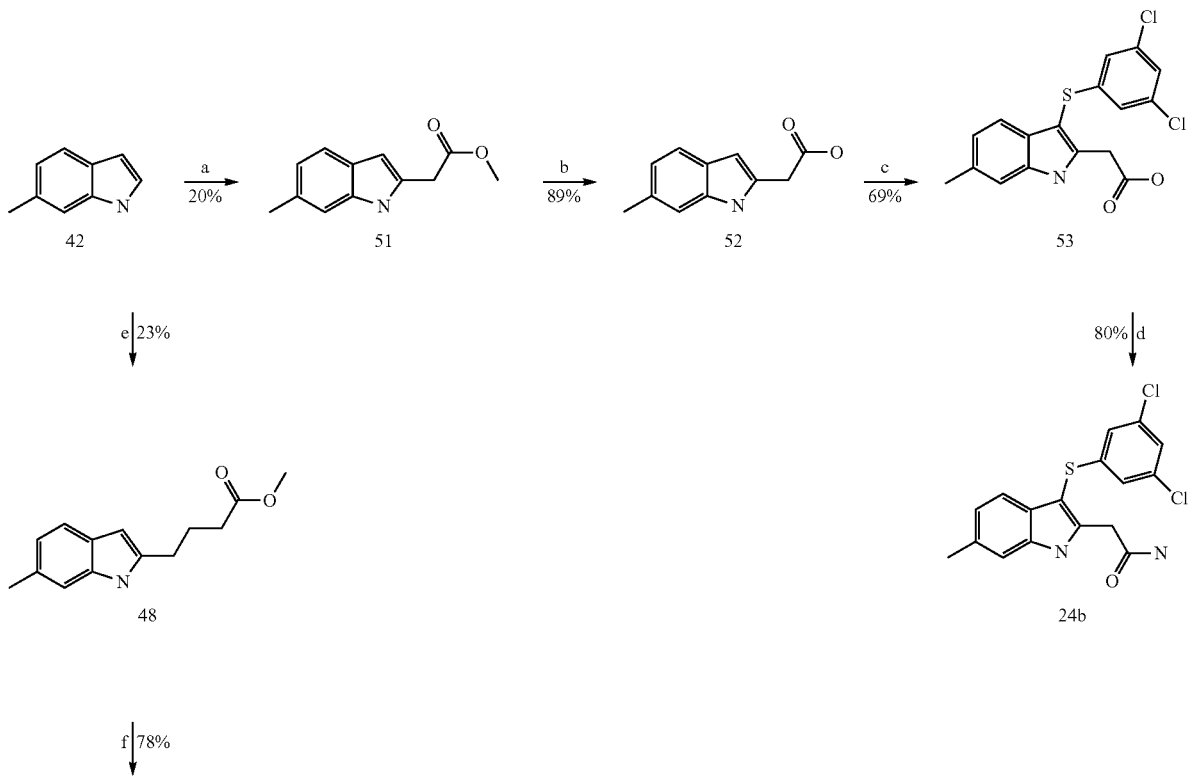

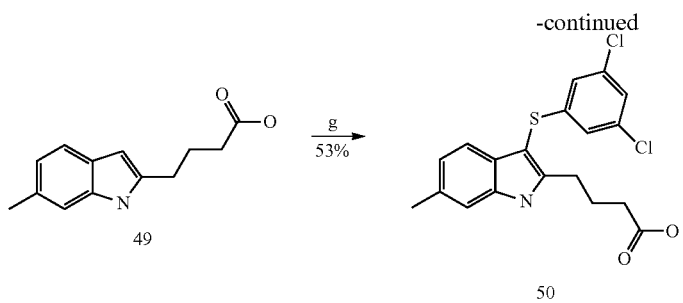
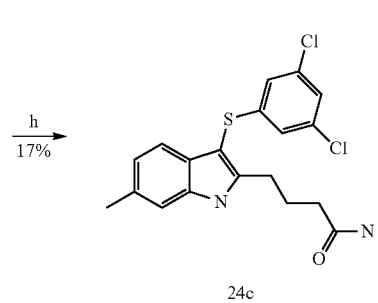

*Reagents and conditions: (a) PdCl$_2$(MeCN)$_2$, norbornene, K$_2$CO$_3$, then methyl bromoacetate, DMA-H$_2$O, 70° C., rt, 60° C.; (b) LiOH, (1:1:1) THF, MeOH, H$_2$O, rt; (c) NaH, DMF, 3,3',5,5'-tetrachlorodiphenyl sulfide, 0° C., 50° C., rt; (d) oxalyl chloride, CH$_2$Cl$_2$, DMF, then NH$_3$ in dioxane, 0° C. to rt: (e) PdCl$_2$(MeCN)$_2$, norbornene, K$_2$CO$_3$, methyl 4-bromobutyrate, DMA-H$_2$O, 70° C., rt, 60° C.; (f) LiOH, (1:1:1) THF, MeOH, H$_2$O, rt; (g) NaH, DMF, 3,3',5,5'-tetrachlorodiphenyl disulfide, 0° C., 50° C., rt; (h) oxalyl chloride, CH$_2$Cl$_2$, DMF, then aq NH$_3$, 0° C. to rt.

Example 9

Methyl 4-(6-methyl-1H-indol-2-yl)butanoate (48)

A round bottom flask was charged with 42 (1.76 g, 13.4 mmol), norbornene (2.53 g, 26.9 mmol), K$_2$CO$_3$ (3.71 g, 26.9 mmol), and PdCl$_2$(CH$_3$CN)$_2$ (0.35 g, 1.34 mmol). A solution of water in DMA (0.5 M, 10 mL) was then added. The reaction mixture was evacuated, back filled with argon three times, and then added with methyl 4-bromobutyrate (4.7 mL, 26.0 mmol). The reaction mixture was placed in a preheated oil bath at 70° C., and the mixture was stirred vigorously for 16 h under N$_2$. The reaction was cooled to rt, diluted with ether, and filtered. The filtrate was concentrated in vacuo at 60° C. to remove ether and most of DMA. The residue was purified by flash column chromatography eluting with a linear gradient ranging from 0 to 40% EtOAc-hexanes to provide 0.72 g (23%) of product 48 as an off-white solid. $^1$H NMR (300 MHz, CDCl$_3$) δ 1.98-2.07 (m, 2H), 2.40 (t, J=7 Hz, 2H), 2.43 (s, 3H), 2.80 (t, J=7 Hz, 1H), 3.66 (s, 3H), 6.18-6.19 (m, 1H), 6.91 (d, J=8 Hz, 1H), 7.09 (s, 1H), 7.40 (d, J=8 Hz, 1H), 7.90 (brs, 1H). LC-MS (CI): m/z 232.1 [(M+H)$^+$ C$_{14}$H$_{17}$NO$_2$ requires 231.13].

Example 10

4-(6-Methyl-1H-indol-2-yl)butanoic acid (49)

Following the method used to prepare 47, the use of 48 (0.71 g, 3.07 mmol) provided 0.52 g (78%) of product 49 as a pale yellow solid. $^1$H NMR (300 MHz, CDCl$_3$) δ 1.99-2.08 (m, 2H), 2.40-2.45 (m, 2H), 2.43 (s, 3H), 2.83 (t, J=7 Hz, 2H), 6.20 (s, 1H), 6.91 (d, J=8 Hz, 1H), 7.09 (s, 1H), 7.41 (d, J=8 Hz, 1H), 7.82 (brs, 1H). LC-MS (CI): m/z 216.1 [(M–H)$^-$ C$_{13}$H$_{15}$NO$_2$ requires 217.11].

Example 11

4-(3-((3,5-Dichlorophenyl)thio)-6-methyl-1H-indol-2-yl)butanoic acid (50)

Following the method used to prepare 1, the use of 49 (0.50 g, 2.30 mmol) and 54 (1.23 g, 3.45 mmol) yielded a crude product that was purified by flash column chromatography by elution with a linear gradient ranging from 0 to 100% EtOAc-hexanes to provide 0.48 g (53%) of product 50 as a brown foam. $^1$H NMR (300 MHz, CDCl$_3$) δ 1.93-2.02 (m, 2H), 2.36 (t, J=7 Hz, 2H), 2.45 (s, 3H), 2.87-2.93 (m, 2H), 6.83-6.84 (m, 2H), 6.95-6.99 (m, 2H), 7.18 (s, 1H), 7.37 (d, J=8 Hz, 1H), 8.97 (brs, 1H). LC-MS (CI): m/z 392.0, 393.9 [(M+H)$^+$ C$_{19}$H$_{17}$Cl$_2$NO$_2$S requires 394.04].

Example 12

4-(3-((3,5-Dichlorophenyl)thio)-6-methyl-1H-indol-2-yl)butanamide (24c)

Following the method used to prepare 24a, the use of 50 (135 mg, 0.34 mmol) and oxalyl chloride (43 μL, 0.51 mmol) followed by reacting the intermediate acid chloride with aqueous ammonia (2 mL) provided 23 mg (17%) of product 24c as a pale yellow solid, mp 163-164° C. $^1$H NMR (300 MHz, CDCl$_3$) δ 1.92-2.01 (q, J=7 Hz, 2H), 2.25 (t, J=7 Hz, 2H), 2.46 (s, 3H), 2.96 (t, J=7 Hz, 2H), 5.42 (brs, 2H), 6.84 (d, J=2 Hz, 2H), 6.96-7.00 (m, 2H), 7.21 (s, 1H), 7.38 (d, J=8 Hz, 1H), 9.34 (brs, 1H). LC-MS (CI): m/z 393.0, 395.0 [(M+H)$^+$ C$_{19}$H$_{18}$Cl$_2$N$_2$OS requires 392.05]. Purity (100%). Calcd for C$_{19}$H$_{18}$Cl$_2$N$_2$OS: C, 58.02; H, 4.61; N, 7.12; S, 8.15; Cl, 18.03. Found: C, 58.06; H, 4.79; N, 6.88; S, 7.90; Cl, 17.75. The low yield for amide preparation in this case was due to the significant formation of a six membered lactam via cyclization of the intermediate acid chloride.

Example 13

Methyl 2-(6-methyl-1H-indol-2-yl)acetate (51)

Following the method used to prepare 48, the use of 42 (2.5 g, 19.0 mmol) and methyl bromoacetate at 40° C. for 16 h provided 0.79 g (20%) of product 51 as a pale yellow solid. $^1$H NMR (300 MHz, DMSO-d$_6$) δ 2.36 (s, 3H), 3.64 (s, 3H), 3.81 (s, 2H), 6.19 (s, 1H), 6.79 (d, J=8 Hz, 1H), 7.10 (s, 1H), 7.32 (d, J=8 Hz, 1H), 10.86 (brs, 1H). LC-MS (CI): m/z 204.1 [(M+H)$^+$ C$_{12}$H$_{13}$NO$_2$ requires 203.09].

Example 14

2-(6-Methyl-1H-indol-2-yl)acetic acid (52)

Following the method used to prepare 47, the use of 51 (0.76 g, 3.74 mmol) provided 0.63 g (89%) of product 52 as a pale brown solid. $^1$H NMR (300 MHz, DMSO-d$_6$) δ 2.35 (s, 3H), 3.68 (s, 2H), 6.16 (s, 1H), 6.78 (d, J=8 Hz, 1H), 7.09 (s, 1H), 7.31 (d, J=8 Hz, 1H), 10.81 (brs, 1H), 12.46 (brs, 1H). LC-MS (CI): m/z 188.0 [(M–H)$^-$ C$_{11}$H$_{11}$NO$_2$ requires 189.08].

Example 15

2-(3-((3,5-Dichlorophenyl)thio)-6-methyl-1H-indol-2-yl)acetic acid (53)

Following the method used to prepare 1, the use of 52 (0.56 g, 2.96 mmol) and 54 (1.05 g, 2.95 mmol) at rt for 1d provided 0.75 g (69%) of product 53 as a light brown solid. $^1$H NMR (300 MHz, CDCl$_3$) δ 2.47 (s, 3H), 4.02 (s, 2H), 6.86 (d, J=2 Hz, 2H), 7.91-7.03 (m, 2H), 7.22 (brs, 1H), 7.42 (d, J=8 Hz, 1H), 8.95 (brs, 1H). LC-MS (CI): m/z 363.8, 365.8 [(M+H)$^+$ C$_{17}$H$_{13}$Cl$_2$NO$_2$S requires 365.0].

Example 16

2-(3-((3,5-Dichlorophenyl)thio)-6-methyl-1H-indol-2-yl)acetamide (24b)

Following the method used to prepare 24a, the use of 53 (0.35 g, 0.96 mmol) and oxalyl chloride (120 μL, 1.44 mmol) followed by allowing the intermediate acid chloride to react with ammonia in dioxane provided 0.28 g (80%) of product 24b as an off white solid, mp 197° C. $^1$H NMR (300 MHz, DMSO-d$_6$) δ 2.40 (s, 3H), 3.70 (s, 2H), 6.90 (d, J=8 Hz, 1H), 6.99-7.01 (m, 2H), 7.08 (brs, 1H), 7.20 (d, J=8 Hz, 1H), 7.25-7.28 (m, 2H), 7.54 (brs, 1H), 11.65 (brs, 1H). LC-MS (CI): m/z 365.0, 367.0 [(M+H)$^+$ C$_{17}$H$_{14}$Cl$_2$NO$_2$S requires 364.0]. Purity (100%). Calcd for C$_{17}$H$_{14}$Cl$_2$NO$_2$S: C, 55.90; H, 3.86; N, 7.67; S, 8.78; Cl, 19.41. Found: C, 55.61; H, 3.90; N, 7.68; S, 8.59; Cl, 19.67.

Example 17

3-((4-Chlorophenyl)thio)-6-methyl-1H-indole-2-carboxylic acid (1)

6-Methyl-1H-indole-2-carboxylic acid (0.30 g, 1.71 mmol) was dissolved in DMF (5 mL) and the mixture was cooled to 0° C. Sodium hydride (0.20 g, 5.13 mmol) was added and the reaction mixture was stirred for 15 min Bis(4-chlorophenyl)disulfide (26) (0.59 g, 2.05 mmol) to was added to this solution and the reaction was heated at 50° C. for 1d under N$_2$. The reaction was allowed to cool to rt, quenched with ice-water, acidified to pH 3 with 1 N HCl, and extracted into EtOAc. The organic layers were combined, washed with water and brine, dried over MgSO$_4$, and concentrated in vacuo. The crude product was purified by flash column chromatography eluting with a linear gradient ranging from 0 to 10% MeOH—CH$_2$Cl$_2$ to provide 0.28 g (52%) of product 1 as an off white solid, mp 228-229° C. $^1$H NMR (300 MHz, DMSO-d$_6$) δ 2.39 (s, 3H), 6.95 (d, J=9 Hz, 1H), 7.03 (d, J=9 Hz, 2H), 7.27 (d, J=9 Hz, 2H), 7.24-7.29 (m, 2H), 12.20 (s, 1H), 13.30 (s, 1H). LC-MS (CI): m/z 316.0 [(M–H)$^-$ C$_{16}$H$_{12}$ClNO$_2$S requires 317.03]. Calcd for C$_{16}$H$_{12}$ClNO$_2$S: C, 60.47; H, 3.81; N, 4.41; S, 10.09; Cl, 11.16. Found: C, 60.49; H, 3.84; N, 4.38; S, 10.36; Cl, 11.05.

Example 18

3-((4-Chlorophenyl)thio)-4-methyl-1H-indole-2-carboxylic acid (1a)

Following the method used to prepare 1, the use of 4-methyl-1H-indole-2-carboxylic acid (27) (0.5 g, 2.85 mmol) and 26 (0.86 g, 2.99 mmol) provided 0.39 g of product 1a (43%) as an off white solid, mp 223-224° C. $^1$H NMR (300 MHz, DMSO-d$_6$) δ 2.56 (s, 3H), 6.85 (d, J=7 Hz, 1H), 6.92-6.97 (m, 2H), 7.18 (t, J=7 Hz, 1H), 7.24-7.30 (m, 2H), 7.40 (d, J=8 Hz, 1H), 12.40 (s, 1H), 13.35 (s, 1H). LC-MS (CI): m/z 316.0 [(M–H)$^-$ C$_{16}$H$_{12}$Cl NO$_2$S requires 317.03]. Purity (100%). Calcd for C$_{16}$H$_{12}$Cl NO$_2$S: C, 60.47; H, 3.81; N, 4.41; S, 10.09; Cl, 11.16. Found: C, 60.30; H, 3.68; N, 4.37; S, 10.28; Cl, 11.43.

Example 19

3-((4-Chlorophenyl)thio)-5-methyl-1H-indole-2-carboxylic acid (1b)

Following the method used to prepare 1, the use of 5-methyl-1H-indole-2-carboxylic acid (28) (1.0 g, 5.70 mmol) and 26 (1.72 g, 6.0 mmol) provided 0.96 g of product 1b (53%) as an off white solid, mp 226-227° C. $^1$H NMR (300 MHz, DMSO-d$_6$) δ 2.39 (s, 3H), 7.00 (d, J=9 Hz, 2H), 7.16 (d, J=8 Hz, 1H), 7.21-7.28 (m, 3H), 7.43 (d, J=8 Hz, 1H), 12.27 (s, 1H), 13.32 (s, 1H). LC-MS (CI): m/z 316.0 [(M–H)$^-$ C$_{16}$H$_{12}$Cl NO$_2$S requires 317.03]. Purity (100%). Calcd for C$_{16}$H$_{12}$Cl NO$_2$S: C, 60.47; H, 3.81; N, 4.41; S, 10.09; Cl, 11.16. Found: C, 60.22; H, 3.66; N, 4.35; S, 10.00; Cl, 11.34.

Example 20

3-((4-Chlorophenyl)thio)-7-methyl-1H-indole-2-carboxylic acid (1c)

Following the method used to prepare 1, the use of 7-methyl-1H-indole-2-carboxylic acid (29) (0.3 g, 1.71 mmol) and 26 (0.59 g, 2.05 mmol) provided 0.28 g of product 1c (51%) as an off white solid, mp 225-229° C. $^1$H NMR (300 MHz, DMSO-d$_6$) δ 2.55 (s, 3H), 6.99-7.03 (m, 3H), 7.11 (d, J=7 Hz, 1H), 7.23-7.28 (m, 3H), 12.17 (s, 1H), 13.40 (s, 1H). LC-MS (CI): m/z 316.0 [(M–H)$^-$ C$_{16}$H$_{12}$ClNO$_2$S requires 317.03]. Purity (98%). Calcd for C$_{16}$H$_{12}$ClNO$_2$S.0.2H$_2$O: C, 59.79; H, 3.89; N, 4.36; S, 9.98; Cl, 11.03. Found: C, 59.89; H, 3.77; N, 4.56; S, 9.92; Cl, 10.83.

Example 21

3-(4-Chlorophenylthio)-1H-indole-2-carboxylic acid (1d)

Following the method used to prepare 1, the use of indole-2-carboxylic acid (30) (0.15 g, 0.93 mmol) and 26 (0.32 g, 1.11 mmol) provided 0.21 g of product 1d (74%) as a white solid, mp 225° C. $^1$H NMR (300 MHz, DMSO-d$_6$) δ 7.03-7.13 (m, 3H), 7.24-7.34 (m, 3H), 7.43 (d, J=8 Hz, 1H), 7.53 (d, J=8 Hz, 1H), 12.36 (s, 1H), 13.40 (s, 1H). LC-MS (CI): m/z 302.0 [(M–H)$^-$ C$_{15}$H$_{10}$ClNO$_2$S requires 303.02]. Purity (98%). Calcd for C$_{15}$H$_{10}$ClNO$_2$S: C, 59.31; H, 3.32; N, 4.61; S, 10.56; Cl, 11.67. Found: C, 59.40; H, 3.21; N, 4.54; S, 10.38; Cl, 11.54.

Example 22

6-Chloro-3-((4-chlorophenyl)thio)-1H-indole-2-carboxylic acid (1e)

Following the method used to prepare 1, the use of 6-chloro-1H-indole-2-carboxylic acid (31) (0.12 g, 0.61 mmol) and 26 (0.21 g, 0.74 mmol) provided 0.12 g of product 1e (58%) as a brown solid, mp 232-233° C. $^1$H NMR (300 MHz, DMSO-d$_6$) δ 7.06 (d, J=9 Hz, 2H), 7.12-7.15 (m, 1H), 7.25-7.29 (m, 2H), 7.42 (d, J=9 Hz, 1H), 7.52 (s, 1H), 12.48 (s, 1H), 13.58 (s, 1H). LC-MS (CI): m/z 335.9 [(M–H)$^-$ $C_{15}H_9Cl_2NO_2S$ requires 336.97]. Purity (100%). Calcd for $C_{15}H_9Cl_2NO_2S \cdot 0.3H_2O$: C, 52.43; H, 2.82; N, 4.08; S, 9.33; Cl, 20.64. Found: C, 52.58; H, 2.58; N, 4.11; S, 9.69; Cl, 20.34.

Example 23

6-Bromo-3-((4-chlorophenyl)thio)-1H-indole-2-carboxylic acid (1f)

Following the method used to prepare 1, the use of 6-bromo-1H-indole-2-carboxylic acid (32) (0.15 g, 0.62 mmol) and 26 (0.21 g, 0.74 mmol) provided 0.075 g of 7 (31%) as a brown solid, mp 248-249° C. $^1$H NMR (300 MHz, DMSO-$d_6$) δ 7.01-7.07 (m, 2H), 7.22-7.30 (m, 3H), 7.33-7.35 (m, 1H), 7.67 (s, 1H), 12.48 (s, 1H), 13.58 (s, 1H). LC-MS (CI): m/z 381.9 [(M−H)$^−$ $C_{15}H_9BrClNO_2S$ requires 380.92]. Purity (100%). Calcd for $C_{15}H_9BrClNO_2S$: C, 47.08; H, 2.37; N, 3.66; S, 8.38; Cl, 9.26; Br, 20.88. Found: C, 47.02; H, 2.26; N, 3.75; S, 8.41; Cl, 9.15; Br, 20.72.

Example 24

6-Fluoro-3-((4-chlorophenyl)thio)-1H-indole-2-carboxylic acid (1g)

Following the method used to prepare 1, the use of 6-fluoro-1H-indole-2-carboxylic acid (33) (0.3 g, 1.67 mmol) and 26 (0.57 g, 2.0 mmol) provided 0.19 g of product 1g (34%) as an impure off white solid that could not be readily purified. It was therefore converted to the corresponding methyl ester 34 as described below. Following the method used to prepare 47, the use of 34 (145 mg, 0.43 mmol) provided 109 mg (80%) of product 1g as an off white solid, mp 230-232° C. $^1$H NMR (300 MHz, DMSO-$d_6$) δ 6.96-7.09 (m, 3H), 7.20-7.30 (m, 3H), 7.43 (dd, J=5, 9 Hz, 1H), 12.40 (s, 1H), 13.48 (s, 1H). LC-MS (CI): m/z 320.0 [(M−H)$^−$ $C_{15}H_9ClFNO_2S$ requires 321.0]. Purity (100%). Calcd for $C_{15}H_9ClFNO_2S$: C, 55.99; H, 2.82; N, 4.35; S, 9.97; Cl, 11.02; F, 5.90. Found: C, 56.17; H, 3.05; N, 4.16; S, 9.62; Cl, 10.73; F, 5.58.

Example 25

3-((4-Chlorophenyl)thio)-6-ethyl-1H-indole-2-carboxylic acid (1h)

To a solution of freshly made sodium methoxide (prepared by dissolving Na (0.92 g, 40 mmol) in methanol (12 mL)) was added to a solution of methyl 2-azidoacetate (4.5 g, 39 mmol) and 4-ethyl benzaldehyde (35) (1.30 g, 9.7 mmol) in methanol (10 mL) at −10° C. The mixture was stirred for 2 h, maintaining the temperature below 5° C. and then was poured onto ice, extracted with dichloromethane, dried over MgSO$_4$, and concentrated by passing a stream of nitrogen to provide 1.05 g (46%) of product 1 h as a yellow gum. $^1$H NMR (300 MHz, CDCl$_3$) δ 1.20-1.25 (m, 3H), 2.64-2.66 (m, 2H), 3.88 (s, 3H), 6.91 (s, 1H), 7.18-7.21 (m, 2H), 7.71-7.73 (m, 2H).

Example 26

6-Ethyl-1H-indole-2-carboxylic acid (38)

Following the method used to prepare 47, the use of 37 (0.52 g, 2.56 mmol) provided 0.45 g (92%) of product 38 as a pale yellow solid. $^1$H NMR (300 MHz, DMSO-$d_6$) $^1$H NMR (300 MHz, CDCl$_3$) δ 1.20 (t, J=7 Hz, 3H), 2.66 (q, J=7 Hz, 2H), 6.94 (d, J=8 Hz, 1H), 7.01-7.03 (m, 1H), 7.22 (s, 1H), 7.54 (d, J=8 Hz, 1H), 11.61 (s, 1H), 12.83 (s, 1H). LC-MS (CI): m/z 188.0 [(M−H)$^−$ $C_{11}H_{11}NO_2$ requires 189.08].

Example 27

3-((4-Chlorophenyl)thio)-6-ethyl-1H-indole-2-carboxylic acid (1 h)

Following the method used to prepare 1, the use of 38 (125 mg, 0.66 mmol) and 26 (227 mg, 0.79 mmol) provided 126 mg of 1 h (57%) as an off white solid, mp 210° C. $^1$H NMR (300 MHz, DMSO-$d_6$) δ 1.20 (t, J=7 Hz, 3H), 2.70 (q, J=7 Hz, 2H), 6.96-7.06 (m, 3H), 7.24-7.32 (m, 4H), 12.21 (s, 1H), 13.32 (s, 1H). LC-MS (CI): m/z 330.0 [(M−H)$^−$ $C_{17}H_{14}ClNO_2S$ requires 331.04]. Purity (100%). Calcd for $C_{17}H_{14}ClNO_2S \cdot 0.2H_2O \cdot 0.01HCl$: C, 60.81; H, 4.33; N, 4.17; S, 9.55; Cl, 10.66. Found: C, 60.67; H, 4.22; N, 4.10; S, 9.28; Cl, 11.01.

Example 28

3-((4-Chlorophenyl)thio)-4-methoxy-1H-indole-2-carboxylic acid (1i)

Following the method used to prepare 1, the use of 38 (0.3 g, 1.57 mmol) and 26 (0.51 g, 1.77 mmol) provided 0.27 g of 1i (51%) as a white foam. $^1$H NMR (300 MHz, DMSO-$d_6$) δ 3.58 (s, 3H), 6.52 (d, J=8 Hz, 1H), 7.01 (d, J=8 Hz, 2H), 7.09 (d, J=8 Hz, 1H), 7.19 (d, J=8 Hz, 1H), 7.25 (d, J=8 Hz, 2H), 12.26 (s, 1H), 13.28 (s, 1H). LC-MS (CI): m/z 332.0 [(M−H)$^−$ $C_{16}H_{12}ClNO_2S$ requires 333.02]. Purity (100%). Calcd for $C_{16}H_{12}ClNO_2S$: C, 57.57; H, 3.62; N, 4.20; S, 9.61 Found: C, 57.54; H, 3.53; N, 4.17; S, 9.88.

Example 29

3-((4-chlorophenyl)thio)-4,7-dimethyl-1H-indole-2-carboxylic acid (1j)

Following the method used to prepare 1, the use of 4,7-dimethyl-1H-indole-2-carboxylic acid (40) (150 mg, 0.79 mmol) and 26 (280 mg, 0.97 mmol) provided 106 mg of 1j (40%) as an off white solid, mp 228-230° C. $^1$H NMR (300 MHz, CD$_3$OD) δ 2.50 (s, 3H), 2.57 (s, 3H), 6.75 (d, J=7 Hz, 1H), 6.80-6.97 (m, 3H), 7.15 (d, J=8 Hz, 2H). LC-MS (CI): m/z 330.1 [(M−H)$^−$ $C_{17}H_{14}ClNO_2S$ requires 331.04]. Purity (100%). Calcd $C_{17}H_{14}ClNO_2S \cdot 0.2H_2O$: C, 60.87; H, 4.33; N, 4.18; S, 9.56; Cl, 10.57. Found: C, 60.50; H, 4.06; N, 4.18; S, 9.73; Cl, 10.80.

Example 30

Methyl 3-((4-chlorophenyl)thio)-5-methyl-1H-indole-2-carboxylate (7)

Following the method used to prepare 24a, the use of 1b (0.51 g, 1.60 mmol) and oxalyl chloride (0.32 mL, 3.65 mmol) followed by allowing the intermediate acid chloride to react with MeOH (5 mL) provided 0.95 g (90%) of product 7 as a white solid, mp 230-233° C. $^1$H NMR (300 MHz, DMSO-$d_6$) δ 2.34 (s, 3H), 3.84 (s, 3H), 7.05 (d, J=8 Hz, 2H), 7.16-7.20 (m, 1H), 7.25-7.28 (m, 3H), 7.45 (d, J=8 Hz, 1H), 12.41 (s, 1H). LC-MS (CI): m/z 332.1 [(M+H)$^+$ $C_{17}H_{14}ClNO_2S$ requires 331.04]. Purity (100%). Calcd for $C_{17}H_{14}ClNO_2S \cdot 0.2H_2O$: C, 60.87; H, 4.33; N, 4.18; S, 9.56; Cl, 10.57. Found: C, 60.89; H, 4.08; N, 4.14; S, 9.81; Cl, 10.77.

Example 31

Methyl 3-((4-chlorophenyl)thio)-1,5-dimethyl-1H-indole-2-carboxylate (4)

Compound 7 (200 mg, 0.6 mmol) was added in portions to a mixture of sodium hydride (60 mg, 1.2 mmol) in DMF (5 mL) at 0° C. After 15 min, methyl iodide (50 μL, 0.9 mmol) was added and the mixture was stirred for 1 h. The reaction was allowed to warm to rt and stirred overnight under $N_2$. The reaction mixture was then quenched with ice water and extracted with EtOAc. The organic layers were combined, dried over $MgSO_4$, and concentrated in vacuo. The crude product was purified by flash column chromatography eluting with a linear gradient ranging from 0 to 50% EtOAc-hexanes to provide 166 mg (63%) of product 4 as an off white solid, mp 110-111° C. $^1$H NMR (300 MHz, DMSO-$d_6$) δ 2.35 (s, 3H), 3.83 (s, 3H), 4.00 (s, 3H), 7.06 (d, J=9 Hz, 2H), 7.23-7.29 (m, 4H), 7.63 (d, J=9 Hz, 1H). LC-MS (CI): m/z 346.1 [(M+H)$^+$ $C_{18}H_{16}ClNO_2S$ requires 345.06]. Purity (100%). Calcd for $C_{18}H_{16}ClNO_2S$: C, 62.51; H, 4.66; N, 4.05; S, 9.27; Cl, 10.25. Found: C, 62.79; H, 4.64; N, 3.98; S, 9.05; Cl, 10.03.

Example 32

3-((4-Chlorophenyl)thio)-1,5-dimethyl-1H-indole-2-carboxylic acid (2)

Following the method used to prepare 47, the use of 4 (166 mg, 0.48 mmol) provided 158 mg (75%) of product 2 as a brown solid, mp 205-206° C. $^1$H NMR (300 MHz, DMSO-$d_6$) δ 2.35 (s, 3H), 4.04 (s, 3H), 6.99-7.03 (m, 2H), 7.21-7.28 (m, 4H), 7.60 (d, J=9 Hz, 1H), 13.58 (s, 1H). LC-MS (CI): m/z 330.0 [(M−H)$^-$ $C_{17}H_{14}ClNO_2S$ requires 331.04]. Purity (100%). Calcd for $C_{17}H_{14}ClNO_2S$: C, 61.53; H, 4.25; N, 4.22; S, 9.66; Cl, 10.68. Found: C, 61.52; H, 4.32; N, 4.19; S, 9.82; Cl, 10.63.

Example 33

Methyl 3-((4-chlorophenyl)thio)-1-ethyl-5-methyl-1H-indole-2-carboxylate (5)

Following the method used to prepare 4, the use of 7 (0.27 g, 0.81 mmol) and ethyl iodide (0.1 mL, 1.25 mmol) provided 0.27 g (51%) of product 4 as an off white gum. The compound contains 7% of the corresponding ethyl ester. $^1$H NMR (300 MHz, DMSO-$d_6$) δ 1.35 (t, J=7 Hz, 3H), 2.34 (s, 3H), 3.83 (s, 3H), 4.57 (q, J=7 Hz, 2H), 7.05 (d, J=9 Hz, 2H), 7.22-7.30 (m, 4H), 7.64 (d, J=9 Hz, 1H). LC-MS (CI): m/z 360.1 [(M+H)$^+$ $C_{19}H_{18}ClNO_2S$ requires 359.07]. Purity (99%). Calcd for $C_{19}H_{18}ClNO_2S$: C, 63.41; H, 5.04; N, 3.89; S, 8.91; Cl, 9.85. Found: C, 63.48; H, 5.14; N, 3.85; S, 9.02; Cl, 9.70.

Example 34

3-((4-Chlorophenyl)thio)-1-ethyl-5-methyl-1H-indole-2-carboxylic acid (3)

Following the method used to prepare 47, the use of 5 (106 mg, 0.29 mmol) provided 96 mg (94%) of product 3 as an off white solid, mp 229-231° C. $^1$H NMR (300 MHz, DMSO-$d_6$) δ 1.35 (t, J=7 Hz, 3H), 2.34 (s, 3H), 4.58 (q, J=7 Hz, 2H), 7.01 (d, J=9 Hz, 2H), 7.20-7.28 (m, 4H), 7.62 (d, J=9 Hz, 1H), 13.58 (s, 1H). LC-MS (CI): m/z 344.0 [(M−H)$^-$ $C_{18}H_{16}ClNO_2S$ requires 345.06]. Purity (100%). Calcd for $C_{18}H_{16}ClNO_2S \cdot 0.05CH_2Cl_2$: C, 61.93; H, 4.64; N, 4.00; S, 9.16; Cl, 11.14. Found: C, 61.73; H, 4.59; N, 3.88; S, 9.29; Cl, 11.19.

Example 35

Methyl 3-((4-chlorophenyl)thio)-6-methyl-1H-indole-2-carboxylate (6)

Following the method used to prepare 34, the use of 1 (100 mg, 0.32 mmol) and TMSCHN$_2$ (2.0 M solution in diethyl ether) (0.32 mL, 0.64 mmol) provided 79 mg of product 6 (75%) as a white solid, mp 147-149° C. $^1$H NMR (300 MHz, DMSO-$d_6$) δ 2.40 (s, 3H), 3.85 (s, 3H), 6.96 (d, J=9 Hz, 1H), 7.06 (d, J=9 Hz, 2H), 7.25-7.31 (m, 4H), 12.35 (s, 1H). LC-MS (CI): m/z 330.0 [(M−H)$^-$ $C_{17}H_{14}ClNO_2S$ requires 331.04]. Purity (100%). Calcd for $C_{17}H_{14}ClNO_2S$: C, 61.53; H, 4.25; N, 4.22; S, 9.66; Cl, 10.68. Found: C, 61.48; H, 4.27; N, 4.13; S, 9.79; Cl, 10.64.

Example 36

Methyl 3-((4-chlorophenyl)thio)-7-methyl-1H-indole-2-carboxylate (8)

Following the method used to prepare 34, the use of 1c (80 mg, 0.25 mmol) and TMSCHN$_2$ (2.0 M solution in diethyl ether) (0.29 mL, 0.58 mmol) provided 80 mg of product 8 (95%) as a white solid, mp 170° C. $^1$H NMR (300 MHz, DMSO-$d_6$) δ 2.56 (s, 3H), 3.87 (s, 3H), 7.00-7.06 (m, 3H), 7.14 (d, J=7 Hz, 1H), 7.24-7.28 (m, 3H), 12.30 (s, 1H). LC-MS (CI): m/z 332.1 [(M+H)$^+$ $C_{17}H_{14}ClNO_2S$ requires 331.04]. Purity (100%). Calcd for $C_{17}H_{14}ClNO_2S \cdot 0.3H_2O$: C, 60.55; H, 4.36; N, 4.15; S, 9.51; Cl, 10.51. Found: C, 60.79; H, 4.05; N, 4.15; S, 9.51; Cl, 10.87.

Example 37

Ethyl 3-((4-chlorophenyl)thio)-5-methyl-1H-indole-2-carboxylate (10)

Following the method used to prepare 24a, the use of 1b (0.23 mmol) and oxalyl chloride in THF followed by allowing the intermediate acid chloride to react with EtOH (5 mL) provided 61 mg (76%) of product 10 as a white solid, mp 158-160° C. $^1$H NMR (300 MHz, DMSO-$d_6$) δ 1.24 (t, J=7 Hz, 3H), 2.34 (s, 3H), 4.30 (q, J=7 Hz, 2H), 7.05 (d, J=8 Hz, 2H), 7.16 (d, J=8 Hz, 1H), 7.26-7.29 (m, 3H), 7.46 (d, J=9 Hz, 1H), 12.38 (s, 1H). LC-MS (CI): m/z 346.1 [(M+H)$^+$ $C_{18}H_{16}ClNO_2S$ requires 345.06]. Purity (100%). Calcd for $C_{18}H_{16}ClNO_2S$: C, 62.51; H, 4.66; N, 4.05; S, 9.27; Cl, 10.25. Found: C, 62.37; H, 4.60; N, 3.95; S, 9.21; Cl, 10.30.

Example 38

Isopropyl 3-((4-chlorophenyl)thio)-5-methyl-1H-indole-2-carboxylate (12)

Following the method used to prepare 24a, 1b (0.21 mmol) and oxalyl chloride in THF followed by allowing the intermediate acid chloride to react with 2-propanol (2 mL) provided 44 mg (58%) of product 12 as a white solid, mp 172-174° C. $^1$H NMR (300 MHz, DMSO-$d_6$) δ 1.18-1.24 (m, 6H), 2.35 (s, 3H), 5.09-5.12 (m, 1H), 7.04 (dd, J=2, 9 Hz, 2H), 7.19

(d, J=8, 1H), 7.25-7.30 (m, 3H), 7.46 (dd, J=2, 9 Hz, 1H), 12.34 (s, 1H). LC-MS (CI): m/z 360.0 [(M+H)+ $C_{19}H_{18}ClNO_2S$ requires 359.07]. Purity (100%). Calcd for $C_{19}H_{18}ClNO_2S$: C, 63.41; H, 5.04; N, 3.89; S, 8.91; Cl, 9.85. Found: C, 63.59; H, 4.97; N, 3.90; S, 9.04; Cl, 9.85.

Example 39

Phenyl 3-((4-chlorophenyl)thio)-5-methyl-1H-indole-2-carboxylate (14)

Following the method used to prepare 24a, 1b (0.18 mmol) and oxalyl chloride in THF followed by allowing the intermediate acid chloride to react with phenol (33 mg, 0.36 mmol) in the presence of $Et_3N$ (95 µL, 0.72 mmol) provided 35 mg (50%) of product 14 as a white foam. $^1$H NMR (300 MHz, DMSO-$d_6$) δ 2.37 (s, 3H), 7.12 (d, J=9 Hz, 2H), 7.18-7.34 (m, 7H), 7.43-7.52 (m, 3H), 12.67 (s, 1H). Purity (98%). Calcd for $C_{22}H_{16}ClNO_2S$: C, 67.08; H, 4.09; N, 3.56; S, 8.14; Cl, 9.00. Found: C, 67.15; H, 3.92; N, 3.59; S, 8.07; Cl, 8.93.

Example 40

Benzyl 3-((4-chlorophenyl)thio)-5-methyl-1H-indole-2-carboxylate (16)

Following the method used to prepare 24a, the use of 1b (0.23 mmol) and oxalyl chloride in THF followed by allowing the intermediate acid chloride to react with benzyl alcohol (35 µL, 0.34 mmol) in presence of pyridine (54 µL, 0.68 mmol) provided 35 mg (37%) of product 16 as a pale yellow foam. $^1$H NMR (300 MHz, DMSO-$d_6$) δ 2.34 (s, 3H), 5.35 (s, 2H), 7.00 (d, J=9 Hz, 2H), 7.20 (d, J=9 Hz, 1H), 7.26 (d, J=9 Hz, 2H), 7.29-7.38 (m, 6H), 7.47 (d, J=9 Hz, 1H), 12.44 (s, 1H). LC-MS (CI): m/z 408.1 [(M+H)+ $C_{23}H_{18}ClNO_2S$ requires 407.6]. Purity (100%). Calcd for $C_{23}H_{18}ClNO_2S$: C, 67.72; H, 4.45; N, 3.43; S, 7.86; Cl, 8.69. Found: C, 67.53; H, 4.55; N, 3.42; S, 8.09; Cl, 8.45.

Example 41

Methyl 3-((4-chlorophenyl)thio)-4-methyl-1H-indole-2-carboxylate (9)

Following the method used to prepare 24a, the use of 1a (0.19 mmol) and oxalyl chloride in THF followed by allowing the intermediate acid chloride to react with MeOH (3 mL) provided 52 mg (81%) of product 9 as a white solid, mp 192-193° C. $^1$H NMR (300 MHz, DMSO-$d_6$) δ 2.57 (s, 3H), 3.84 (s, 3H), 6.88 (d, J=7 Hz, 1H), 6.95-6.98 (m, 2H), 7.24 (t, J=8 Hz, 1H), 7.26-7.29 (m, 2H), 7.41 (d, J=9 Hz, 1H), 12.52 (s, 1H). LC-MS (CI): m/z 332.1 [(M+H)+ $C_{17}H_{14}ClNO_2S$ requires 331.04]. Purity (100%). Calcd for $C_{17}H_{14}ClNO_2S$: C, 61.53; H, 4.25; N, 4.22; S, 9.66; Cl, 10.68. Found: C, 61.25; H, 4.24; N, 4.14; S, 9.56; Cl, 10.64.

Example 42

Ethyl 3-((4-chlorophenyl)thio)-4-methyl-1H-indole-2-carboxylate (11)

Following the method used to prepare 24a, the use of 1a (0.19 mmol) and oxalyl chloride in THF followed by allowing the intermediate acid chloride to react with EtOH (3 mL) provided 41 mg (62%) of product 11 as a white solid, mp 186-188° C. $^1$H NMR (300 MHz, DMSO-$d_6$) δ 1.25 (t, J=7 Hz, 3H), 2.59 (s, 3H), 4.31 (q, J=7 Hz, 2H), 6.88 (d, J=7 Hz, 1H), 6.94-6.98 (m, 2H), 7.23 (t, J=8 Hz, 1H), 7.25-7.30 (m, 2H), 7.42 (d, J=8 Hz, 1H), 12.48 (s, 1H). LC-MS (CI): m/z 346.1 [(M+H)+ $C_{18}H_{16}ClNO_2S$ requires 345.06]. Purity (100%). Calcd for $C_{18}H_{16}ClNO_2S$: C, 62.51; H, 4.66; N, 4.05; S, 9.27; Cl, 10.25. Found: C, 62.53; H, 4.59; N, 4.08; S, 9.27; Cl, 10.35.

Example 43

Isopropyl 3-((4-chlorophenyl)thio)-4-methyl-1H-indole-2-carboxylate (13)

Following the method used to prepare 24a, the use of 1a (0.21 mmol) and oxalyl chloride in THF followed by allowing the intermediate acid chloride to react with 2-propanol (2 mL) provided 40 mg (53%) of product 13 as a white solid, mp 190-192° C. $^1$H NMR (300 MHz, DMSO-$d_6$) δ 1.22 (d, J=6 Hz, 6H), 2.60 (s, 3H), 5.05-5.14 (m, 1H), 6.88 (d, J=8 Hz, 1H), 6.98 (d, J=9 Hz, 2H), 7.23 (t, J=8 Hz, 1H), 7.30 (d, J=9 Hz, 2H), 7.42 (d, J=9 Hz, 1H), 12.45 (s, 1H). LC-MS (CI): m/z 360.1 [(M+H)+ $C_{19}H_{18}ClNO_2S$ requires 359.07]. Purity (100%). Calcd for $C_{19}H_{18}ClNO_2S \cdot 0.07CH_2Cl_2$: C, 62.61; H, 5.00; N, 3.83; S, 8.77; Cl, 11.05. Found: C, 62.32; H, 5.01; N, 3.77; S, 9.08; Cl, 10.93.

Example 44

Phenyl 3-((4-chlorophenyl)thio)-4-methyl-1H-indole-2-carboxylate (15)

Following the method used to prepare 24a, the use of 1a (0.24 mmol) and oxalyl chloride in THF followed by allowing the intermediate acid chloride to react with phenol (33 mg, 0.36 mmol) in presence of pyridine (100 µL) provided 42 mg (45%) of product 15 as a white foam. $^1$H NMR (300 MHz, $CDCl_3$) δ 2.74 (s, 3H), 6.95-7.03 (m, 3H), 7.08-7.16 (m, 4H), 7.23-7.41 (m, 5H), 9.43 (s, 1H). LC-MS (CI): m/z 394.1 [(M+H)+ $C_{22}H_{16}ClNO_2S$ requires 393.06]. Purity (98%). Calcd for $C_{22}H_{16}ClNO_2S$: C, 67.08; H, 4.09; N, 3.56; S, 8.14; Cl, 9.00. Found: C, 67.09; H, 3.98; N, 3.64; S, 8.34; Cl, 9.14.

Example 45

Benzyl 3-((4-chlorophenyl)thio)-4-methyl-1H-indole-2-carboxylate (17)

Following the method used to prepare 24a, the use of 1a (0.21 mmol) and oxalyl chloride in THF followed by allowing the intermediate acid chloride to react with benzyl alcohol (33 µL, 0.32 mmol) in the presence of pyridine (54 µL, 0.68 mmol) provided 17 mg (20%) of product 17 as a pale yellow foam. $^1$H NMR (300 MHz, DMSO-$d_6$) δ 2.59 (s, 3H), 5.36 (s, 2H), 6.89 (d, J=7 Hz, 1H), 6.95 (d, J=9 Hz, 1H), 7.22 (d, J=8 Hz, 2H), 7.24-7.27 (m, 2H), 7.31-7.39 (m, 5H), 7.43 (d, J=8 Hz, 1H), 12.45 (s, 1H). LC-MS (CI): m/z 408.1 [(M+H)+ $C_{23}H_{18}ClNO_2S$ requires 407.6]. Purity (100%). Calcd for $C_{23}H_{18}ClNO_2S$: C, 67.72; H, 4.45; N, 3.43; S, 7.86; Cl, 8.69. Found: C, 67.48; H, 4.43; N, 3.42; S, 7.85; Cl, 8.98.

Example 46

6-Methyl-3-(phenylthio)-1H-indole-2-carboxylic acid (18)

Following the method used to prepare 1, the use of 25 (0.4 g, 2.30 mmol) and diphenyldisulfide (0.55 g, 2.52 mmol) provided 0.18 g of product 18 (27%) as an off white solid, mp 169° C. $^1$H NMR (300 MHz, DMSO-d$_6$) δ 2.39 (s, 3H), 6.92 (d, J=8 Hz, 1H), 7.04 (d, J=8 Hz, 2H), 7.10 (d, J=8 Hz, 1H), 7.17-7.29 (m, 4H), 12.14 (s, 1H), 13.27 (s, 1H). LC-MS (CI): m/z 282.0 [(M−H)$^−$ C$_{16}$H$_{13}$NO$_2$S requires 283.07]. Purity (100%). Calcd for C$_{16}$H$_{13}$NO$_2$S: C, 67.82; H, 4.62; N, 4.94; S, 11.32. Found: C, 67.93; H, 4.64; N, 4.97; S, 11.49.

Example 47

6-Methyl-3-(phenylthio)-1H-indole-2-carboxylate (29)

Following the method used to prepare 34, the use of 18 (50 mg, 0.18 mmol) and TMSCHN$_2$ (2.0 M solution in diethyl ether) (0.20 mL, 0.40 mmol) provided 37 mg of product 29 (71%) as a white solid, mp 164° C. $^1$H NMR (300 MHz, DMSO-d$_6$) δ 2.40 (s, 3H), 3.85 (s, 3H), 6.94 (d, J=9 Hz, 1H), 7.04-7.12 (m, 3H), 7.17-7.29 (m, 4H), 12.29 (s, 1H). LC-MS (CI): m/z 298.1 [(M+H)$^+$ C$_{17}$H$_{15}$NO$_2$S requires 297.08]. Purity (100%). Calcd for C$_{17}$H$_{15}$NO$_2$S: C, 68.66; H, 5.08; N, 4.71; S, 10.78. Found: C, 68.51; H, 5.14; N, 4.62; S, 10.66.

Example 48

3-((3-Chlorophenyl)thio)-6-methyl-1H-indole-2-carboxylic acid (18a)

Following the method used to prepare 1, the use of 25 (150 mg, 0.86 mmol) and bis(3-chlorophenyl)disulfide (55) (287 mg, 1.0 mmol) provided 135 g of product 18a (50%) as an off white solid, mp 193° C. $^1$H NMR (300 MHz, DMSO-d$_6$) δ 2.40 (s, 3H), 6.46-6.49 (m, 1H), 6.96 (d, J=9 Hz, 1H), 7.04-7.10 (m, 2H), 7.28 (d, J=9 Hz, 1H), 7.32 (s, 1H), 7.04-7.10 (m, 1H), 12.30 (s, 1H), 13.31 (s, 1H). LC-MS (CI): m/z 316.0 [(M−H)$^−$ C$_{16}$H$_{12}$ClNO$_2$S requires 317.03]. Purity (100%). Calcd for C$_{16}$H$_{12}$ClNO$_2$S: C, 60.47; H, 3.81; N, 4.41; S, 10.09; Cl, 11.16. Found: C, 60.83; H, 3.86; N, 4.37; S, 9.69; Cl, 10.78.

Example 49

3-((3-Fluorophenyl)thio)-6-methyl-1H-indole-2-carboxylic acid (18b)

Following the method used to prepare 1, the use of 25 (0.2 g, 1.15 mmol) and bis(3-fluorophenyl)disulfide (57) (0.35 g, 1.38 mmol) provided 0.14 g of product 18b (40%) as an off white solid, mp 160-162° C. $^1$H NMR (300 MHz, DMSO-d$_6$) δ 2.40 (s, 3H), 6.74-6.77 (m, 1H), 6.82-6.85 (m, 1H), 6.86-6.96 (m, 2H), 7.20-7.31 (m, 3H), 12.24 (s, 1H), 13.33 (s, 1H). LC-MS (CI): m/z 300.0 [(M−H)$^−$ C$_{16}$H$_{12}$FNO$_2$S requires 301.06]. Purity (100%). Calcd for C$_{16}$H$_{12}$FNO$_2$S: C, 63.77; H, 4.01; N, 4.65; S, 10.64. Found: C, 63.81; H, 3.91; N, 4.69; S, 10.38.

Example 50

3-((4-Bromophenyl)thio)-6-methyl-1H-indole-2-carboxylic acid (18c)

Following the method used to prepare 1, the use of 25 (0.15 g, 0.86 mmol) and bis(3-bromophenyl)disulfide (57) (0.38 g, 1.02 mmol) provided 0.1 g of product 18c (32%) as an off white solid, mp 224-225° C. $^1$H NMR (300 MHz, DMSO-d$_6$) δ 2.39 (s, 3H), 6.93-6.96 (m, 3H), 7.29 (d, J=9 Hz, 2H), 7.39 (d, J=9 Hz, 2H), 12.21 (s, 1H), 13.30 (s, 1H). LC-MS (CI): m/z 359.9 [(M−H)$^−$ C$_{16}$H$_{12}$BrNO$_2$S requires 360.98]. Purity (100%). Calcd for C$_{16}$H$_{12}$BrNO$_2$S: C, 53.05; H, 3.34; N, 3.87. Found: C, 53.10; H, 3.21; N, 3.74.

Example 51

6-Methyl-3-(p-tolylthio)-1H-indole-2-carboxylic acid (18d)

Following the method used to prepare 1, the use of 25 (0.3 g, 1.71 mmol) and bis(p-tolyl)disulfide (58) (0.5 g, 2.03 mmol) provided 0.12 g of 18d (24%) as an off white solid, mp 215-220° C. $^1$H NMR (300 MHz, DMSO-d$_6$) δ 2.20 (s, 3H), 2.38 (s, 3H), 6.90 (d, J=8 Hz, 1H), 6.94-7.03 (m, 4H), 7.24 (d, J=9 Hz, 1H), 7.27 (s, 1H), 12.07 (s, 1H), 13.21 (s, 1H). LC-MS (CI): m/z 296.0 [(M−H)$^−$ C$_{14}$H$_{15}$NO$_2$S requires 297.08]. Purity (99%). Calcd for C$_{17}$H$_{15}$NO$_2$S: C, 68.66; H, 5.08; N, 4.71; S, 10.78. Found: C, 68.60; H, 4.97; N, 4.70; S, 10.67.

Example 52

3-((4-Methoxyphenyl)thio)-6-methyl-1H-indole-2-carboxylic acid (18e)

Following the method used to prepare 1, 25 (0.3 g, 1.71 mmol) and bis(4-methoxyphenyl)disulfide (59) (0.53 g, 1.91 mmol) provided 0.16 g of product 18e (29%) as a brown solid, mp 190-192° C. $^1$H NMR (300 MHz, DMSO-d$_6$) δ 2.37 (s, 3H), 3.68 (s, 3H), 6.83 (d, J=8 Hz, 2H), 6.88 (d, J=8 Hz, 1H), 7.13 (d, J=8 Hz, 2H), 7.20-7.24 (m, 2H), 11.98 (s, 1H), 13.20 (s, 1H). LC-MS (CI): m/z 312.0 [(M−H)$^−$ C$_{17}$H$_{15}$NO$_3$S requires 313.08]. Purity (100%). Calcd for C$_{17}$H$_{15}$NO$_3$S.0.1H$_2$O: C, 64.78; H, 4.86; N, 4.44; S, 10.17. Found: C, 64.82; H, 4.88; N, 4.44; S, 9.88.

Example 53

3-((4-(Methoxycarbonyl)phenyl)thio)-6-methyl-1H-indole-2-carboxylic acid (61)

Following the method used to prepare 1, the use of 25 (125 mg, 0.71 mmol) and 4,4'-dithiobisbenzoic acid dimethyl ester (60) (500 mg, 1.45 mmol) provided 85 mg of product 61 (35%) as a brown solid. $^1$H NMR (300 MHz, DMSO-d$_6$) δ 2.38 (s, 3H), 3.78 (s, 3H), 6.92 (d, J=8 Hz, 1H), 7.07 (d, J=8 Hz, 2H), 7.25 (d, J=8 Hz, 1H), 7.30 (s, 1H), 7.75 (d, J=8 Hz, 2H), 12.11 (s, 1H), 13.19 (s, 1H). LC-MS (CI): m/z 340.0 [(M−H)$^−$ C$_{18}$H$_{15}$NO$_4$S requires 341.07].

Example 54

3-((4-Carboxyphenyl)thio)-6-methyl-1H-indole-2-carboxylic acid (18f)

Following the method used to prepare 47, the use of 61 (80 mg, 0.23 mmol) provided 46 mg (60%) of product 18f as a white foam. $^1$H NMR (300 MHz, DMSO-d$_6$) δ 2.40 (s, 3H), 6.96 (d, J=8 Hz, 1H), 7.06 (d, J=8 Hz, 2H), 7.29 (d, J=9 Hz, 1H), 7.31 (s, 1H), 7.75 (d, J=8 Hz, 2H), 12.27 (s, 1H), 13.01 (s, 1H). LC-MS (CI): m/z 326.1 [(M−H)$^−$ C$_{14}$H$_{13}$NO$_4$S requires 327.06]. Purity (100%). Calcd for C$_{17}$H$_{13}$NO$_4$S: C, 62.37; H, 4.00; N, 4.28; S, 9.80. Found: C, 62.24; H, 3.94; N, 4.19; S, 9.72.

Example 55

6-Methyl-3-((4-(trifluoromethyl)phenyl)thio)-1H-indole-2-carboxylic acid (18g)

Following the method used to prepare 1, the use of 25 (0.15 g, 0.86 mmol) and bis(4-trifluoromethylphenyl)disulfide (62) (0.38 g, 1.07 mmol) provided 0.13 g of product 18g (43%) as an off white solid, mp 223° C. $^1$H NMR (300 MHz, DMSO-$d_6$) δ 2.41 (s, 3H), 6.98 (d, J=8 Hz, 2H), 7.15 (d, J=8 Hz, 2H), 7.30-7.33 (m, 2H), 7.56 (d, J=8 Hz, 1H), 12.32 (s, 1H), 13.37 (s, 1H). LC-MS (CI): m/z 350.1 [(M−H)$^-$ $C_{17}H_{12}F_3NO_2S$ requires 351.05]. Purity (100%). Calcd for $C_{17}H_{12}F_3NO_2S$: C, 58.11; H, 3.44; N, 3.99; S, 9.13; F, 16.22. Found: C, 58.05; H, 3.33; N, 3.99; S, 9.28; F, 15.99.

Example 56

3-((4-Methoxyphenyl)thio)-4-methyl-1H-indole-2-carboxylic acid (19)

Following the method used to prepare 1, the use of 27 (0.3 g, 1.71 mmol) and bis(4-methoxyphenyl)disulfide (63) (0.53 g, 1.91 mmol) provided 0.13 g of product 19 (24%) as a brown solid, mp 185-186° C. $^1$H NMR (300 MHz, DMSO-$d_6$) δ 2.60 (s, 3H), 3.66 (s, 3H), 6.78-6.83 (m, 3H), 6.94 (d, J=9 Hz, 2H), 7.14 (t, J=8 Hz, 1H), 7.36 (d, J=8 Hz, 1H), 12.24 (s, 1H), 13.28 (s, 1H). LC-MS (CI): m/z 312.0 [(M−H)$^-$ $C_{17}H_{15}NO_3S$ requires 313.08]. Purity (100%). Calcd for $C_{17}H_{15}NO_3S \cdot 0.3H_2O$: C, 64.05; H, 4.93; N, 4.39; S, 10.06. Found: C, 64.09; H, 4.77; N, 4.34; S, 9.98.

Example 57

4-Methyl-3-(p-tolylthio)-1H-indole-2-carboxylic acid (19a)

Following the method used to prepare 1, the use of 27 (0.3 g, 1.71 mmol) and bis(p-tolyl)disulfide (58) (0.51 g, 2.07 mmol) provided 0.09 g of product 19a (17%) as an off white solid, mp 202° C. $^1$H NMR (300 MHz, DMSO-$d_6$) δ 2.19 (s, 3H), 2.56 (s, 3H), 6.89-6.79 (m, 3H), 6.98-7.03 (m, 2H), 7.18 (t, J=8 Hz, 1H), 7.37 (d, J=8 Hz, 1H), 12.29 (s, 1H), 13.27 (s, 1H). LC-MS (CI): m/z 296.0 [(M−H)$^-$ $C_{17}H_{15}NO_2S$ requires 297.08]. Purity (100%). Calcd for $C_{17}H_{15}NO_2S$: C, 68.66; H, 5.08; N, 4.71; S, 10.78. Found: C, 68.36; H, 5.12; N, 4.71; S, 10.55.

Example 58

3-((4-(Methoxycarbonyl)phenyl)thio)-4-methyl-1H-indole-2-carboxylic acid (19b)

Following the method used to prepare 1, the use of 27 (125 mg, 0.71 mmol) and 4,4'-dithiobisbenzoic acid dimethyl ester (60) (500 mg, 1.45 mmol) provided 85 mg of product 19b (35%) as a brown solid. $^1$H NMR (300 MHz, DMSO-$d_6$) δ 2.52 (s, 3H), 3.78 (s, 3H), 6.85 (d, J=7 Hz, 1H), 7.05 (d, J=9 Hz, 2H), 7.21 (t, J=8 Hz, 1H), 7.40 (d, J=8 Hz, 1H), 7.79 (d, J=8 Hz, 2H), 12.11 (s, 1H), 13.19 (s, 1H). LC-MS (CI): m/z 340.0 [(M−H)$^-$ $C_{18}H_{15}NO_4S$ requires 341.07]. Purity (100%). Calcd for $C_{17}H_{15}NO_2S$: C, 63.33; H, 4.43; N, 4.10; S, 9.39. Found: C, 63.44; H, 4.40; N, 4.06; S, 9.27.

Example 59

4-Methyl-3-((4-nitrophenyl)thio)-1H-indole-2-carboxylic acid (19c)

Following the method used to prepare 1, the use of 27 (0.3, 1.71 mmol) and 4-nitrophenyl disulfide (64) (0.63 g, 2.05 mmol) provided 0.27 g of product 19c (48%) as a yellow solid, mp 242-244° C. $^1$H NMR (300 MHz, DMSO-$d_6$) δ 2.53 (s, 3H), 6.88 (d, J=7 Hz, 1H), 7.16 (d, J=8 Hz, 2H), 7.22 (t, J=8 Hz, 1H), 7.42 (d, J=8 Hz, 1H), 8.08 (d, J=9 Hz, 2H), 12.55 (s, 1H), 13.47 (s, 1H). LC-MS (CI): m/z 327.0 [(M−H)$^-$ $C_{16}H_{12}N_2O_4S$ requires 328.05]. Purity (100%). Calcd for $C_{17}H_{15}NO_2S$: C, 58.53; H, 3.68; N, 8.53; S, 9.77. Found: C, 58.30; H, 3.48; N, 8.37; S, 9.66.

Example 60

3-((2,4-Dichlorophenyl)thio)-6-methyl-1H-indole-2-carboxylic acid (20)

Following the method used to prepare 1, the use of 25 (0.15 g, 0.86 mmol) and bis(2,4-dichlorophenyl)disulfide (65) (0.37 g, 1.03 mmol) provided 0.16 g of product 20 (53%) as an off white solid, mp 250-252° C. $^1$H NMR (300 MHz, DMSO-$d_6$) δ 2.41 (s, 3H), 6.48 (d, J=9 Hz, 1H), 6.98 (d, J=8 Hz, 1H), 7.17 (dd, J=2, 9 Hz, 1H), 7.30 (d, J=8 Hz, 1H), 7.33 (s, 1H), 7.30 (d, J=2 Hz, 1H), 12.37 (s, 1H), 13.44 (s, 1H). LC-MS (CI): m/z 350.0, 352.0 [(M−H)$^-$ $C_{16}H_{11}Cl_2NO_2S$ requires 350.99]. Purity (100%). Calcd for $C_{16}H_{11}Cl_2NO_2S$: C, 54.56; H, 3.15; N, 3.98; S, 9.10; Cl, 20.13. Found: C, 54.70; H, 3.24; N, 3.84; S, 8.94; Cl, 19.86.

Example 61

3-((3,4-Dichlorophenyl)thio)-6-methyl-1H-indole-2-carboxylic acid (21)

Following the method used to prepare 1, product 1 (0.15 g, 0.85 mmol) and bis(3,4-dichlorophenyl)disulfide (66) (0.37 g, 1.03 mmol) provided 0.13 g of product 21 (43%) as an off white solid, mp 252-255° C. $^1$H NMR (300 MHz, DMSO-$d_6$) δ 2.40 (s, 3H), 6.95 (dd, J=2, 9 Hz, 1H), 6.99 (d, J=9 Hz, 1H), 7.23 (d, J=2 Hz, 1H), 7.30-7.34 (m, 2H), 7.46 (d, J=9 Hz, 1H), 12.30 (s, 1H), 13.38 (s, 1H). LC-MS (CI): m/z 350.0, 352.0 [(M−H)$^-$ $C_{16}H_{11}Cl_2NO_2S$ requires 350.99]. Purity (100%). Calcd for $C_{16}H_{11}Cl_2NO_2S \cdot 0.04\text{-}CH_2Cl_2$: C, 54.17; H, 3.14; N, 3.94; S, 9.02; Cl, 20.74. Found: C, 54.00; H, 2.95; N, 3.93; S, 9.02; Cl, 20.74.

Example 62

3-((3,4-Dichlorophenyl)thio)-7-methyl-1H-indole-2-carboxylic acid (22)

Following the method used to prepare 1, the use of 29 (150 mg, 0.85 mmol) and 66 (370 g, 1.03 mmol) provided 157 mg of product 22 (52%) as a pale yellow solid, mp 206-208° C. $^1$H NMR (300 MHz, DMSO-$d_6$) δ 2.56 (s, 3H), 6.95 (dd, J=2, 9 Hz, 1H), 7.01-7.13 (m, 2H), 7.24 (d, J=2 Hz, 1H), 7.28 (d, J=8 Hz, 1H), 7.45 (d, J=9 Hz, 1H), 12.28 (s, 1H), 13.50 (s, 1H). LC-MS (CI): m/z 350.0, 352.0 [(M−H)$^-$ $C_{16}H_{11}Cl_2NO_2S$ requires 350.99]. Purity (100%). Calcd for $C_{16}H_{11}Cl_2NO_2S$: C, 54.56; H, 3.15; N, 3.98; S, 9.10; Cl, 20.13. Found: C, 54.73; H, 3.21; N, 4.00; S, 9.19; Cl, 19.86.

Example 63

3-((3,4-Dichlorophenyl)thio)-6-ethyl-1H-indole-2-carboxylic acid (23)

Following the method used to prepare 1, the use of 38 (125 mg, 0.66 mmol) and 66 (266 mg, 0.79 mmol) provided 160 mg of product 23 (66%) as a pale yellow solid, mp 220-222° C. $^1$H NMR (300 MHz, DMSO-d$_6$) δ 1.23 (t, J=8 Hz, 3H), 2.73 (q, J=7 Hz, 2H), 6.95 (dd, J=2, 9 Hz, 1H), 7.03 (dd, J=1, 9 Hz, 1H), 7.25 (d, J=2 Hz, 1H), 7.33 (s, 1H), 7.36 (d, J=9 Hz, 1H), 7.46 (d, J=9 Hz, 1H), 12.31 (s, 1H), 13.41 (s, 1H). LC-MS (CI): m/z 364.0, 366.0 [(M–H)$^-$ C$_{17}$H$_{13}$Cl$_2$NO$_2$S requires 365.0]. Purity (100%). Calcd for C$_{17}$H$_{13}$Cl$_2$NO$_2$S: C, 55.75; H, 3.58; N, 3.82; S, 8.75; Cl, 19.36. Found: C, 55.66; H, 3.52; N, 3.77; S, 8.65; Cl, 19.14.

Example 64

3-((3,5-Dichlorophenyl)thio)-6-methyl-1H-indole-2-carboxylate (27)

Following the method used to prepare 34, the use of 24 (75 mg, 0.21 mmol) and TMSCHN$_2$ (2.0 M solution in diethyl ether) (0.22 mL, 0.64 mmol) provided 52 mg of product 27 (72%) as a white solid, mp 214° C. $^1$H NMR (300 MHz, DMSO-d$_6$) δ 2.42 (s, 3H), 3.85 (s, 3H), 6.98-7.04 (m, 3H), 7.28-7.37 (m, 3H), 12.50 (s, 1H). LC-MS (CI): m/z 364.0, 366.0 [(M–H)$^-$ C$_{17}$H$_{13}$Cl$_2$NO$_2$S requires 365.0]. Purity (100%). Calcd for C$_{17}$H$_{13}$Cl$_2$NO$_2$S: C, 55.75; H, 3.58; N, 3.82; S, 8.75; Cl, 19.36. Found: C, 55.54; H, 3.43; N, 3.74; S, 8.68; Cl, 19.19.

Example 65

3-((3,5-Dichlorophenyl)thio)-N,6-dimethyl-1H-indole-2-carboxamide (28)

To a solution of 24 (120 mg, 0.34 mmol) in dry THF (4 mL) under N$_2$ were added EDCI (78 mg, 0.40 mmol), HOBt (54 mg, 0.40 mmol), and DIPEA (0.11 mL, 0.68 mmol). The mixture was stirred for 15 min, and MeNH$_2$ (2.0 M solution in THF) (0.34 mL, 0.68 mmol) was added. After stirring overnight, the reaction mixture was diluted with EtOAc, washed with water and brine, dried over MgSO$_4$, and concentrated in vacuo. The crude product was purified by flash column chromatography eluting with a linear gradient ranging from 0 to 10% MeOH—CH$_2$Cl$_2$ to provide 68 g (55%) of product 28 as an off white solid. $^1$H NMR (300 MHz, DMSO-d$_6$) δ 2.41 (s, 3H), 2.85 (d, J=5 Hz, 3H), 6.96-7.02 (m, 3H), 7.29-7.36 (m, 3H), 8.12-8.19 (m, 1H), 12.24 (s, 1H). LC-MS (CI): m/z 363.0, 365.0 [(M–H)$^-$ C$_{17}$H$_{14}$Cl$_2$N$_2$OS requires 364.0]. Purity (100%). Calcd for C$_{17}$H$_{14}$Cl$_2$N$_2$OS: C, 55.90; H, 3.86; N, 7.67; S, 8.78; Cl, 19.41. Found: C, 55.87; H, 3.82; N, 3.49; S, 8.80; Cl, 19.18.

Example 66

3-((3,5-Dichlorophenyl)thio)-1H-indole-2-carboxylic acid (26)

Following the method used to prepare 1, the use of 30 (0.3 g, 1.86 mmol) and 54 (0.73 g, 2.04 mmol) provided 0.37 g of product 26 (62%) as an off white solid, mp 181° C. $^1$H NMR (300 MHz, DMSO-d$_6$) δ 6.99 (s, 1H), 7.00 (s, 1H), 7.19 (t, J=8 Hz, 1H), 7.31-7.38 (m, 2H), 7.49 (d, J=8 Hz, 1H), 7.57 (d, J=8 Hz, 1H), 12.52 (s, 1H), 13.54 (s, 1H). LC-MS (CI): m/z 335.9, 337.9 [(M–11)$^-$ C$_{15}$H$_9$Cl$_2$NO$_2$S requires 336.97]. Purity (100%). Calcd for C$_{15}$H$_9$Cl$_2$NO$_2$S: C, 53.27; H, 2.68; N, 4.14; S, 9.48; Cl, 20.97. Found: C, 53.36; H, 2.86; N, 4.28; S, 9.39; Cl, 20.72.

Example 67

6-Methyl-3-((2,4,5-trichlorophenyl)thio)-1H-indole-2-carboxylic acid (30)

Following the method used to prepare 1, the use of 25 (0.3 g, 1.71 mmol) and bis(2,4,5-trichlorophenyl)disulfide (67) (0.87 g, 2.05 mmol) provided 0.28 g of product 30 (42%) as an off white solid, mp 240-243° C. $^1$H NMR (300 MHz, DMSO-d$_6$) δ 2.42 (s, 3H), 6.52 (s, 1H), 7.02 (d, J=9 Hz, 1H), 7.29-7.37 (m, 2H), 7.90 (s, 1H), 12.45 (s, 1H), 13.43 (s, 1H). LC-MS (CI): m/z 383.9, 385.9 [(M–H)$^-$ C$_{16}$H$_{10}$Cl$_3$NO$_2$S requires 384.95]. Purity (100%). Calcd for C$_{16}$H$_{10}$Cl$_3$NO$_2$S·0.5H$_2$O·0.1C$_3$H$_7$NO (DMF): C, 48.58; H, 2.93; N, 3.82; S, 7.96; Cl, 26.39. Found: C, 48.93; H, 2.58; N, 3.61; S, 7.92; Cl, 26.04.

Example 68

7-Methyl-3-((2,4,5-trichlorophenyl)thio)-1H-indole-2-carboxylic acid (30a)

Following the method used to prepare 1, the use of 29 (0.15 g, 0.86 mmol) and 67 (0.44 g, 1.03 mmol) provided 0.17 g of product 30a (50%) as an off white foam. $^1$H NMR (300 MHz, DMSO-d$_6$) δ 2.57 (s, 3H), 6.55 (s, 1H), 7.01-7.11 (m, 2H), 7.25 (d, J=8 Hz, 1H), 7.86 (s, 1H), 12.13 (s, 1H). LC-MS (CI): m/z 384.0, 386.0 [(M–H)$^-$ C$_{16}$H$_{10}$Cl$_3$NO$_2$S requires 384.95]. Purity (98%). Calcd for C$_{16}$H$_{10}$Cl$_3$NO$_2$S·0.2H$_2$O: C, 49.24; H, 2.69; N, 3.59; S, 8.22; Cl, 27.25. Found: C, 49.08; H, 2.68; N, 3.52; S, 7.95; Cl, 26.92.

Example 69

4-Methyl-3-((2,4,5-trichlorophenyl)thio)-1H-indole-2-carboxylic acid (30b)

Following the method used to prepare 1, the use of 27 (0.15 g, 0.86 mmol) and 67 (0.44 g, 1.03 mmol) provided 0.26 g of product 30b (78%) as an off white solid, mp 260-261° C. $^1$H NMR (300 MHz, DMSO-d$_6$) δ 2.51 (s, 3H), 6.50 (s, 1H), 6.90 (d, J=7 Hz, 1H), 7.23 (t, J=8 Hz, 1H), 7.23 (d, J=8 Hz, 1H), 7.89 (s, 1H), 12.60 (s, 1H), 13.52 (s, 1H). LC-MS (CI): m/z 383.9, 385.9 [(M–H)$^-$ C$_{16}$H$_{10}$Cl$_3$NO$_2$S requires 384.95]. Purity (100%). Calcd for C$_{16}$H$_{10}$Cl$_3$NO$_2$S: C, 49.70; H, 2.61; N, 3.62; S, 8.29; Cl, 27.51. Found: C, 49.49; H, 2.47; N, 3.61; S, 8.56; Cl, 27.29.

Example 70

6-Methyl-3-((2-nitro-4-(trifluoromethyl)phenyl)thio)-1H-indole-2-carboxylic acid (31)

Following the method used to prepare 1, the use of 25 (0.15 g, 0.86 mmol) and 4,4'-bis(trifluoromethyl)-2,2' dinitrodiphenyldisulfide (68) (0.46 g, 1.03 mmol) provided 0.14 g of product 31 (41%) as a yellow solid, mp 238° C. $^1$H NMR (300 MHz, DMSO-d$_6$) δ 2.42 (s, 3H), 6.96-7.00 (m, 2H), 7.33-7.37 (m, 2H), 7.80 (d, J=8 Hz, 1H), 8.51 (s, 1H), 12.51 (s, 1H), 13.50 (s, 1H). LC-MS (CI): m/z 395.0 (M–H)$^-$ C$_{17}$H$_{11}$F$_3$N$_2$O$_4$S requires 396.04]. Purity (100%). Calcd for $C_{17}H_{11}F_3N_2O_4S$: C, 51.52; H, 2.80; N, 7.07; S, 8.09; Cl, 14.38. Found: C, 51.32; H, 2.70; N, 6.93; S, 8.15; Cl, 14.39.

Example 71

Methyl 3-((4-chlorophenyl)thio)-6-fluoro-1H-indole-2-carboxylate (34)

To a solution of impure 1g product (0.19 g, 0.59 mmol) in a mixture of methanol and toluene (6 mL, 1:2) was added TMSCHN$_2$ (2.0 M solution in diethyl ether) (0.6 mL, 1.2 mmol) dropwise under N$_2$. The reaction was allowed to warm to rt and stirred for 2 h. The reaction mixture was concentrated and purified by flash column chromatography eluting with a linear gradient ranging from 0 to 50% EtOAc-hexanes to provide 0.15 g (75%) of product 34 as an off white solid. $^1$H NMR (300 MHz, CDCl$_3$) δ 3.93 (s, 3H), 6.88-6.95 (m, 1H), 7.06-7.16 (m, 5H), 7.45-750 (m, 1H), 9.22 (s, 1H). LC-MS (CI): m/z 336.0 [(M+H)$^+$ $C_{16}H_{11}ClFNO_2S$ requires 335.02].

Example 72

Methyl 6-ethyl-1H-indole-2-carboxylate (37)

Methyl 2-azido-3-(4-ethylphenyl)acrylate (36) (1.0 g, 4.33 mmol) was dissolved in p-xylene and heated at reflux for 3 h. After evaporation of the solvent, the residue was purified by flash column chromatography eluting with a linear gradient ranging from 0 to 20% EtOAc-hexanes to provide 0.52 g (59%) of product 37 as a pale yellow solid. $^1$H NMR (300 MHz, CDCl$_3$) δ 1.28 (t, J=7 Hz, 3H), 2.79 (q, J=7 Hz, 2H), 3.94 (s, 3H), 7.03 (dd, J=2, 8 Hz, 1H), 7.17-7.18 (m, 1H), 7.21-7.23 (m, 1H), 7.60 (d, J=8 Hz, 1H), 8.78 (s, 1H). LC-MS (CI): m/z 202.0 [(M−H)$^-$ $C_{12}H_{13}NO_2$ requires 203.09].

Example 73

6-Ethyl-1H-indole-2-carboxylic acid (38)

Following the method used to prepare 47, the use of 37 (0.52 g, 2.56 mmol) provided 0.45 g (92%) of product 38 as a pale yellow solid. $^1$H NMR (300 MHz, DMSO-d$_6$) $^1$H NMR (300 MHz, CDCl$_3$) δ 1.20 (t, J=7 Hz, 3H), 2.66 (q, J=7 Hz, 2H), 6.94 (d, J=8 Hz, 1H), 7.01-7.03 (m, 1H), 7.22 (s, 1H), 7.54 (d, J=8 Hz, 1H), 11.61 (s, 1H), 12.83 (s, 1H). LC-MS (CI): m/z 188.0 [(M−H)$^-$ $C_{11}H_{11}NO_2$ requires 189.08].

Example 74

3-((3,5-Dichlorophenyl)thio)-6-ethyl-1H-indole-2-carboxylic acid (25)

Following the method used to prepare 1, the use of 38 (125 mg, 0.66 mmol) and 3,3',5,5'-tetrachlorodiphenyl disulfide (54) (266 mg, 0.79 mmol) provided 165 mg of product 25 (68%) as a brown solid, mp 196-199° C. $^1$H NMR (300 MHz, DMSO-d$_6$) δ 1.23 (t, J=8 Hz, 3H), 2.75 (q, J=7 Hz, 2H), 6.99 (d, J=2 Hz, 2H), 7.06 (dd, J=1, 9 Hz, 1H), 7.31-7.34 (m, 2H), 7.38 (d, J=8 Hz, 1H), 12.30 (s, 1H), 13.46 (s, 1H). LC-MS (CI): m/z 364.0, 366.0 [(M−H)$^-$ $C_{17}H_{13}Cl_2NO_2S$ requires 365.0]. Purity (100%). Calcd for $C_{17}H_{13}Cl_2NO_2S$: C, 55.75; H, 3.58; N, 3.82; S, 8.75; Cl, 19.36. Found: C, 55.98; H, 3.61; N, 3.82; S, 8.63; Cl, 19.18.

Example 75

3-((3,5-Dichlorophenyl)thio)-6-methyl-1H-indole-2-carboxylic acid (24)

Following the method used to prepare 1, the use of 25 (0.15 g, 0.85 mmol) and 54 (0.36 g, 1.02 mmol) provided 0.12 g of product 24 (40%) as a brown foam. $^1$H NMR (300 MHz, DMSO-d$_6$) δ 2.42 (s, 3H), 6.97-7.01 (m, 3H), 7.29-7.35 (m, 3H), 12.34 (s, 1H), 13.46 (s, 1H). LC-MS (CI): m/z 350.0, 352.0 [(M−H)$^-$ $C_{16}H_{11}Cl_2NO_2S$ requires 350.99]. Purity (100%). Calcd for $C_{16}H_{11}Cl_2NO_2S$: C, 54.56; H, 3.15; N, 3.98; S, 9.10; Cl, 20.13. Found: C, 54.70; H, 3.24; N, 3.84; S, 8.94; Cl, 19.86.

The synthetic scheme for many of the compounds describe herein are depicted in the following Schemes 3-7:

Scheme 3$^a$

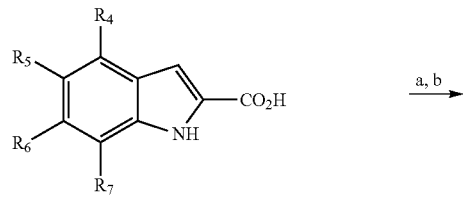

A

A = 25 (compds 1, 18, 18a-g, 19c, 20, 21, 23, 26, 30b, 31)
A = 27 (compds 1a, 19, 19a-b, 30a)
A - 28 (compd 1b)
A = 29 (compds 1c, 21, 30)
A = 30 (compds 1d, 25)
A = 31 (compd 1e)
A = 32 (compd 1f)
A = 33 (compd 1g)
A = 38 (compds 1h, 22, 24)
A = 39 (compd 1i)
A = 40 (compd 1j)

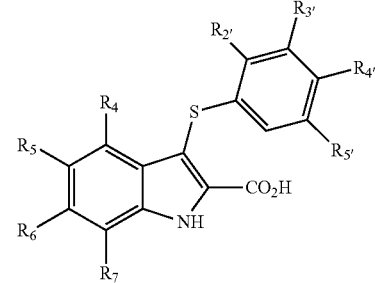

$^a$Reagents and conditions: (a) DMF, 0° C.; (b) NaH, appropriate disulfides 33, 61-67, 69-75, HCl, EtOAc, 50° C. to rt.

Scheme 4$^a$

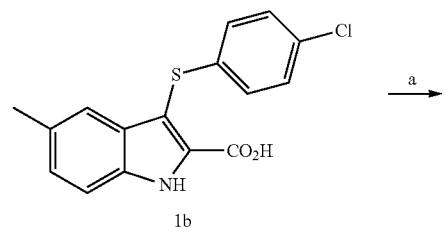

1b

53
-continued

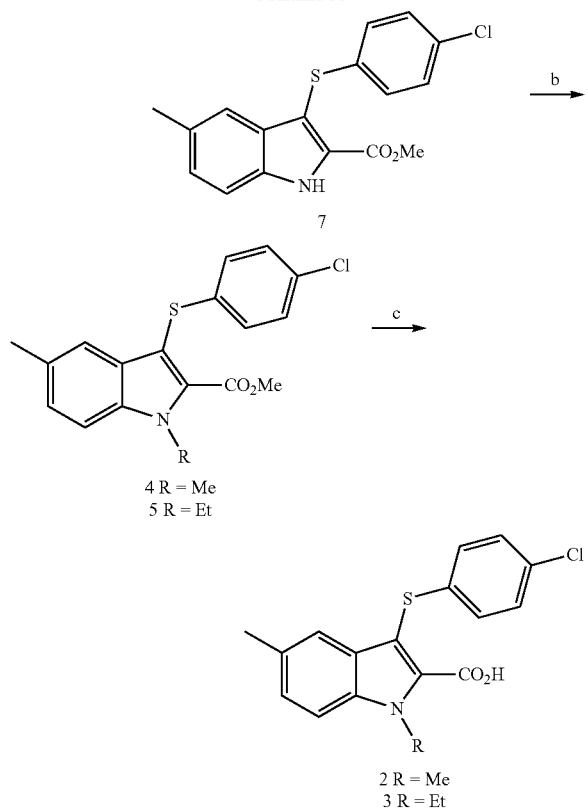

$^a$Reagents and conditions: (a) Oxalyl chloride, MeOH, 0° C.; (b) DMF, NaH, RI, 0° C. to rt; (c) LiOH·H$_2$O, (1:1:1) THF:MeOH:H$_2$O, rt.

Scheme 5$^a$

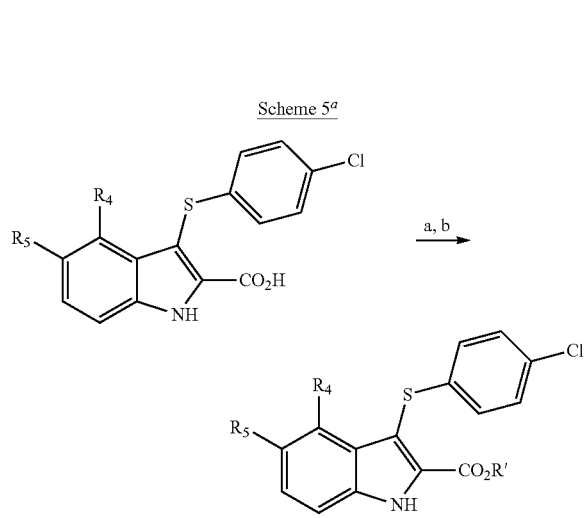

$^a$Reagents and conditions: (a) Oxalyl chloride, CH$_2$Cl$_2$, DMF, 0° C.; (b) ROH, 0° C.

54

Scheme 6$^a$

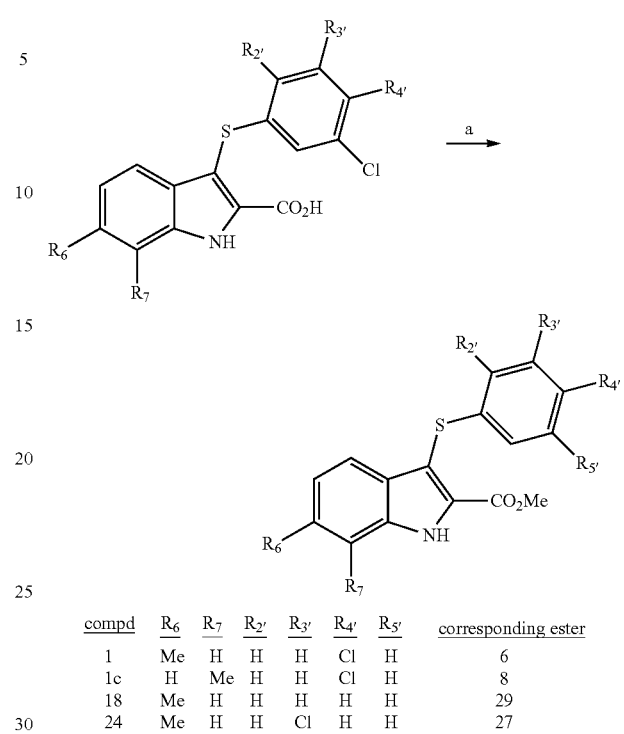

| compd | R$_6$ | R$_7$ | R$_{2'}$ | R$_{3'}$ | R$_{4'}$ | R$_{5'}$ | corresponding ester |
|---|---|---|---|---|---|---|---|
| 1 | Me | H | H | H | Cl | H | 6 |
| 1c | H | Me | H | H | Cl | H | 8 |
| 18 | Me | H | H | H | H | H | 29 |
| 24 | Me | H | H | Cl | H | H | 27 |

$^a$Reagents and conditions: (a) TMSCHN$_2$, MeOH/toluene, rt.

Scheme 7

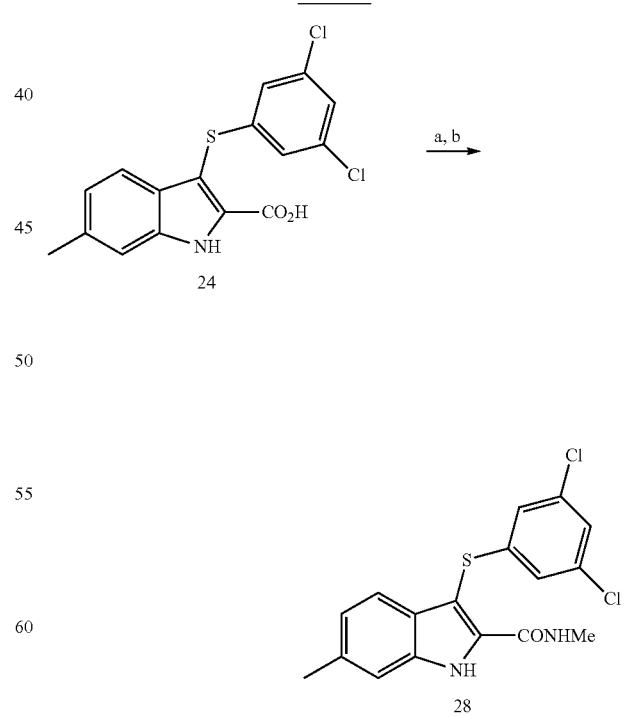

$^a$Reagents and conditions: (a) EDCI, HOBt, DIPEA, rt; (b) MeNH$_2$/THF, rt.

Example 76

Compounds 56-61

TABLE 8

Structures and Chemical Names of Compounds 56-61

| Compound | Structure | Chemical Name | MW |
|---|---|---|---|
| 56 | 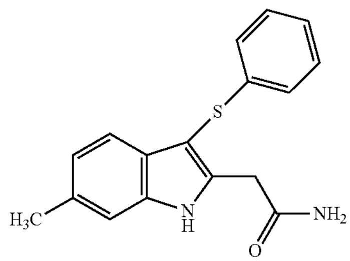 [SMILES: Cc1ccc2c(Sc3ccccc3)c(CC(N)=O)[nH]c2c1] | 2-(6-methyl-3-(phenylthio)-1H-indol-2-yl)acetamide | 296.39 |
| 57 | 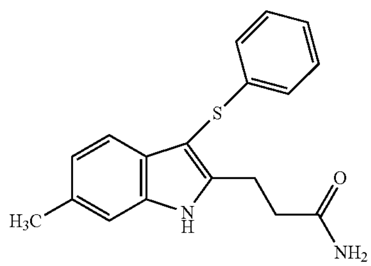 [SMILES: Cc1ccc2c(Sc3ccccc3)c(CCC(N)=O)[nH]c2c1] | 3-(6-methyl-3-(phenylthio)-1H-indol-2-yl)propanamide | 310.41 |
| 58 | 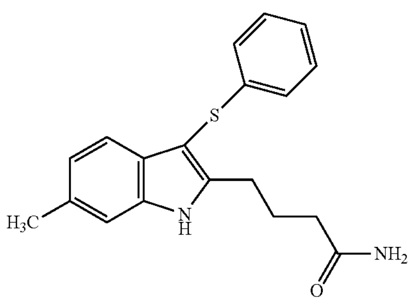 [SMILES: Cc1ccc2c(Sc3ccccc3)c(CCCC(N)=O)[nH]c2c1] | 4-(6-methyl-3-(phenylthio)-1H-indol-2-yl)butanamide | 324.44 |
| 59 | 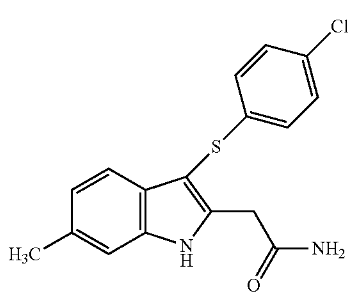 [SMILES: Cc1ccc2c(Sc3ccc(Cl)cc3)c(CC(N)=O)[nH]c2c1] | 2-(3-((4-chlorophenyl)thio)-6-methyl-1H-indol-2-yl)acetamide | 330.83 |
| 60 | 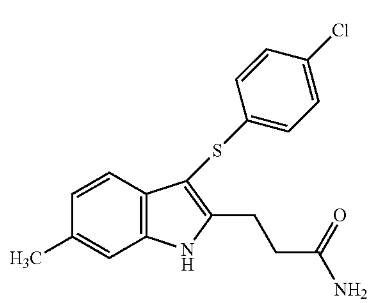 [SMILES: Cc1ccc2c(Sc3ccc(Cl)cc3)c(CCC(N)=O)[nH]c2c1] | 3-(3-((4-chlorophenyl)thio)-6-methyl-1H-indol-2-yl)propanamide | 344.86 |

TABLE 8-continued

Structures and Chemical Names of Compounds 56-61

| Compound | Structure | Chemical Name | MW |
|---|---|---|---|
| 61 | 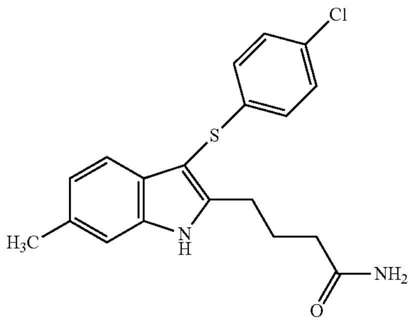 [SMILES: Cc1ccc2c(Sc3ccc(Cl)cc3)c(CCCC(N)=O)[nH]c2c1] | 4-(3-((4-chlorophenyl)thio)-6-methyl-1H-indol-2-yl)butanamide | 358.88 |

Materials and Methods

Reagents, Cells, and Viruses.

Reagents used were purchased from Sigma-Aldrich (St. Louis, Mo.), unless otherwise noted, and used without further purification. African green monkey kidney epithelial cells (BSC-1) were maintained in DMEM supplemented with 10% fetal calf serum (growth medium), 50 µg/mL gentamicin in a humidified incubator at 37° C. and 5% $CO_2$. Cells were not used beyond 10 passages. Vaccinia virus (WR strain) was a kind gift from G. H. Cohen and R. Eisenberg. Recombinant VACV (vL1Ri) was obtained from B. Moss.[26] vL1Ri, under the control of the T7 promoter and lac operator, was propagated in growth medium containing 50 µM isopropyl-β-D-thiogalactopyranoside (IPTG). Compounds were prepared at 100 mM stocks in DMSO. β-actin (mouse, monoclonal) antibody was purchased from Sigma-Aldrich. A4 (rabbit, polyclonal) antibody was a kind gift from G. H. Cohen and R. Eisenberg. E3 (mouse, monoclonal) was generously given by S. N. Isaacs. Bromodeoxyuridine (BrdU), Alexa Fluor 488-conjugated anti-mouse antibody, and ProLong Gold antifade reagent with DAPI were purchased from Life Technologies (Grand Island, N.Y.). Mouse anti-BrdU was purchased from Cell Signaling Technology (Danvers, Mass.).

De Novo Protein Prediction and Molecular Docking.

A20NT100 was obtained through Rosetta de novo structure prediction (Bonneau, et al. *J. Mol. Biol.* 2002, 322, 65-78). D4 was uploaded as a modified version of an X-ray crystallographic structure (PDB accession no. 2OWQ) inserted with missing amino acids from R167 to P173, which corresponded to an unresolved loop (Schormann, et al. *BMC Struct. Biol.* 2007, 7, 45). This prevented a false pocket as the result of the missing residues in the crystal structure. PDB files of A20NT100 and D4 were uploaded to the ICM-Pro software (Molsoft LLC, San Diego, Calif.) for protein-protein molecular docking (Abagyan, et al. *J Comput Chem* 1994, 15, 488-506). The D4 structure was removed of ligands and cofactors, while A20NT100 was subjected to regularization to ensure global energy minimization. Both structures were then converted to ICM objects and docked. The protein conformation of A20NT100-D4 dimer complex to be used as receptor for subsequent compound docking was chosen through the aid of FTMAP (Brenke, et al. *Bioinformatics* 2009, 25, 621-627). The probe set consisted of acetamide, acetonitrile, acetone, acetaldehyde, methylamine, benzaldehyde, benzene, isobutanol, cyclohexane, N,N-dimethylformamide, dimethyl ether, ethanol, ethane, phenol, isopropanol, and urea. Through FTPMAP, A20NT100 and D4 were individually identified of low molecular weight ligand binding sites (Brenke, et al. *Bioinformatics* 2009, 25, 621-627). The sites of ligand clustering, therefore, are identified as hot spots for protein-protein interaction. The docked A20NT100-D4 conformation chosen, thus, contained hot spots within the protein-protein interface to serve as targets for compound design. Compounds were drawn by Symyx Draw 4.0 (Accelrys, San Diego, Calif.) and uploaded to ICM-Pro, where they were parameterized for the docking procedure. Docking "thoroughness" was set at 10.

Viral Plaque Reduction Assay and Cytotoxicity.

Experiments were performed as previously described (Nuth, et al. *J. Med. Chem.* 2011, 54, 3260-7) in triplicates and independently repeated at least twice for the assessment of antiviral activity ($IC_{50}$) and cytotoxicity ($CC_{50}$). Neutral Red was included for cytotoxicity measurements, in addition to LDH.

Microscopy.

Figure 7:
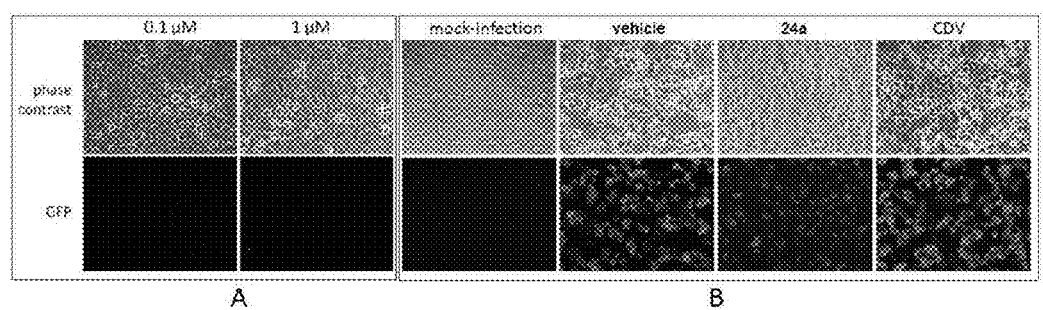
FIG. 7 depicts (A) Potential cytotoxicity of 24a was assessed by treating cells for 9 h with the indicated concentrations. (B) Effects of compounds on EGFP expression by vL1Ri infection.
Figure 10:
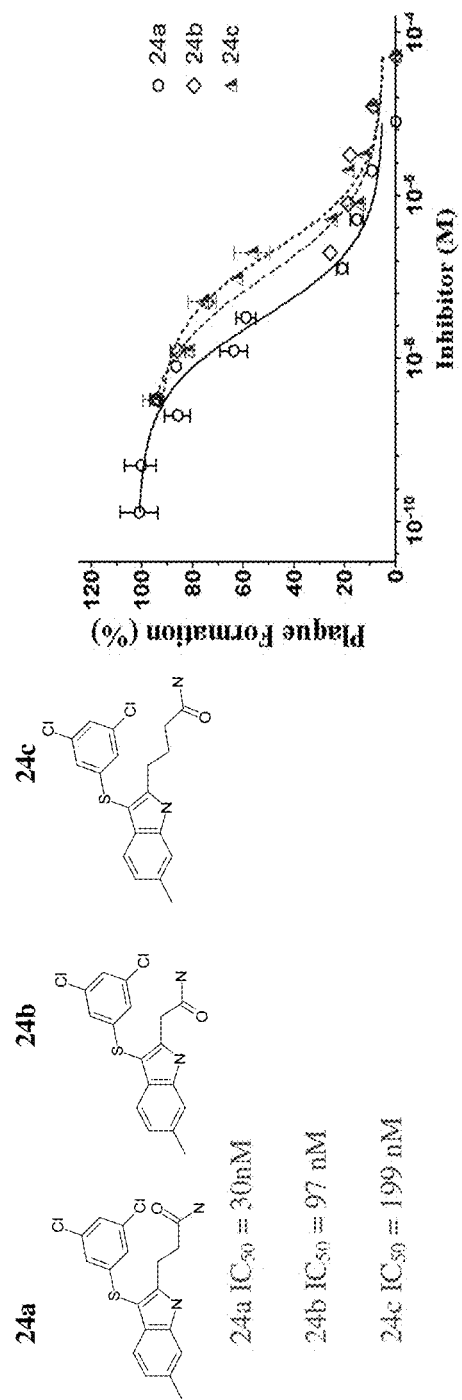
FIG. 10 illustrates an indole-based compounds block mD4-v-hybrid virus infection at low nanomolar concentrations.

BSC-1 cells were seeded at $1.6 \times 10^5$ cells per well in a glass-bottomed 24-well plate (MatTek Corporation, Ashland, Mass.) overnight in 1 mL of growth medium containing 50 µM IPTG. One or 100 µM compound 24a or CDV, respectively, was added to cells for 1 h at 37° C., followed by the addition of vL1Ri at 5 MOI for 1 h at 25° C. Cells were further incubated at 37° C. for an additional 8 h prior to microscopy. DMSO was maintained at 1% for all experiments. Live cells were imaged on a Nikon Eclipse TE2000-U fluorescence microscope (Nikon Instruments Inc., Melville, N.Y.). At least five random fields of view were imaged for each treatment, and experiments were independently repeated. Of note, the treatment with 24a post vL1Ri adsorption (i.e. no compound pre-incubation) still showed appreciable EGFP expression, while CDV showed comparable EGFP expression and CPE to DMSO vehicle (FIG. 7).

BrdU Incorporation Assay.

BSC-1 cells were seeded overnight at $5 \times 10^4$ cells/well on glass coverslips in a 24-well plate. Cells were infected at 1 MOI and either treated with 1% DMSO or 1 µM of compound 24a in the presence of BrdU. At 4 and 8 hpi, cells were fixed with 4% paraformaldehyde in PBS and permeabilized with 0.2% Triton X-100 in PBS. The coverslips were blocked with 3% BSA in PBS for 1 h and stained with mouse anti-BrdU, followed by Alexa Fluor 488-conjugated anti-mouse antibody. The cells were then mounted in ProLong Gold antifade reagent containing DAPI and visualized with a Nikon Eclipse TE300 confocal microscope (Nikon Instruments Inc., Melville, N.Y.) equipped with the LaserSharp2000 software (Bio-Rad, Hercules, Calif.). Three random fields of view were imaged for each treatment, and experiments were independently repeated.

Western Blot Analysis.

BSC-1 cells were seeded overnight in 6-well plates at $8 \times 10^5$ cells/well. Cells were then infected at 1 MOI in 800 μL growth medium/well by adsorbing at 25° C. for 1 h. Compounds were subsequently added to a final volume of 1 mL, and the cells were moved to 37° C. for the indicated time of treatment. Cells were directly washed on the plate with PBS twice, detached by sitting on ice, collected by centrifugation at 1200×g for 10 mM at 4° C., and lysed in RIPA buffer on ice for 1 h. Proteins were resolved by 12% SDS-PAGE, transferred onto a nitrocellulose membrane at 50 V for 1 h, and blocked with 5% nonfat milk in Tris-buffered saline containing 0.05% Tween-20 (TBST). Blots were probed overnight at 4° C. with A4, E3, or β-actin antibody in 5% milk/TBST. Blots were then rinsed thrice with TBST and incubated with to either goat anti-mouse or anti-rabbit IgG-horseradish peroxidase conjugates for 1 h at rt in 5% milk/TBST, followed by rinsing five times with TBST, once with water, and visualized by enhanced chemiluminescence.

Data Analysis.

Half-maximal ($IC_{50}$ and $CC_{50}$) values were obtained by nonlinear regression by fitting to a variable slope, four parameter dose-response model using the Prism software (GraphPad Software, LaJolla, Calif.).

Cytotoxicity Assay

Reagents and Materials

Proteins

Processive DNA synthesis was catalyzed by early-expressed vaccinia proteins from cytoplasmic extracts of BS-C-1 cells infected with the vaccinia virus strain WR. harvested 6 hours after infection. The cytoplasmic extracts were filtered twice through 0.2 mm and contained no infectious particle as shown by plaque assay.

Annealed Primer/Biotinylated Template: synthesized by Integrated DNA Technologies Pimer 20 nucleotides ((5'-GCGAATGAATGACCGCTGAC-3', SEQ ID No. 1) Template 100 nucleotides 5' end biotinylated (5' Biotin-GCACTTATTGCATTCGCTAG TCCACCTTGG ATCTCAGGCT ATTCGTAGCG AGCTACGCGT ACGTTAGCTT CGGT-CATCCC GTCAGCGGTC ATTCATTGGC-3') (SEQ ID NO. 11).

Annealing: 15 nmoles (92 mg) of primer and 15 nmoles (470 mg) of template are mixed in 1.5 mL PBS (pH 7.3), and annealed by heating to 90 C for 5 minutes, then cooled to room temperature. The final P/T concentration is 10 mM or 10 pmole/mL.

SigmaScreen Streptavidin coated plates; 384-well, clear (Sigma cat# S8686-100EA); Digoxigenin-11-2'-deoxy-uridine-5'-triphosphate (DIG-11-dUTP), alkali-stable, 1 mM (Roche cat #11 570 013 910); Deoxynucleotide Triphosphate Set, PCR Grade, Na-Salt, 100 mM (Roche cat #11969064001); Anti-Digoxigenin-POD, Fab fragments from sheep (Roche cat #11 207 733 910); 2,2'-Azino-bis-(3-ethylbenzthiazoline-6-sulfonic acid)diammonium salt (ABTS), (Roche cat #10 102 946 001) dissolved in ABTS buffer (Roche cat #11 112 597 001) at 1 mg/mL; Blocking reagent (Roche, Cat #11 096 176001) 10% (w/v) in maleic acid buffer (0.1 M maleic acid, 0.15 M NaCl, pH to 7.5) diluted 1:10 in PBS to 1% (w/v) final. Stop: 2% SDS, 50 mM EDTA, 10 mM Tris pH8

Wash: PBS+0.1% Tween-20

Vaccinia Virus-Infected Cytoplasmic Lysate and In Vitro Translated Proteins

Throughout the study, thymidine kinase (TK) deficient strain of vaccinia virus, provided by Drs. G. Cohen and R. Eisenberg, was used to infect BSC-1 cells (34). Vaccinia virus-infected cell lysate was prepared as previously described (16). Briefly, the cells were infected at a multiplicity of infection of 15. The vaccinia-infected cells were incubated at 37° C. for 6 h in the presence of hydroxyurea, then harvested by scraping and pelleted at 500 rpm. The pellet was washed with phosphate-buffered saline (PBS) followed by hypotonic buffer (10 mM Hepes, 1.5 mM MgCl2, 10 mM KCl). The cells were then Dounce homogenized and centrifuged at 15,000 rpm for 30 mM The cell suspension was passed through a 2 micron filter to remove the viral cores and nuclear particles. At this point, the vaccinia-infected cytoplasmic lysate was stored in −80° C. in the presence of 20% glycerol. Vaccinia E9, A20 and D4 proteins were translated in vitro as previously described (34). The proteins were expressed from pcDNA3.2/v5 (Invitrogen) in vitro using Promega TNT coupled transcription/translation system. The translation reactions were labeled with [35S]-methionine, fractionated on 10% SDS-PAGE, and visualized by autoradiography.

DNA Synthesis Inhibition Assay

A rapid plate DNA synthesis assay (19) was performed using optimized conditions. Briefly, a 1.2:1 ratio of a 20-mer oligonucleotide primer (5'-GCGAATGAATGACCGCT-GAC-3', SEQ ID No. 1) and a 5'-end biotinylated 100-mer oligonucleotide template (5'-Biotin-AGCACTATTGACAT-TACAGAGTCGCCTTGGCTCTCTGGCTGT-TCGTTGCGGGCTCCG CG TGCGTTGGCTTCG-GTCGTCCCGTCAGCGGTCATTCATTGGC-3') (SEQ ID No. 2) were annealed and loaded into a 96-well microtiter streptavidin-coated plate (Streptawell plates, Roche Applied Science, Indianapolis, Ind., USA) at 5 pmol/well. The wells were incubated at 37° C. for 90 mM, and washed with 100 μL PBS. The reaction was conducted in low salt buffer (20 mM Tris-HCl pH 7.4, 3 mM MgCl2, 0.1 mM EDTA, 0.5 mM DTT, 2% glycerol, 40 ug/mL BSA, 5 uM dNTPs, 1 uM digoxigenin-11-2'-deoxyuridine-5'-triphosphate (DIG-dUTP, Roche Applied Science) with 1 μL vaccinia infected cell lysate or 1 uL of in vitro translated E9 DNA polymerase. The reaction plates were incubated at 37° C. for 30 mM Total DNA synthesis activities were determined through incorporation of DIG-dUTP using a DIG detection ELISA kit (Roche Applied Science) and its substrate 2,2'-azino-bis(3-ethylbenzthiazoline)-sulfonate (ABTS). The plates were read at an absorbance of 405 nm on a microplate reader (Tecan Genius Pro, Tecan US).

Plaque Reduction Assay

African green monkey kidney BSC-1 cells were grown in Dulbecco's modified Eagle medium (DMEM) supplemented with 10% fetal bovine serum (FBS) (Gibco BRL Life Technologies, Gaithersburg, Md.) and 0.1% gentamicin antibiotic at 37° C. in a humidified 5% CO2 environment. Confluent BSC-1 cells were infected with vaccinia virus at an MOI of 0.005 in 48-well plate. The test compounds and control cidofovir were dissolved in DMSO and diluted with the medium. One hour post infection, 400 μL of the test compounds and control were added per well at concentrations ranging from 200 nM to 200 μM and incubated at 37° C. for 16 hours. A 5% solution of formaldehyde in PBS was used to fix the cells. After washing twice with PBS, the plate was stained with 0.2% crystal violet in 50% ethanol.

Cytotoxicity Assay

A cytotoxicity assay that measures the release of glyceraldehydes-3-phosphate dehydrogenase (GAPDH) was conducted using the aCella-TOX bioluminescence cytotoxicity kit (Cell Technology Inc., Mountainview, Calif.), following the manufacturer's protocol. Briefly, BSC-1 cells were grown to confluency in white 96-well cell culture plates at 37° C. in DMEM containing 10% FBS and 0.1% gentamicin in the presence or absence of inhibitor (200 nM to 200 uM). A lysing agent that produces maximum release of GAPDH served as a positive control.

Determination of Therapeutic Index

In determining the cellular therapeutic index, no tests were conducted at concentrations greater than 200 μM due to the limited availability of the compounds and solubility issues at higher stock concentrations. The concentration of inhibitor that causes half of the maximum cell cytotoxicity (CC50) and the concentration that reduces 50% of the plaques (IC50) were used to determine the therapeutics index as follows:

$$\left\{ \text{Therapeuric Index}(TI) = \frac{\text{Cell Cytotoxicity}(CC_{50})}{\text{Inhibitory Concentration}(IC_{50})} \right\}$$

Cell Viability Assays

The cell viability at the plaque IC50 value was performed using two independent methods, cell counting and MTT assay. For the cell counting method, cells were incubated overnight at 37° C. to sub-confluency in 48-well plates. The compounds dissolved in DMSO, were further diluted in media to a final concentration required to achieve the plaque IC50 value. The cells were incubated with the compounds for 24 hrs. The media was removed, the cells trypsinized and stained with tryphan blue, and counted. The MTT assay was also used to confirm to cell viability at the plaque IC50. Cells were seeded at 1.5×104 cells/well in a 96-well plate and incubated overnight at 37° C. at 5% CO2. Compounds dissolved in DMSO were mixed with media to obtain the concentration required to achieve the plaque IC50 value, and incubated with the cells for 16 h. Each well received 20 μL of the MTT solution (5 mg MTT/mL PBS) and the plate was rocked for 5 min. The plates were incubated for an additional 5 h to metabolize MTT, after which the media was removed, and the plates were air dried. To resuspend the formazan, the end product of the MTT assay, 200 μL of DMSO was added to each well and the plates were rocked for 5-10 min Absorbance was read at 560 nm.

Quantitative RT-PCR of Vaccinia Genes

BSC-1 cells in 48-well plates were infected with vaccinia virus at an MOI of 30. The test compounds were added to a final concentration of 20 nM and incubated at 37° C. Infection time points were obtained by removing the media, lysing and scraping the cells into pre-cooled tubes. Total RNA from the samples were isolated using RNeasy mini RNA kit from Qiagen and quantified by measuring the absorbance on Nanodrop (Nanodrop Technologies, Wilmington Del.). Equal aliquot volumes of each sample were reverse transcribed according to Superscript first strand DNA synthesis system (Invitrogen) protocol. Quantitative RT-PCR was performed using LightCycler DNA Master Sybr Green from Roche, and primers designed to probe for early E3, late F9 viral genes and host GAPDH mRNA expression. The levels of expressed viral genes were normalized according to the level of GAPDH. The primer pairs used were: F9L Fwd GGA-CAGTTTAAAAATTGCGCGCTCCG-F9L (SEQ ID No. 3) Rev CGTCTAGATCTATTC CTATTT CTTCAG CGATAGC (SEQ ID No. 4) B5R Fwd CTTCGGATCCAAATGCT-GTCTGCG (SEQ ID No. 5) B5R Rev CGCCGTTGCAACT-TAGTGT CATGGTG (SEQ ID No. 6) E3L Fwd GGAATC-GAA GGAGCTACTGCTGCAC E3L (SEQ ID No. 7) Rev CTTATCCGCCTCCGTTG TCATAAACC (SEQ ID No. 8) gapdh Fwd CCATGGTGAAGGTGAAGACTGC (SEQ ID No. 9) GAPDH Rev CAGCCTTGAC AGTGC CATGG (SEQ ID No. 10). The thermal cycler conditions were 10 min at 95° C., 45 cycles of 5 s at 95° C. followed by 5 s at 60° C. and 5 s at 72° C. All of the samples were assayed in duplicate. A DNA standard calibration curve was plotted using known concentrations of standard cDNA and primers.

Example 77

Compound Optimization of the Indole Moiety

Methyl placement on the indolic benzene at the $R^4$, $R^5$, or $R^7$ position yielded the constitution isomers 1a, 1b, and 1c, respectively, with comparable antiviral activities ($IC_{50}$=46-86 μM) and binding efficiency indices (BEI=12.8-13.0) to 1. The ethyl-substituted 1h and the dimethyl product 1j showed similar profiles. Halide replacement at the $R^6$ methyl did not afford significant activity improvement to the isosteres 1e, 1f, and 1g ($IC_{50}$=40-51 μM) over the parent 1 (Table 1). In contrast, the esterification of the $R^4$ methyl or the complete removal of the methyl group yielded the loss of activity to 1i or 1d, respectively. In sum, these observations indicate, while substitution at the indolic benzene is necessary for function, none of the altered substitution was able to substantially increase inhibition over 1.

The potential contribution by the $R^1$ modification on the indolic pyrrole was examined (Table 1). Since there appeared to be no preference for the site of methyl placement on the indolic benzene, the $R^5$ methyl-substituted analogs for consistency were chosen to focus on. Test compounds 2 ($R^1$=Me) and 3 ($R^1$=Et) represent the acid forms at the pyrrolic $R^2$ position, while 4 ($R^1$=Me) and 5 ($R^1$=Et) are representative methyl esters (Table 1). The $R^1$ ethyl analogs 3 and 5 showed a modest 1.5 and 4-fold improvement in activity ($IC_{50}$=86 and 39 μM) over the corresponding $R^1$ methyl analogs 2 and 4 ($IC_{50}$=135 and 163 μM), respectively, suggesting a potential contribution from the $R^1$ position. However, removal of the $R^1$ functional group led to a more active 6 ($R^1$=H, $R_2$=$CO_2Me$, $IC_{50}$=19 μM), implying the $R^2$ as a better design route than the $R^1$ position. This is further supported by a modest 2-fold improvement in activity of 5 ($R^1$=Et, $R^2$=$CO_2Me$) over 3 ($R^1$=Et, $R^2$=$CO_2H$) (Table 1). To test whether further improvement could indeed be achieved through the $R^2$ modification, straight chain ($CO_2Me$ and $CO_2Et$), branched ($CO_2Pr^i$), and aromatic ($CO_2Ph$ and $CO_2Bn$) esters were generated. While 10-17 were no longer active, the methyl esters 8 and 9 exhibited comparable activities ($IC_{50}$=23 and 21 μM, respectively) to 6 (Table 1), and constitutional isomer of 6, 8, and 9, compound 7 ($R_5$=Me) failed to show activity. The observation shown for 6, 8, and 9, nonetheless, reinforces the $R^2$ position as an important site for compound improvement.

TABLE 1

Structure-activity relationships of compound 1 analogs modified at the indole moiety[a]

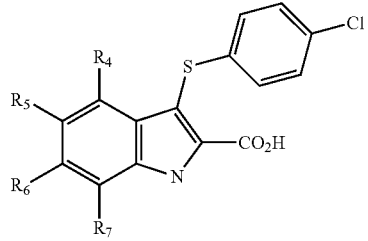

| cmpd | $R_4$ | $R_5$ | $R_6$ | $R_7$ | $IC_{50}$ | $CC_{50}$ | BEI[b] |
|---|---|---|---|---|---|---|---|
| 1 | H | H | Me | H | 82 | 192 | 12.9 |
| 1a | Me | H | H | H | 86 | NA | 12.8 |
| 1b | H | Me | H | H | 46 | 136 | 13.7 |
| 1c | H | H | H | Me | 74 | NA | 13.0 |
| 1d | H | H | H | H | NA | nd | nd |
| 1e | H | H | Cl | H | 47 | 138 | 12.1 |
| 1f | H | H | Br | H | 51 | 90 | 11.2 |
| 1g | H | H | F | H | 40 | NA | 13.7 |
| 1h | H | H | Et | H | 36 | NA | 13.4 |
| 1i | OMe | H | H | H | NA | nd | nd |
| 1j | Me | H | H | Me | 50 | 109 | 13.0 |

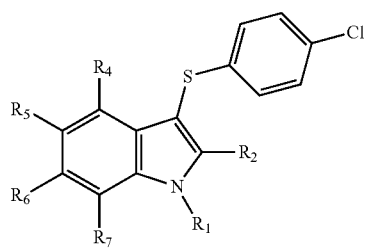

| cmpd | $R_1$ | $R_2$ | $R_4$ | $R_5$ | $R_6$ | $R_7$ | $IC_{50}$ | $CC_{50}$ | BEI[b] |
|---|---|---|---|---|---|---|---|---|---|
| 2 | Me | $CO_2H$ | H | Me | H | H | 135 | NA | 11.7 |
| 3 | Et | $CO_2H$ | H | Me | H | H | 86 | NA | 11.8 |
| 4 | Me | $CO_2Me$ | H | Me | H | H | 163 | NA | 11.0 |
| 5 | Et | $CO_2Me$ | H | Me | H | H | 39 | NA | 12.3 |
| 6 | H | $CO_2Me$ | H | H | Me | H | 19 | 61 | 14.5 |
| 7 | H | $CO_2Me$ | H | Me | H | H | NA | nd | nd |
| 8 | H | $CO_2Me$ | H | H | H | Me | 23 | 32 | 14.0 |
| 9 | H | $CO_2Me$ | Me | H | H | H | 21 | NA | 14.1 |
| 10 | H | $CO_2Et$ | H | Me | H | H | NA | nd | nd |
| 11 | H | $CO_2Et$ | Me | H | H | H | NA | nd | nd |
| 12 | H | $CO_2Pr^i$ | H | Me | H | H | NA | nd | nd |
| 13 | H | $CO_2Pr^i$ | Me | H | H | H | NA | nd | nd |
| 14 | H | $CO_2Ph$ | H | Me | H | H | NA | nd | 12.0 |
| 15 | H | $CO_2Ph$ | Me | H | H | H | NA | nd | nd |
| 16 | H | $CO_2Bn$ | H | Me | H | H | NA | nd | nd |
| 17 | H | $CO_2Bn$ | Me | H | H | H | NA | nd | nd |

[a]Half-maximal values (antiviral $IC_{50}$ and cytotoxicity $CC_{50}$) were determined from triplicate measurements and repeated at least twice. Assays requiring >200 μM of compounds were deemed unreliable due to difficulty in compound solubility and are therefore designated as not active (NA) or otherwise not determined (nd).
[b]The binding efficiency index (BEI) = $pIC_{50}$/MW in kDa.

Example 78

Compound Optimization of the Thiophenyl Ring

For consistency, the $R^2$ position of the indole was maintained as the original acid form (Table 2).

TABLE 2

Structure-activity relationships of compound 1 analogs modified at the thiophenyl ring[a]

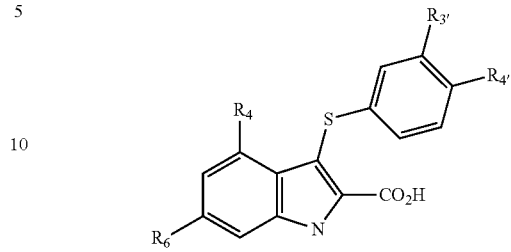

| cmpd | $R_4$ | $R_6$ | $R_{3'}$ | $R_{4'}$ | $IC_{50}$ | $CC_{50}$ | BEI |
|---|---|---|---|---|---|---|---|
| 18 | H | Me | H | H | NA | nd | nd |
| 18a | H | Me | Cl | H | 51 | NA | 13.5 |
| 18b | H | Me | F | H | 69 | NA | 14.1 |
| 18c | H | Me | H | Br | NA | 133 | nd |
| 18d | H | Me | H | Me | NA | nd | nd |
| 18e | H | Me | H | OMe | NA | nd | nd |
| 18f | H | Me | H | $CO_2H$ | NA | nd | nd |
| 18g | H | Me | H | $CF_3$ | 33 | 137 | 12.8 |
| 19 | Me | H | H | OMe | NA | nd | nd |
| 19a | Me | H | H | Me | NA | nd | nd |
| 19b | Me | H | H | $CO_2Me$ | NA | nd | nd |
| 19c | Me | H | H | $NO_2$ | NA | nd | nd |

[a]Assays requiring >200 μM of compounds were deemed unreliable due to difficulty in compound solubility and are therefore designated as not active (NA) or otherwise not determined (nd).

Compound 1 consists of a single chloride at the thiophenyl $R^{4'}$ position. Removal of this chloride atom (compound 18) abolished its antiviral activity (Table 2). The series consisting of 18d, 18e, 19, 19a, and 19b represent test compounds with introduced electron-donating groups Me, OMe, and $CO_2Me$ at the $R^{4'}$ position (Table 2). All failed to show antiviral activities. In contrast, activities were maintained with the electron-withdrawing groups F, and $CF_3$ for 18a, 18b, and 18g, respectively ($IC_{50}$=51, 56, and 33 μM). However, the loss of activity to 18c ($R^{4'}$=Br), 18f ($R^{4'}$=$CO_2H$) and 19c ($R^{4'}$=$NO_2$) may suggest atom type preference. Indeed, the loss of activity by 31 lends credence, since the difference between it and the $CF_3$-containing 18g is the $NO_2$ addition at the $R^{2'}$ position (Table 4).

TABLE 3

Structure-activity relationships of the dichloro analogs[a]

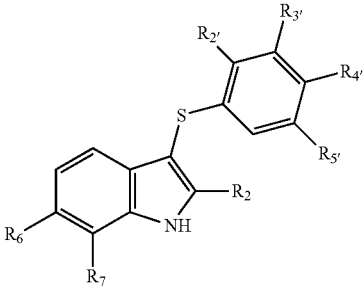

| cmpd | $R_2$ | $R_6$ | $R_7$ | $R_{2'}$ | $R_{3'}$ | $R_{4'}$ | $R_{5'}$ | $IC_{50}$ | $CC_{50}$ | BEI[b] |
|---|---|---|---|---|---|---|---|---|---|---|
| 20 | $CO_2H$ | Me | H | Cl | H | Cl | H | 37 | 129 | 12.6 |
| 21 | $CO_2H$ | Me | H | H | Cl | Cl | H | 34 | 76 | 12.7 |
| 22 | $CO_2H$ | H | Me | H | Cl | Cl | H | 35 | 150 | 12.7 |
| 23 | $CO_2H$ | Et | H | H | Cl | Cl | H | 42 | NA | 11.9 |
| 24 | $CO_2H$ | Me | H | H | Cl | H | Cl | 7 | 75 | 14.6 |
| 25 | $CO_2H$ | Et | H | H | Cl | H | Cl | 9 | 63 | 13.8 |

TABLE 3-continued

Structure-activity relationships of the dichloro analogs[a]

| cmpd | $R_2$ | $R_6$ | $R_7$ | $R_{2'}$ | $R_{3'}$ | $R_{4'}$ | $R_{5'}$ | $IC_{50}$ | $CC_{50}$ | $BEI^b$ |
|---|---|---|---|---|---|---|---|---|---|---|
| 26 | $CO_2H$ | H | H | H | Cl | H | Cl | 43 | 133 | 12.9 |
| 27 | $CO_2Me$ | Me | H | H | Cl | H | Cl | NA | nd | Nd |
| 28 | CONHMe | Me | H | H | Cl | H | Cl | NA | nd | nd |
| 29 | $CO_2Me$ | Me | H | H | H | H | H | 10 | 26 | 16.8 |

[a] Assays requiring >200 μM of compounds were deemed unreliable due to difficulty in compound solubility and are therefore designated as not active (NA) or otherwise not determined (nd).

TABLE 4

Structure-activity relationships of analogs modified at the thiophenyl moiety[a]

| cmpd | $R_4$ | $R_5$ | $R_6$ | $R_7$ | $R_{2'}$ | $R_{4'}$ | $R_{5'}$ | $IC_{50}$ | $CC_{50}^b$ | BEI |
|---|---|---|---|---|---|---|---|---|---|---|
| 30 | H | H | Me | H | Cl | Cl | Cl | 25 | 78 | 11.9 |
| 30a | H | H | H | Me | Cl | Cl | Cl | 21 | 93 | 12.1 |
| 30b | Me | H | H | H | Cl | Cl | Cl | 18 | 65 | 12.3 |
| 31 | H | H | Me | H | $NO_2$ | $CF_3$ | H | NA | nd | nd |

[a] Assays requiring >200 μM of compounds were deemed unreliable due to difficulty in compound solubility and are therefore designated as not active (NA) or otherwise not determined (nd).

Although $F^-$ and $CF_3$ appear to be interchangeable with the parental $Cl^-$, the chloro analogs exclusively was chosen to focus on, largely due to the lack of improvement with either $F^-$ or $CF_3$. As such, the potential to improve activity with increasing number of chloride atoms was interrogated by examining dichloro (Table 3) and trichloro analogs (Table 4). The dichloro compounds 20, 21, 22, and 24 represent constitutional isomers containing the $R^2$ position acid that differ in the indole methyl and thiophenyl chloride attachment, while 30, 30a, and 30b are comparable trichloro constitutional isomers only differing in methyl placement on the indolic benzene. Analogs 30, 30a, and 30b shared similar potency ($IC_{50}$=25, 21, and 18 μM, respectively) and cytotoxicity ($CC_{50}$=78, 93, and 65 μM, respectively) profiles (Table 4). Alternatively, the dichloro analogs 20, 21, 22, and 24 showed approximately 2-11-fold activity improvement ($IC_{50}$=7-37 μM) over the parent 1 (Table 3), thereby prompting to proceed optimization with the dichloro analogs instead of the trichloro substituents. Specifically, chloro substitutions at the $R^{3'}$ and $R^{5'}$ positions appeared responsible for the improved activity of 24 ($IC_{50}$=7 μM) over 20-22 ($IC_{50}$=34-37 μM), which contain chlorides at the $R^{3'}$ and $R^{4'}$ positions (Table 3). Next, the contribution from the $R_6$ position of 24 to compound activity was examined. This was accomplished by the removal or ethyl replacement of the $R^6$ methyl to yield 26 or 25, respectively. While 25 showed comparable activity ($IC_{50}$=9 μM) to 24, ~6-fold decrease in activity ($IC_{50}$=43 μM) was observed for 26 (Table 3), thereby suggesting the contribution of activity from the $R_6$ position. In comparison to 24, both 25 and 26 resulted in slightly lower BEI values (14.6 vs. 13.8 and 12.9, respectively), indicating the $R^6$ methyl to be the preferred route. Moreover, since the requirement of the $R^2$ position for compound function was observed, it was tested whether modification at this position could lead to further improvement, as based on the chemical scaffold of 24. To assess this, the amide analog 28 ($R^2$=CONHMe) was generated, but resulted in the loss of activity (Table 3). Next, a methyl ester 27 was generated, that also led to the loss of activity (Table 3). This was surprising since 27 is the dichloro form of 6, which showed an $IC_{50}$=19 μM (Table 1). Experimentally, an increase in cytotoxicity was observed, which may be responsible for the inability to determine an accurate $IC_{50}$ value. To address whether the chlorides could indeed contribute to cytotoxicity, both thiophenyl chlorides were removed from the scaffold of 24 to generate the methyl ester 29. Within experimental errors, the potency ($IC_{50}$=10 μM) and cytotoxicity ($CC_{50}$=26 μM) profiles were observed to be comparable to 24 (Table 3). Taken together, an internal amide at the $R^2$ position does not appear to be tolerated, while compound improvement is not supported by the additional chloride. In agreement, the monochloro 6 and dichloro 24 showed similar BEI values (14.5 vs. 14.6, respectively). Moreover, no increase in cytotoxicity is observed with the additional chloride. So with respect to the loss of activity observed for 27, there might be an imparting of electronic properties of the chlorides onto the $R^2$ ester as to render the compound less active. In proceeding with compound design, 29 (BEI=16.8), along with 6 and 24, serve as desirable scaffolds.

Example 79

Compound Selection

In an attempt to select a compound amenable for further improvement, the binding efficiency index (BEI) as a useful index was considered. Proposed by Abad-Zapatero and Metz (Abad-Zapatero, et al. *Drug Discov. Today*, 2005, 10, 464-469), the BEI ($pIC_{50}$/MW) serves as a useful metric for compound optimization. With BEI values of 14.5, 14.6, and 16.8, compounds 6, 24 and 29 represent the highest ranked compounds, respectively, among the 57 analogs synthesized. Since the $pIC_{50}$ term in the BEI calculation corresponds to antiviral activity, these three compounds, therefore, reflect leads with high potency. Notably, all three compounds exhibited comparable cytotoxicity profiles. In the current study, compound 24 was chosen to develop mainly due to the apparent increase in compound solubility as the result of the introduced chlorides, since many of these indole analogs tend to exhibit poor solubility as to become problematic for in vitro experiments.

Example 80

Design of A20 and the A20-D4 Heterodimer

While A20 has been recently shown to play a critical role in processive DNA synthesis of vaccinia virus (Klemperer, et al.

J. Virol. 2001, 75, 12298-12307; Stanitsa, et al. J. Biol. Chem. 2006, 281, 3439-3451; and Druck Shudofsky, et al. J. Virol. 2010, 84, 12325-12335), there is a lack of biochemical and structural information. Moreover, the problems associated with A20 protein expression remains elusive. Since standard sequence homology-based structure design proved unsuccessful, a de novo approach was undertaken by way of the Rosetta procedure, which allows for the prediction of low energy global conformations built from energy minimized ensemble of local structure fragments (Bonneau, et al. J. Mol. Biol. 2002, 322, 65-78; Bonneau, et al. Proteins 2001, 43, 1-11; and Simons, et al. Proteins 1999, 34, 82-95).

Figure 6:
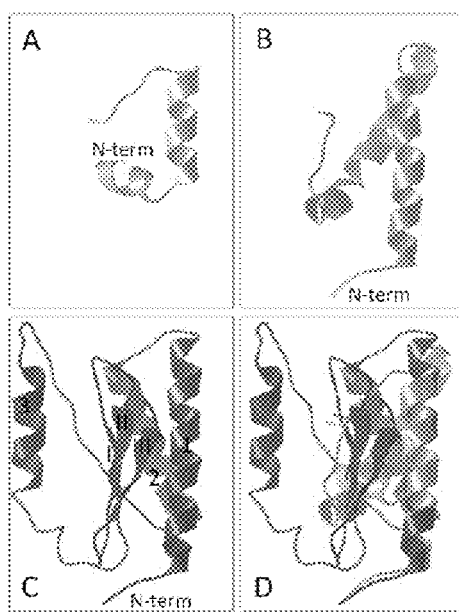
FIG. 6 depicts a De novo design of A20. Protein conformations of the N-terminal 25 (A), 50 (B), and 100 (C) amino acid residues of A20 were obtained through the Rosetta structure prediction by way of the Robetta server (http://robetta.bakerlab.org). α-helices (1-3) and β-sheets (I-III) are shown. (D) Superimposition of the three structures.

The increasing length of A20 (starting from the N-terminus) was examined for protein fold. Peptides consisting of 25, 50, and 100 amino acids were superimposable (FIG. 6). The N-terminal 100-amino acid peptide of A20 (hereafter referred to as A20NT100) was chosen to focus on largely due to the inclusion of residues shown necessary for D4 binding (Ishii, et al. Virology 2002, 303, 232-239). In addition, the protein fold, consisting of three peripheral helices and a potential core made up of three O-sheets (FIG. 6B), appears contiguous and undisruptive (FIG. 6). Increased chain length led to increasing loss of superimposition of structures, as well as the failure of the prediction by the Rosetta procedure (data not shown). A20NT100 was next docked with the crystallographic form of D4 (Schormann, et al. BMC Struct. Biol. 2007, 7, 45). The choice of docked pose was aided with the help of FTMAP, a computational fragment-based approach that uses a fast Fourier transform correlation technique to identify low molecular weight ligand binding sites (Brenke, et al. Bioinformatics 2009, 25, 621-627. Thus, hot spots represent regions where the ligands cluster and are potential druggable sites. A20NT100 and D4 were individually subjected to FTMAP, and the conformation of the heterodimer chosen was the highest ranked pose identified by ICM-Pro ($-40.3$ kcal mol$^{-1}$ binding energy) which bears two hot spots on the A20N100 surface and one on the D4 surface at the protein-protein interface (FIG. 1C). The interface is brought about largely through contacts of the C-terminal region of D4, encompassing residues 159-204, with the middle region of A20NT100, consisting mainly of residues of helix 2 (FIG. 1B and Table 6). The docked protein complex served as receptor for subsequent interrogation of compound binding.

Example 81

Design, Synthesis and Antiviral Activity of Compound 21a

The docking of Compound 1 and analog 24 to the A20NT100-D4 heterodimer was localized to a newly formed pocket nearby the opening of the heterodimer interface with residues P68 of A20NT100 and R193 of D4 within proximity (FIG. 1D). Both compounds are superimposable, with the thiophenyl ring seemingly solvent exposed and exhibiting favorable docking scores of $-50.0$ and $-46.6$ kcal/mol for 1 and 24, respectively (FIG. 1D and Table 7). Due to the importance of the pyrrolic $R^2$ position for compound activity, the $R^2$ position formate of 24 was replaced with a propanamide, producing 24a (Scheme 1). Significantly, in a viral plaque reduction assay, 24a exhibited a dramatic improvement in antiviral activity ($IC_{50}$=42 nM) (Table 4). The docking of 24a yielded a pose similar to 1 and 24, but with an improved score of $-62.8$ kcal/mol. Since the docking procedure assumes a rigid body receptor, it is unlikely the score reflects the ability of the propanamide extension to disrupt the protein-protein interface. Nevertheless, the pose suggests the proximity of the terminal amide to residues P68 of A20NT100 and R193 of D4.

Example 82

Figure 3:
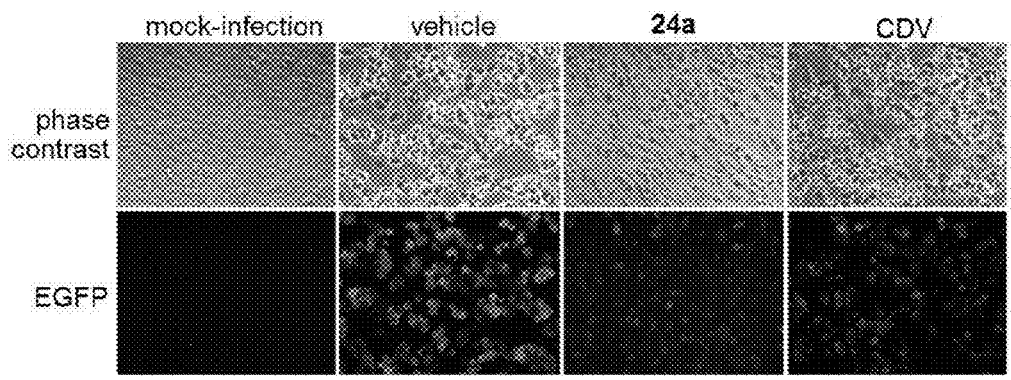
FIG. 3 depicts the blocking of late reporter gene expression by 24a. Live-cell microscopy of BSC-1 cells infected with vL1R1 (MOI=5) at 8 hpi. Cells were pretreated for 1 h with either 1 or 100 μM compound 24a or CDV, respectively, prior to virus adsorption, and visualized with 10× objectives. Vehicle was DMSO maintained at 1% throughout experiments. Images are representatives of at least five random fields of view.

Compound 24a Inhibits Late Viral Gene Expression that is Consistent with a Block in Viral DNA Synthesis Unlike early VACV genes, expression of late genes is dependent upon viral DNA synthesis. Since A20 and D4 are critical components of the DNA replication machinery, the ability of 24a to inhibit late viral gene expression was tested by using a recombinant VACV (vL1Ri)$^{26}$ that encodes the EGFP marker under the control of a synthetic early/late promoter. Indeed, 24a (at 1 µM) significantly reduced EGFP expression at 8 h post-infection (hpi), a time at which the EGFP signal is normally amplified due to the increase in viral DNA replication (FIG. 3). In comparison, the chain terminator, cidofovir (CDV), was equally effective at a higher dose (100 µM). Notably, a lowered cytophathic effect (CPE) was observed for 24a treatment, compared to either vehicle or CDV treatments.

Figure 4:
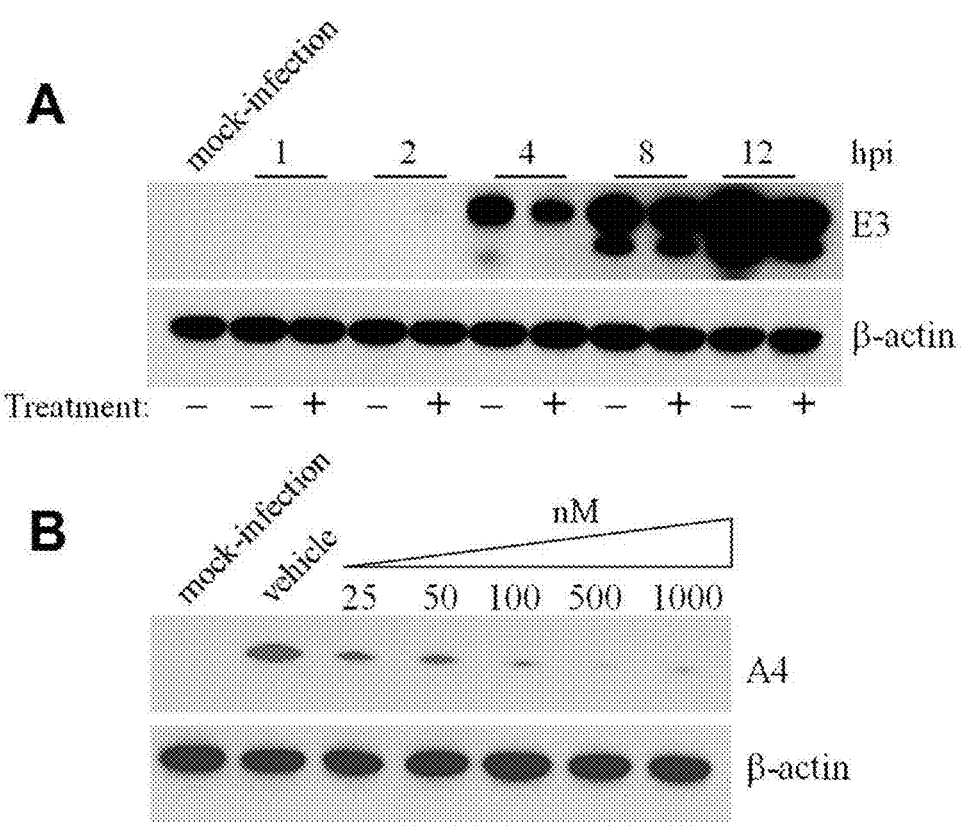
FIG. 4 depicts the blocking of late, but not early, viral marker proteins by 24a. (A) Western blot analysis of the temporally early-expressing gene product E3. Treatment was performed with 1 μM of compound 24a. (B) Western blot analysis of the temporally late-expressing gene product A4 at 12 hpi after treatment with increasing doses of 24a. Cells were infected at 1 MOI. Vehicle was 1% DMSO.

To further assess the inhibition of viral DNA synthesis by 24a, the levels of actual early and late vaccinia virus marker proteins were compared. First the response to 24a was examined by the early protein encoded by the E3L gene, which is an inhibitor of dsRNA-binding in immune evasion (Chang, et al. Proc. Natl. Acad. Sci. U.S.A. 1992, 89, 4825-4829). The E3 protein was detectable at 4 hpi (an early time point), with further accumulation at 8 and 12 hpi (late time points) (FIG. 4A). Only a slight decrease in protein level was observed following treatment with 1 µM of compound 24a at 8 hpi (FIG. 4A). As a marker of late gene expression, the product of the A4L gene was examined, which is present in the viral core (Maa, et al. J. Virol. 1987, 61, 3910-3919) and is associated with morphogenesis (Risco, et al. Virology 1999, 265, 375-386). As seen in FIG. 4B, at a late time-point of infection (12 hpi), the levels of A4 protein in 24a treated cells were dramatically reduced in a dose-dependent manner (FIG. 4B). These experiments clearly demonstrate that 24a prevents late gene expression, while exhibiting minimal effects on early gene expression, which is consistent with its ability to block viral DNA synthesis.

Example 83

Compound 24a Inhibits Vaccinia Virus Replication

Figure 5:
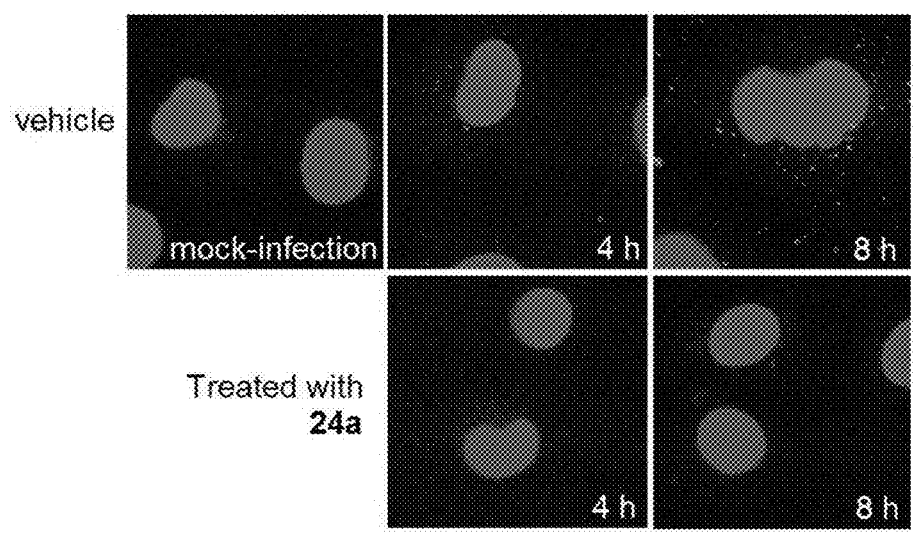
FIG. 5 depicts an inhibition of viral DNA replication by 24a. BrdU incorporation (green) in cells treated with 1 μM of compound 24a at 4 and 8 hpi (MOI=1). Nuclei were stained with DAPI (blue). Vehicle was DMSO maintained at 1% throughout experiments. Images were visualized with 60× objectives and are representatives of at least three random fields of view.

Poxviruses are unusual in that they replicate in the cytoplasm, where they are visualized as focal sites of DNA replication, often referred to as viral factories. In order to to directly examine the effect of 24a on viral replication, its ability to prevent incorporation of bromodeoxyuridine (BrdU) into viral DNA was examined. As seen in FIG. 5, BrdU labeling was localized to viral factories in untreated treated cell, but was significantly suppressed in infected cells treated with 24a. This preclusion of BrdU incorporation by 24a is consistent with the ability of this analog to block viral DNA synthesis and replication.

Example 84

Amide Requirement at the Pyrrolic $R_2$ Position

The docked pose of 24a suggests the potential interaction of the propanamide with the nearby residues P68 of A20NT100 and R193 of D4 (Scheme 1, inset). Since 24 is an acid at the pyloric $R^2$ position, it was hypothesized that, in addition to the potential contribution of the propanamide extension of 24a in comparison to the formate of 24, the improvement in activity may be due to the H-bond donating and accepting properties of the terminal amide. As such, it was reasoned that the stabilization of 24a might be achieved through newly formed H-bond pairing. To explore this possibility, the propanoic acid precursor 24d was synthesized and examined for antiviral activity (Scheme 1). An approximate 5-fold decrease in potency ($IC_{50}$=244 nM) by 24d indicates that the terminal amide is preferred (Table 5), whereby weaker charge and/or van der Waals contributions may compensate for the loss of the amide nitrogen. Since H-bond requires distant constraint, compound 24a was shortened or lengthened by a methylene to generate the alkylamide analogs 24b or 24c, respectively (Scheme 2). While the butanamide analog 24c showed ~5-fold loss of activity ($IC_{50}$=208 nM), the acetamide analog 24b retained an activity ($IC_{50}$=46 nM) comparable to 24a. Compound 24b (BEI=20.1) represents an improvement of 5.4 units over the parent 1 (BEI=14.7) (Table 5). Since the BEI contains a logarithmic term, this represents several orders of magnitude improvement of the design. Lastly, compound 24e, the N-hexylation product of 24a (Scheme 1), showed a complete loss of activity (Table 5). Taken together, the hypothesis of a mechanism by which H-bond contributes to the improvement of compound activity is supported. However, a small set of analogs is limited and therefore cannot rule out other potential chemical contributions. In addition, applying similar $R^2$ position alkylamide modifications to scaffold 29 was to be tested to see if similar improvements are achieved. With a BEI value of 16.8, it represents an attractive starting point. Also, with respect to cytotoxicity, 24a and 24b represent the top two compounds with the highest selectivity indices (SI=374 and 570, respectively). As such, it was assessed whether improvement to cytotoxicity by 24a and 24b could be achieved by removal of the chlorides similarly to 29.

TABLE 5

Structure-activity relationships of compound 24 analogs[a]

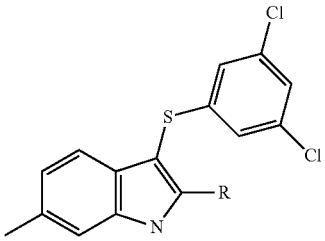

| cmpd | R | $IC_{50}$ (nM) | $CC_{50}$ (µM) | BEI | SI[b] |
|---|---|---|---|---|---|
| 24 | 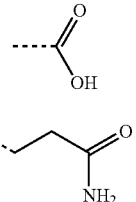 | 7000 ± 1460 | 75 | 14.7 | 11 |
| 24a | 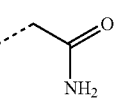 | 42 ± 16 | 16 ± 5 | 19.5 | 374 |
| 24b | 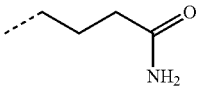 | 46 ± 10 | 26 ± 3 | 20.1 | 570 |
| 24c | 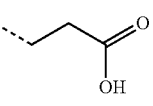 | 208 ± 42 | 243 ± 2 | 17.0 | 115 |
| 24d | 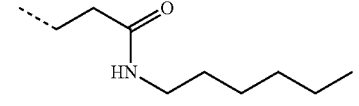 | 244 ± 27 | 36 ± 14 | 17.4 | 152 |
| 24e |  | NA | 27 ± 4 | nd | nd |

[a]Assays requiring >200 µM of compounds were deemed unreliable due to difficulty in compound solubility and are therefore designated as not active (NA) or otherwise not determined (nd). Values are reported as mean ± SEM of triplicates of at least two independent repeats.
[b]The selectivity index (SI) = $CC_{50}/IC_{50}$.

Example 85

De Novo A20 Design and Molecular Docking

The structure of the N-terminal 100 amino acid stretch was designed de novo by way of the Rosetta procedure. The first 25 amino acids adopted a protein fold consisting of two shorten helices. The increase of an additional 25 amino acids extends on the same two helices, while further increase to a total of 100 amino acids introduces a third helix and three discernible β-sheets. The inclusion of 100 amino acid residues yielded a more complete tertiary structure, whereby the three β-sheets are surrounded by the three α-helices. By contrast, the N-terminal 50 amino acid construct appeared flexible, and likely unstable. Indeed, protein preparations resulted in inclusion bodies and not capable of in vitro refolding (M.N., observations).

For protein docking, PDB files of the N-terminal 100 amino acid protein of A20 (A20NT100) (FIG. 6C) and the modified version of the X-ray crystallographic structure of D4 (PDB accession no. 2OWQ) were uploaded to ICM-Pro for molecular docking. The highest ranked pose for the protein-protein interaction yielded a binding energy of −40.31 kcal/mol through contact residues shown in Table 6. A new PDB coordinate was generated from this particular pose and subsequently used as receptor for compound binding. Binding energies for the analogs of compound 24 are shown in Table 7. Not shown in the table and for comparison, the monochloro parent 1 had a score of −45.94 kcal mol$^{-1}$.

TABLE 6

Residues implicated in protein contacts. Using the docked complex, protein contacts between A20NT100 and D4 were analyzed by the ICM-Pro software.

| | Residue | Corresponding Contact Area (Å$^2$) |
|---|---|---|
| A20NT100 | T39, Y42, E36, I28, P68 | 63.75, 55.07, 46.92, 45.59, 43.68 |
| | F69, V47, Y31, N32, K67 | 41.71, 37.08, 32.02, 16.74, 12.9 |
| | V50, S40, N66, Q48, V35 | 12.54, 10.76, 10.36, 9.038, 8.16 |
| | K44, K49, W43 | 7.304, 6.931, 3.423 |
| D4 | P173, K160, S164, L201, I197 | 72.62, 70.58, 35.43, 32.69, 30.49 |
| | L170, V178, I177, T176, V174 | 28.56, 22.34, 20.77, 16.39, 14.36 |
| | T161, L204, T175, R167, K169 | 12.86, 11.65, 11.27, 11.21, 9.127 |
| | N165, E171, F163, I166, A168 | 8.773, 8.522, 7.622, 4.769, 4.757 |
| | S172, V200, Y180, G159 | 3.461, 3.457, 0.6301, 0.2378 |

TABLE 7

Molecular docking scores for analogs of compound 24

| Compound | R | Binding energy (kcal/mol) |
|---|---|---|
| 24 | —C(=O)OH | −46.63 |
| 24a | —CH$_2$C(=O)NH$_2$ | −62.85 |
| 24b | —C(=O)NH$_2$ | −56.06 |
| 24c | —CH$_2$CH$_2$C(=O)NH$_2$ | −67.56 |
| 24d | —CH$_2$C(=O)OH | −56.69 |
| 24e | —CH$_2$C(=O)NH(CH$_2$)$_5$CH$_3$ | −87.97 |

Example 86

Inhibition of DNA Synthesis by Compound 24a and Cidofovir

As was shown in FIG. 3, it was observed that the pretreatment of cells with 24a for 1 h prior to virus adsorption yielded a more pronounced effects on the EGFP expression. Even so, suppression of EGFP was still observed when treated with 1 µM of 24a after 1 h virus adsorption (FIG. 7B). However, Cidofovir, which clearly showed suppression of EGFP when pretreated (FIG. 3), exhibit EGFP expression comparable to vehicle-treatment (FIG. 7B). In addition, minimal cytotoxicity due to 24a was observed within the experimental time frame (FIG. 7A). Taken together, the improved effectiveness of the compounds as the consequence of cell pretreatment may likely be due to the permitting of adequate time for compound permeation into cells.

In FIG. 7, cells were infected at 5 MOI with vL1Ri for 1 h at 25° C., followed by the exchange to media containing either 1 or 100 µM of compound 24a or cidofovir (CDV), respectively. Cells were further incubated at 37° C. for an additional 8 h prior to live-cell microscopy. Cells were seeded overnight at 0.16×10⁶ BSC-1 cells/well in a glass-bottom 24-well plate (MatTek Corporation, Ashland, Mass.) in DMEM supplemented with 10% FBS and 50 μg/mL gentamicin and cultured in a humidified chamber at 5% $CO_2$ atmosphere at the indicated temperatures. Vehicle was DMSO maintained at 1% for all experiments. Live cells were imaged on a Nikon Eclipse TE2000-U fluorescence microscope using a 10× objective.

Example 87

Protein Sequence Alignment

Protein sequences of A20 (FIG. 8) and D4 (FIG. 9) from vaccinia virus were compared to other orthopoxviruses (VARV, MPXV, and CPXV), molluscipox (MCV), and herpesvirus (EBV) members.

Example 88

Compounds 24a, 24b, and 24c Target the MCV mD4 Protein to Block Infection (Plaque Formation) at Very Low Nanomolar Concentrations Experimental Details:

When Compounds 24a, 24b, and 24c were tested for their abilities to block infection of the mD4-VV hybrid virus. The mD4-VV hybrid virus is vaccinia pox virus in which the vaccinia D4 encoding viral gene (vD4) has been replaced with the Molluscum Contagiosum Virus (MCV) D4 encoding viral gene (mD4). These compounds also proved to be extremely potent inhibitors of the mD4-VV hybrid virus with $IC_{50}$ values in the low nanomolar concentration, specifically: 24a=30 nM; 24b=97 nM; and 24c=199 nM. Significantly, since each of these indole-based compounds were able to block processive DNA synthesis in our in vitro Rapid Plate Assay (U.S. Pat. No. 6,204,028) requiring only the protein triad (mD4, vE9 and vA20) and since E9 was shown not to an E9 Pol inhibitor (101), it became apparent that these indole-based compounds are targeting D4/A20. In accord with this conclusion, is that the rational drug design that led to an increased potency of the original parental Lead compound>2,000-fold, was based on a model in which 24a 'sandwiches' between the docked interface of the D4 and A20 proteins. Thus, the data indicate that the mechanism of action of these indole-based compounds is that they act to disrupt a critical interaction between mD4 and mA20.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: PCR PRIMER

<400> SEQUENCE: 1
gcgaatgaat gaccgctgac                                              20

<210> SEQ ID NO 2
<211> LENGTH: 100
<212> TYPE: DNA
<213> ORGANISM: Artificial Sequence
<220> FEATURE:
<223> OTHER INFORMATION: PCR PRIMER

<400> SEQUENCE: 2
agcactattg acattacaga gtcgccttgg ctctctggct gttcgttgcg ggctccgcgt    60
gcgttggctt cggtcgtccc gtcagcggtc attcattggc                        100

<210> SEQ ID NO 3
<211> LENGTH: 26
<212> TYPE: DNA
<213> ORGANISM: Artificial Sequence
<220> FEATURE:
<223> OTHER INFORMATION: PCR PRIMER

<400> SEQUENCE: 3
ggacagttta aaaattgcgc gctccg                                        26

<210> SEQ ID NO 4
<211> LENGTH: 34
<212> TYPE: DNA
```

```
<213> ORGANISM: Artificial Sequence
<220> FEATURE:
<223> OTHER INFORMATION: PCR PRIMER

<400> SEQUENCE: 4
cgtctagatc tattcctatt tcttcagcga tagc                              34

<210> SEQ ID NO 5
<211> LENGTH: 24
<212> TYPE: DNA
<213> ORGANISM: Artificial Sequence
<220> FEATURE:
<223> OTHER INFORMATION: PCR PRIMER

<400> SEQUENCE: 5
cttcggatcc aaatgctgtc tgcg                                         24

<210> SEQ ID NO 6
<211> LENGTH: 26
<212> TYPE: DNA
<213> ORGANISM: Artificial Sequence
<220> FEATURE:
<223> OTHER INFORMATION: PCR PRIMER

<400> SEQUENCE: 6
cgccgttgca acttagtgtc atggtg                                       26

<210> SEQ ID NO 7
<211> LENGTH: 25
<212> TYPE: DNA
<213> ORGANISM: Artificial Sequence
<220> FEATURE:
<223> OTHER INFORMATION: PCR PRIMER

<400> SEQUENCE: 7
ggaatcgaag gagctactgc tgcac                                        25

<210> SEQ ID NO 8
<211> LENGTH: 26
<212> TYPE: DNA
<213> ORGANISM: Artificial Sequence
<220> FEATURE:
<223> OTHER INFORMATION: PCR PRIMER

<400> SEQUENCE: 8
cttatccgcc tccgttgtca taaacc                                       26

<210> SEQ ID NO 9
<211> LENGTH: 22
<212> TYPE: DNA
<213> ORGANISM: Artificial Sequence
<220> FEATURE:
<223> OTHER INFORMATION: PCR PRIMER

<400> SEQUENCE: 9
ccatggtgaa ggtgaagact gc                                           22

<210> SEQ ID NO 10
<211> LENGTH: 20
<212> TYPE: DNA
<213> ORGANISM: Artificial Sequence
<220> FEATURE:
<223> OTHER INFORMATION: PCR PRIMER

<400> SEQUENCE: 10
cagccttgac agtgccatgg                                              20
```

```
<210> SEQ ID NO 11
<211> LENGTH: 100
<212> TYPE: DNA
<213> ORGANISM: Artificial Sequence
<220> FEATURE:
<223> OTHER INFORMATION: PCR TEMPLATE

<400> SEQUENCE: 11
gcacttattg cattcgctag tccaccttgg atctcaggct attcgtagcg agctacgcgt    60
acgttagctt cggtcatccc gtcagcggtc attcattggc                        100

<210> SEQ ID NO 12
<211> LENGTH: 426
<212> TYPE: PRT
<213> ORGANISM: Vaccinia virus

<400> SEQUENCE: 12

Met Thr Ser Ser Ala Asp Leu Thr Asn Leu Lys Glu Leu Leu Ser Leu
1               5                   10                  15

Tyr Lys Ser Leu Lys Phe Ser Asp Ser Ala Ala Ile Glu Lys Tyr Asn
                20                  25                  30

Ser Leu Val Glu Trp Gly Thr Ser Thr Tyr Trp Lys Ile Gly Val Gln
            35                  40                  45

Lys Val Ala Asn Val Glu Thr Ser Ile Ser Asp Tyr Tyr Asp Glu Val
    50                  55                  60

Lys Asn Lys Pro Phe Asn Ile Asp Pro Gly Tyr Tyr Ile Phe Leu Pro
65                  70                  75                  80

Val Tyr Phe Gly Ser Val Phe Ile Tyr Ser Lys Gly Lys Asn Met Val
                85                  90                  95

Glu Leu Gly Ser Gly Trp Ser Phe Gln Ile Pro Asp Asp Met Arg Ser
            100                 105                 110

Ala Cys Asn Lys Val Leu Asp Ser Asp Asn Gly Ile Asp Phe Leu Arg
        115                 120                 125

Phe Val Leu Leu Asn His Arg Trp Ile Met Glu Asp Ala Ile Ser Lys
    130                 135                 140

Tyr Gln Ser Pro Val Asn Ile Phe Lys Leu Ala Ser Glu Tyr Gly Leu
145                 150                 155                 160

Asn Ile Pro Lys Tyr Leu Glu Ile Glu Ile Glu Glu Asp Thr Leu Phe
                165                 170                 175

Asp Asp Glu Leu Tyr Ser Ile Ile Glu Arg Ser Phe Asp Lys Phe
            180                 185                 190

Pro Lys Ile Ser Ile Ser Tyr Ile Lys Leu Gly Glu Leu Arg Arg Gln
        195                 200                 205

Val Val Asp Phe Phe Lys Phe Ser Phe Met Tyr Ile Glu Ser Ile Lys
    210                 215                 220

Val Asp Arg Ile Gly Asp Asn Ile Phe Ile Pro Ser Val Ile Thr Lys
225                 230                 235                 240

Ser Gly Lys Lys Ile Leu Val Lys Asp Val Asp His Leu Ile Arg Ser
                245                 250                 255

Lys Val Arg Glu His Thr Phe Lys Val Lys Lys Asn Thr Phe
            260                 265                 270

Ser Ile Leu Tyr Asp Tyr Asp Gly Asn Gly Thr Glu Thr Arg Gly Glu
        275                 280                 285

Val Ile Lys Arg Ile Ile Asp Thr Ile Gly Arg Asp Tyr Tyr Val Asn
    290                 295                 300
```

```
Gly Lys Tyr Phe Ser Lys Val Gly Ser Ala Gly Leu Lys Gln Leu Thr
305                 310                 315                 320

Asn Lys Leu Asp Ile Asn Glu Cys Ala Thr Val Asp Glu Leu Val Asp
            325                 330                 335

Glu Ile Asn Lys Ser Gly Thr Val Lys Arg Lys Ile Lys Asn Gln Ser
        340                 345                 350

Ala Phe Asp Leu Ser Arg Glu Cys Leu Gly Tyr Pro Glu Ala Asp Phe
    355                 360                 365

Ile Thr Leu Val Asn Asn Met Arg Phe Lys Ile Glu Asn Cys Lys Val
370                 375                 380

Val Asn Phe Asn Ile Glu Asn Thr Asn Cys Leu Asn Asn Pro Ser Ile
385                 390                 395                 400

Glu Thr Ile Tyr Gly Asn Phe Asn Gln Phe Val Ser Ile Phe Asn Ile
            405                 410                 415

Val Thr Asp Val Lys Lys Arg Leu Phe Glu
            420                 425

<210> SEQ ID NO 13
<211> LENGTH: 426
<212> TYPE: PRT
<213> ORGANISM: Variola virus

<400> SEQUENCE: 13

Met Thr Ser Ser Ala Asp Leu Thr Asn Leu Lys Glu Leu Leu Ser Leu
1               5                   10                  15

Tyr Lys Ser Leu Arg Phe Ser Asp Ser Ala Ala Ile Glu Lys Tyr Asn
            20                  25                  30

Ser Leu Val Glu Trp Gly Thr Ser Thr Tyr Trp Lys Ile Gly Val Gln
        35                  40                  45

Lys Val Ala His Val Glu Thr Ser Ile Ser Asp Tyr Tyr Asp Glu Val
    50                  55                  60

Lys Asx Lys Pro Phe Asn Ile Asp Pro Gly Tyr Tyr Ile Phe Leu Pro
65                  70                  75                  80

Val Tyr Phe Gly Ser Val Phe Ile Tyr Ser Lys Gly Lys Asn Met Val
                85                  90                  95

Glu Leu Gly Ser Gly Asn Ser Phe Gln Ile Pro Asp Asp Met Gln Ser
            100                 105                 110

Val Cys Asn Lys Val Leu Asp Gly Asp Asn Gly Ile Asp Phe Leu Arg
        115                 120                 125

Phe Val Leu Leu Asn Asn Arg Trp Ile Met Glu Asp Ala Ile Ser Lys
    130                 135                 140

Tyr Gln Ser Pro Val Asn Ile Phe Lys Leu Ala Ser Glu Tyr Gly Leu
145                 150                 155                 160

Asn Ile Pro Asn Tyr Leu Glu Ile Glu Ile Glu Asp Thr Leu Phe
                165                 170                 175

Asp Asp Glu Leu Tyr Ser Ile Ile Glu Arg Ser Phe Asp Asn Phe
            180                 185                 190

Pro Lys Ile Ser Ile Ser Tyr Ile Lys Leu Gly Glu Leu Arg Arg Gln
        195                 200                 205

Val Val Asp Phe Phe Lys Phe Ser Phe Met Tyr Ile Glu Ser Ile Lys
    210                 215                 220

Val Asp Arg Ile Gly Asp Asn Ile Phe Ile Pro Ser Val Ile Thr Lys
225                 230                 235                 240

Ser Gly Lys Lys Ile Leu Val Lys Asp Val Asp His Leu Ile Arg Ser
```

-continued

```
            245                 250                 255
Lys Val Arg Glu His Thr Phe Val Lys Val Lys Lys Asn Thr Phe
            260                 265                 270

Ser Ile Leu Tyr Asp Tyr Asp Gly Asn Gly Thr Glu Thr Arg Gly Glu
            275                 280                 285

Val Ile Lys Arg Ile Ile Asp Thr Ile Gly Arg Asp Tyr Tyr Val Asn
            290                 295                 300

Gly Lys Tyr Phe Ser Lys Val Gly Ser Ala Gly Leu Lys Gln Leu Thr
305                 310                 315                 320

Asn Lys Leu Asn Ile Asn Glu Cys Thr Thr Val Asp Glu Leu Val Asp
                    325                 330                 335

Glu Ile Asn Lys Ser Gly Thr Val Lys Arg Lys Ile Lys Thr Gln Ser
                340                 345                 350

Ala Phe Asp Leu Ser Arg Glu Cys Leu Gly Tyr Pro Glu Ala Asp Phe
                355                 360                 365

Ile Thr Leu Val Asn Asn Met Arg Phe Lys Ile Glu Asn Cys Lys Val
            370                 375                 380

Val Asn Phe Asn Ile Glu Asn Thr Asn Cys Leu Asn Asn Pro Ser Ile
385                 390                 395                 400

Glu Thr Ile Tyr Gly Asn Phe Asn Gln Phe Val Ser Ile Phe Asn Ile
                    405                 410                 415

Val Thr Asp Val Lys Lys Arg Leu Phe Glu
            420                 425

<210

```
Pro Lys Ile Ser Ile Ser Tyr Ile Lys Leu Gly Glu Leu Lys Arg Gln
        195                 200                 205

Val Val Asp Phe Phe Lys Phe Leu Phe Met Tyr Ile Glu Ser Ile Lys
    210                 215                 220

Val Asp Arg Ile Gly Asp Asn Ile Phe Ile Pro Ser Val Ile Thr Lys
225                 230                 235                 240

Ser Gly Lys Lys Ile Leu Val Lys Asp Val Asp His Leu Ile Arg Ser
                245                 250                 255

Lys Val Arg Glu His Thr Phe Val Lys Val Lys Lys Asn Thr Phe
                260                 265                 270

Ser Ile Leu Tyr Asp Tyr Asp Gly Asn Gly Thr Glu Thr Arg Gly Glu
                275                 280                 285

Val Ile Lys Arg Ile Ile Asp Thr Ile Gly Arg Asp Tyr Tyr Val Asn
    290                 295                 300

Gly Lys Tyr Phe Ser Lys Val Gly Ser Ala Gly Leu Lys Gln Leu Thr
305                 310                 315                 320

Asn Lys Leu Asp Ile Asn Glu Cys Ala Thr Val Asp Glu Leu Val Asp
                325                 330                 335

Glu Ile Asn Lys Ser Gly Thr Val Lys Arg Lys Ile Lys Asn Gln Ser
                340                 345                 350

Val Phe Asp Leu Ser Arg Glu Cys Leu Gly Tyr Pro Glu Ala Asp Phe
        355                 360                 365

Ile Thr Leu Val Asn Asn Met Arg Phe Lys Ile Glu Asn Cys Lys Val
        370                 375                 380

Val Asn Phe Asn Ile Glu Asn Thr Asn Cys Leu Asn Asn Pro Ser Ile
385                 390                 395                 400

Glu Thr Ile Tyr Gly Asn Phe Asn Gln Phe Val Ser Ile Phe Asn Thr
                405                 410                 415

Val Thr Asp Val Lys Lys Arg Leu Phe Glu
                420                 425

<210> SEQ ID NO 15
<211> LENGTH: 426
<212> TYPE: PRT
<213> ORGANISM: Cowpox virus

<400> SEQUENCE: 15

Met Thr Ser Ser

-continued

Tyr Gln Ser Pro Val Asn Ile Phe Lys Leu Ala Ser Glu Tyr Gly Leu
145                 150                 155                 160

Asn Ile Pro Lys Tyr Leu Glu Ile Glu Ile Glu Asp Thr Leu Phe
            165                 170                 175

Asp Asp Glu Leu Tyr Ser Ile Ile Glu Arg Ser Phe Asp Lys Phe
            180                 185                 190

Pro Lys Ile Ser Ile Ser Tyr Ile Lys Leu Gly Glu Leu Arg Arg Gln
            195                 200                 205

Val Val Asp Phe Phe Lys Phe Ser Phe Met Tyr Ile Glu Ser Ile Lys
    210                 215                 220

Val Asp Arg Ile Gly Asp Asn Ile Phe Ile Pro Ser Val Ile Thr Lys
225                 230                 235                 240

Ser Gly Lys Lys Ile Leu Val Lys Asp Val Asp His Leu Ile Arg Ser
                245                 250                 255

Lys Val Arg Glu His Thr Phe Val Lys Val Lys Lys Asn Thr Phe
            260                 265                 270

Ser Ile Leu Tyr Asp Tyr Asp Gly Asn Gly Thr Glu Thr Arg Gly Glu
            275                 280                 285

Val Ile Lys Arg Ile Ile Asp Thr Ile Gly Arg Asp Tyr Tyr Val Asn
    290                 295                 300

Gly Lys Tyr Phe Ser Lys Val Gly Ser Ala Gly Leu Lys Gln Leu Thr
305                 310                 315                 320

Asn Lys Leu Asp Ile Asn Glu Cys Thr Thr Val Asp Glu Leu Val Asp
            325                 330                 335

Glu Ile Asn Lys Ser Gly Thr Val Lys Arg Lys Ile Lys Asn Gln Ser
            340                 345                 350

Ala Phe Asp Leu Ser Arg Glu Cys Leu Gly Tyr Pro Glu Ala Asp Phe
            355                 360                 365

Ile Thr Leu Val Asn Asn Met Arg Phe Lys Ile Glu Asn Cys Lys Val
            370                 375                 380

Val Asn Phe Asn Ile Glu Asn Thr Asn Cys Leu Asn Asn Pro Ser Ile
385                 390                 395                 400

Glu Thr Ile Tyr Gly Asn Phe Asn Gln Phe Val Ser Ile Phe Asn Ala
            405                 410                 415

Val Thr Asp Val Lys Lys Arg Leu Phe Glu
            420                 425

<210> SEQ ID NO 16
<211> LENGTH: 470
<212> TYPE: PRT
<213> ORGANISM: Molluscum contagiosum virus

<400> SEQUENCE: 16

Met Ser Lys Glu Pro Asp Leu Thr Lys Leu Lys Glu Leu Leu Arg Leu
1               5                   10                  15

Gln Gln Gln Leu Ala Arg Ala Glu Pro Ala Asp Thr Thr Arg Tyr Asn
                20                  25                  30

Ala Leu Val Asp Trp Ala Arg Arg Thr Tyr Trp His Val Gly Val Arg
            35                  40                  45

Glu Cys Gly Leu Gln Ser Glu Leu Leu Val Glu Pro Phe Glu Gln His
        50                  55                  60

Arg Thr Arg Ala Phe Thr Leu Ala Pro Gly Thr Tyr Thr Phe Ser Ala
65                  70                  75                  80

Leu His Phe Gly Thr Ala Leu Leu Tyr Ala Gly Gly Gln Leu Leu Glu

```
                        85                  90                  95
Leu Gly Ser Gly Ala Ala Arg Gly Ala Pro Glu Glu Leu His Ala Arg
                100                 105                 110

Cys Arg Ala Met Leu Ala Arg Tyr Ala Asp Val Glu Ala Leu Arg Phe
            115                 120                 125

Cys Asn Phe Arg Glu Arg Tyr Val Leu Glu Gln Val His Ala Arg Ala
        130                 135                 140

Arg Pro Ala Pro His Val Trp Leu Pro Leu Ala Ala Glu Gly Leu
145                 150                 155                 160

Ser Val Ala Gln His Thr Arg Val Arg Val Glu Arg Asp Thr Glu Phe
                165                 170                 175

Ser Glu Glu Tyr Phe Gly Val Leu Val Arg Tyr Leu Arg Ala Arg Asp
            180                 185                 190

Ala Ala Leu His Val Glu Ala Val Cys Cys Val Arg Asp Gly Arg Ala
        195                 200                 205

Glu Arg Trp Arg Ile Ala Phe Gly Arg Pro Val Tyr Ser Cys Val Asp
    210                 215                 220

Arg Leu Glu Leu Glu Gln Val Gly Pro Asn Arg Phe Leu Pro Cys Leu
225                 230                 235                 240

Ile Thr Phe Ala Gly Asp Arg Val Leu Ala Arg Asp Leu Glu His Leu
                245                 250                 255

Val Gln Ala His Val Arg Val Gly Ala Phe Ile Val Met Arg Lys Leu
            260                 265                 270

Arg Thr Ala Thr Val Leu Val Ala Ala Glu Ala Ser Thr Glu Thr
        275                 280                 285

Arg Ala Thr Ala Leu Arg Arg Ile Met Gln Ala Leu Gly Gly Glu Tyr
    290                 295                 300

Phe Ala Asn Gly Ala Tyr Val Ser Arg Leu Ala Gln Val Ser Val Glu
305                 310                 315                 320

Gln Leu Ala Asp Arg Met Gly Val Ser Leu Pro Cys Ala Thr Pro Ala
                325                 330                 335

Lys Leu Cys Ala Ala Leu Arg Glu Asp Ala Lys Leu Arg Glu Arg Val
            340                 345                 350

Leu Arg Thr Ser Asp Phe Asp Met Ala Cys Glu Tyr Leu Ser Tyr Gln
        355                 360                 365

Arg Ala Asp Trp Ala Val Ile Asn Ser Met Lys Phe Lys Ile Glu Gln
    370                 375                 380

Arg Lys Ile Val Ser Phe Glu Leu Glu Ser Ala Gly Cys Leu Arg Asp
385                 390                 395                 400

Asp Pro Thr Leu Glu Thr Ile Tyr Ser His Phe Cys Gln Phe Val Ala
                405                 410                 415

Val Phe Asn Phe Leu Ala Glu Val Arg Leu Ala Leu Glu Cys Asp Ala
            420                 425                 430

Ser Gly Val Lys Glu Leu Pro Gly Gly Glu Ala Arg Asn Ala Ala Glu
        435                 440                 445

Ser Ala Val Ala Gly His Gly Pro Asp Ala Glu Pro Arg Glu Glu Thr
    450                 455                 460

Glu Pro Glu Ser Glu Glu
465                 470

<210> SEQ ID NO 17
<211> LENGTH: 218
<212> TYPE: PRT
<213> ORGANISM: Vaccinia virus
```

<400> SEQUENCE: 17

| | | | | | | | | | | | | | | |
|---|---|---|---|---|---|---|---|---|---|---|---|---|---|---|
|Met|Asn|Ser|Val|Thr|Val|Ser|His|Ala|Pro|Tyr|Thr|Ile|Thr|Tyr|His|
|1| | |  |5| | | | |10| | | | |15| |

Asp Asp Trp Glu Pro Val Met Ser Gln Leu Val Glu Phe Tyr Asn Glu
            20                  25                  30

Val Ala Ser Trp Leu Leu Arg Asp Glu Thr Ser Pro Ile Pro Asp Lys
             35                  40                  45

Phe Phe Ile Gln Leu Lys Gln Pro Leu Arg Asn Lys Arg Val Cys Val
 50                      55                      60

Cys Gly Ile Asp Pro Tyr Pro Lys Asp Gly Thr Gly Val Pro Phe Glu
 65                  70                      75                  80

Ser Pro Asn Phe Thr Lys Lys Ser Ile Lys Glu Ile Ala Ser Ser Ile
                 85                      90                  95

Ser Arg Leu Thr Gly Val Ile Asp Tyr Lys Gly Tyr Asn Leu Asn Ile
                100                     105                 110

Ile Asp Gly Val Ile Pro Trp Asn Tyr Tyr Leu Ser Cys Lys Leu Gly
             115                     120                 125

Glu Thr Lys Ser His Ala Ile Tyr Trp Asp Lys Ile Ser Lys Leu Leu
130                     135                     140

Leu Gln His Ile Thr Lys His Val Ser Val Leu Tyr Cys Leu Gly Lys
145                     150                     155                 160

Thr Asp Phe Ser Asn Ile Arg Ala Lys Leu Glu Ser Pro Val Thr Thr
                    165                     170                 175

Ile Val Gly Tyr His Pro Ala Ala Arg Asp Arg Gln Phe Glu Lys Asp
                180                     185                 190

Arg Ser Phe Glu Ile Ile Asn Val Leu Leu Glu Leu Asp Asn Lys Ala
            195                     200                 205

Pro Ile Asn Trp Ala Gln Gly Phe Ile Tyr
            210                 215

<210> SEQ ID NO 18
<211> LENGTH: 218
<212> TYPE: PRT
<213> ORGANISM: Variola virus

<400> SEQUENCE: 18

Met Asn Ser Val Thr Val Ser His Ala Pro Tyr Thr Ile Thr Tyr His
1               5                   10                  15

Asp Asp Trp Glu Pro Val Met Asn Gln Leu Val Glu Phe Tyr Asn Glu
            20                  25                  30

Val Ala Ser Trp Leu Leu Arg Asp Glu Thr Ser Pro Ile Pro Asn Lys
         35                  40                  45

Phe Phe Ile Gln Leu Lys Gln Pro Leu Arg Asn Lys Arg Val Cys Val
 50                      55                      60

Cys Gly Ile Asp Pro Tyr Pro Lys Asp Gly Thr Gly Val Pro Phe Glu
 65                  70                      75                  80

Ser Pro Asn Phe Thr Lys Lys Ser Ile Lys Glu Ile Ala Ser Ser Ile
                 85                      90                  95

Ser Arg Leu Thr Gly Val Ile Asp Tyr Lys Gly Tyr Asn Leu Asn Ile
                100                     105                 110

Ile Asp Gly Val Ile Pro Trp Asn Tyr Tyr Leu Ser Cys Lys Leu Gly
             115                     120                 125

Glu Thr Lys Ser His Ala Ile Tyr Trp Asp Lys Ile Ser Lys Leu Leu
130                     135                     140

Leu His His Ile Thr Lys His Val Ser Val Leu Tyr Cys Leu Gly Lys
145                 150                 155                 160

Thr Asp Phe Ser Asn Ile Arg Ala Lys Leu Glu Ser Pro Val Thr Thr
                165                 170                 175

Ile Val Gly Tyr His Pro Ala Ala Arg Asp Arg Gln Phe Glu Lys Asp
            180                 185                 190

Arg Ser Phe Glu Ile Ile Asn Val Leu Leu Glu Leu Asp Asn Lys Ala
        195                 200                 205

Pro Ile Asn Trp Ala Gln Gly Phe Ile Tyr
    210                 215

<210> SEQ ID NO 19
<211> LENGTH: 218
<212> TYPE: PRT
<213> ORGANISM: Monkeypox virus

<400> SEQUENCE: 19

Met Asn Ser Val Thr Ile Ser His Ala Pro Tyr Thr Ile Thr Tyr His
1               5                   10                  15

Asp Asp Trp Glu Pro Val Met Ser Gln Leu Val Glu Phe Tyr Asn Glu
            20                  25                  30

Val Ala Ser Trp Leu Leu Arg Asp Glu Thr Ser Pro Ile Pro Asp Lys
        35                  40                  45

Phe Phe Ile Gln Leu Lys Gln Pro Leu Arg Asn Lys Arg Val Cys Val
    50                  55                  60

Cys Gly Ile Asp Pro Tyr Pro Lys Asp Gly Thr Gly Val Pro Phe Glu
65                  70                  75                  80

Ser Pro Asn Phe Thr Lys Lys Ser Ile Lys Glu Ile Ala Ser Ser Ile
                85                  90                  95

Ser Arg Leu Thr Gly Val Ile Asp Tyr Lys Gly Tyr Asn Leu Asn Ile
            100                 105                 110

Ile Asp Gly Val Ile Pro Trp Asn Tyr Tyr Leu Ser Cys Lys Leu Gly
        115                 120                 125

Glu Thr Lys Ser His Ala Ile Tyr Trp Asp Lys Ile Ser Lys Leu Leu
130                 135                 140

Leu Gln His Ile Thr Lys His Val Ser Val Leu Tyr Cys Leu Gly Lys
145                 150                 155                 160

Thr Asp Phe Ser Asn Ile Arg Ala Lys Leu Glu Ser Pro Val Thr Thr
                165                 170                 175

Ile Val Gly Tyr His Pro Ala Ala Arg Asp His Gln Phe Glu Lys Asp
            180                 185                 190

Arg Ser Phe Glu Ile Ile Asn Val Leu Leu Glu Leu Asp Asn Lys Thr
        195                 200                 205

Pro Ile Asn Trp Ala Gln Gly Phe Ile Tyr
    210                 215

<210> SEQ ID NO 20
<211> LENGTH: 218
<212> TYPE: PRT
<213> ORGANISM: Cowpox virus

<400> SEQUENCE: 20

Met Asn Ser Val Thr Val Ser His Ala Pro Tyr Thr Ile Thr Tyr His
1               5                   10                  15

Asp Asp Trp Glu Pro Val Met Asn Gln Leu Val Glu Phe Tyr Asn Glu
            20                  25                  30

Val Ala Ser Trp Leu Leu Arg Asp Glu Thr Ser Pro Ile Pro Asp Lys
            35                  40                  45

Phe Phe Ile Gln Leu Lys Gln Pro Leu Arg Asn Lys Arg Val Cys Val
 50                  55                  60

Cys Gly Ile Asp Pro Tyr Pro Lys Asp Gly Thr Gly Val Pro Phe Glu
65                  70                  75                  80

Ser Pro Asn Phe Thr Lys Lys Ser Ile Lys Glu Ile Ala Ser Ser Ile
                85                  90                  95

Ser Arg Leu Thr Gly Val Ile Asp Tyr Lys Gly Tyr Asn Leu Asn Ile
            100                 105                 110

Ile Asp Gly Val Ile Pro Trp Asn Tyr Tyr Leu Ser Cys Lys Leu Gly
            115                 120                 125

Glu Thr Lys Ser His Ala Ile Tyr Trp Asp Lys Ile Ser Lys Leu Leu
            130                 135                 140

Leu Gln His Ile Thr Lys His Val Ser Val Leu Tyr Cys Leu Gly Lys
145                 150                 155                 160

Thr Asp Phe Ser Asn Ile Arg Ala Lys Leu Glu Ser Pro Val Thr Thr
                165                 170                 175

Ile Val Gly Tyr His Pro Ala Ala Arg Asp Arg Gln Phe Glu Lys Asp
            180                 185                 190

Arg Ser Phe Glu Ile Ile Asn Val Leu Leu Glu Leu Asp Asn Lys Ala
            195                 200                 205

Pro Ile Asn Trp Ala Gln Gly Phe Ile Tyr
            210                 215

<210> SEQ ID NO 21
<211> LENGTH: 226
<212> TYPE: PRT
<213> ORGANISM: Molluscum contagiosum virus

<400> SEQUENCE: 21

Met Leu Arg Glu Arg Ala Leu Arg Ala Ala Pro His Val Leu Arg Tyr
1               5                   10                  15

His Glu Asp Trp Glu Pro Val Ala Glu Pro Leu Ala Asp Ala Tyr Ala
            20                  25                  30

Glu Val Ala Pro Trp Leu Leu Arg Asp Arg Thr Glu Pro Ala Pro Glu
            35                  40                  45

Arg Phe Phe Arg Gln Leu Glu Leu Pro Leu Arg Asp Lys Arg Val Cys
 50                  55                  60

Ile Val Gly Ile Asp Pro Tyr Pro Glu Gly Ala Thr Gly Val Pro Phe
65                  70                  75                  80

Glu Ser Pro Asp Phe Ser Lys Lys Thr Ala Arg Ala Leu Ala Ala Ala
                85                  90                  95

Ala Ala Arg Ala Ala Glu His Gly Gly Cys Arg Arg Val Ser Ala Tyr
            100                 105                 110

Arg Asn Tyr Asp Phe Arg Gly Val Gln Gly Val Leu Ala Trp Asn Tyr
            115                 120                 125

Tyr Leu Ser Cys Arg Arg Gly Glu Thr Lys Ser His Ala Met His Trp
130                 135                 140

Glu Arg Ile Ala Arg Met Leu Leu Ala His Ile Ala Arg Phe Val Arg
145                 150                 155                 160

Val Phe Tyr Phe Leu Gly Arg Ser Asp Phe Gly Gly Val Arg Ala Lys
                165                 170                 175

Leu Thr Ala Pro Val Thr Leu Leu Val Gly Tyr His Pro Ala Ala Arg

```
                 180                 185                 190
Gly Gly Gln Phe Glu Ser Glu Arg Thr Leu Glu Ile Leu Asn Val Leu
            195                 200                 205

Leu Glu Leu His Gly Leu Ala Pro Val Asp Trp Ala Gln Gly Phe Val
    210                 215                 220

Pro Leu
225

<210> SEQ ID NO 22
<211> LENGTH: 230
<212> TYPE: PRT
<213> ORGANISM: Human herpesvirus 4

<400> SEQUENCE: 22

Gly Glu Asn Leu Leu Leu Pro Asp Leu Trp Leu Asp Phe Leu Gln Leu
1               5                   10                  15

Ser Pro Ile Phe Gln Arg Lys Leu Ala Ala Val Ile Ala Cys Val Arg
            20                  25                  30

Arg Leu Arg Thr Gln Ala Thr Val Tyr Pro Glu Glu Asp Met Cys Met
        35                  40                  45

Ala Trp Ala Arg Phe Cys Asp Pro Ser Asp Ile Lys Trp Ile Leu Gly
    50                  55                  60

Gln Asp Pro Tyr His Gly Gly Gln Ala Asn Gly Leu Ala Phe Ser Val
65                  70                  75                  80

Ala Tyr Gly Phe Pro Val Pro Pro Ser Leu Arg Asn Ile Tyr Ala Glu
                85                  90                  95

Leu His Arg Ser Leu Pro Glu Phe Ser Pro Pro Asp His Gly Cys Leu
            100                 105                 110

Asp Ala Trp Ala Ser Gln Gly Val Leu Leu Leu Asn Thr Ile Leu Thr
        115                 120                 125

Val Gln Lys Gly Lys Pro Gly Ser His Ala Asp Ile Gly Trp Ala Trp
    130                 135                 140

Phe Thr Asp His Val Ile Ser Leu Leu Ser Glu Arg Leu Lys Ala Cys
145                 150                 155                 160

Val Phe Met Leu Trp Gly Ala Lys Ala Gly Asp Lys Ala Ser Leu Ile
                165                 170                 175

Asn Ser Lys Lys His Leu Val Leu Thr Ser Gln His Pro Ser Pro Leu
            180                 185                 190

Ala Gln Asn Ser Thr Arg Lys Ser Ala Gln Gln Lys Phe Leu Gly Asn
        195                 200                 205

Asn His Phe Val Leu Ala Asn Asn Phe Leu Arg Glu Lys Gly Leu Gly
    210                 215                 220

Glu Ile Asp Trp Arg Leu
225                 230
```

What is claimed is:

1. A compound of formula (I)

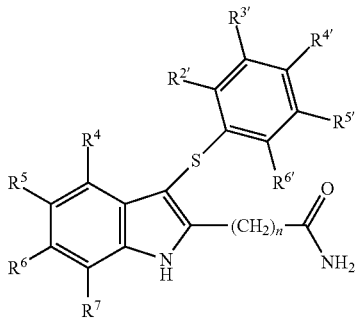

wherein
$R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, and heteroarylalkyl;

$R^m$ and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 3-7 membered heterocycloalkyl group; and n is 1, 2, 3, 4, or 5;

or a pharmaceutically acceptable salt thereof.

2. The compound of claim 1, wherein n is 1, 2, or 3.

3. The compound of any one of claims 1 and 2, wherein $R^4$, $R^5$, $R^6$, $R^7$, $R^{2'}$, $R^{3'}$, $R^{4'}$, $R^{5'}$, and $R^{6'}$ each independently are H, $C_1$-$C_6$ alkyl, or halo.

4. The compound of any one of claims 1 and 2, wherein $R^4$, $R^5$, $R^6$, and $R^7$ each independently are H or $CH_3$.

5. The compound of any one of claims 1 and 2, wherein $R^6$ is $CH_3$.

6. The compound of any one of claims 1 and 2, wherein $R^4$, $R^5$, and $R^7$ are H, and $R^6$ is $CH_3$.

7. The compound of any one of claims 1 and 2, wherein $R^{2'}$, $R^{3'}$, $R^{4'}$, $R^{5'}$, and $R^{6'}$ each independently are H or halo.

8. The compound of any one of claims 1 and 2, wherein $R^{2'}$, $R^{3'}$, $R^{4'}$, $R^{5'}$, and $R^{6'}$ each independently are H or chloro.

9. The compound of any one of claims 1 and 2, wherein $R^{2'}$, $R^{3'}$, $R^{4'}$, $R^{5'}$, and $R^{6'}$ are H.

10. The compound of any one of claims 1 and 2, wherein $R^{3'}$ and $R^{5'}$ are halo.

11. The compound of any one of claims 1 and 2, wherein $R^{3'}$ and $R^{5'}$ are chloro.

12. The compound of any one of claims 1 and 2, wherein $R^{2'}$, $R^{4'}$, and $R^{6'}$ are H, and $R^{3'}$ and $R^{5'}$ are chloro.

13. The compound of claim 1, wherein the compound is
3-(3-((3,5-dichlorophenyl)thio)-6-methyl-1H-indol-2-yl)propanamide;
2-(3-((3,5-dichlorophenyl)thio)-6-methyl-1H-indol-2-yl)acetamide; or
4-(3-((3,5-dichlorophenyl)thio)-6-methyl-1H-indol-2-yl)butanamide.

14. The compound of any one of claims 1 and 2, wherein the compound is
2-(6-methyl-3-(phenylthio)-1H-indol-2-yl)acetamide;
3-(6-methyl-3-(phenylthio)-1H-indol-2-yl)propanamide; or
4-(6-methyl-3-(phenylthio)-1H-indol-2-yl)butanamide.

15. The compound of any one of claims 1 and 2, wherein the compound is
2-(3-((4-chlorophenyl)thio)-6-methyl-1H-indol-2-yl)acetamide;
3-(3-((4-chlorophenyl)thio)-6-methyl-1H-indol-2-yl)propanamide; or
4-(3-((4-chlorophenyl)thio)-6-methyl-1H-indol-2-yl)butanamide.

16. A composition comprising a compound of formula (I) according to any one of claims 1 and 2, or a pharmaceutically acceptable salt thereof, and at least one pharmaceutically acceptable carrier.

17. A method of inhibiting, treating, or abrogating a poxvirus infection in a subject, the method comprising administering to said subject a compound of formula (II),

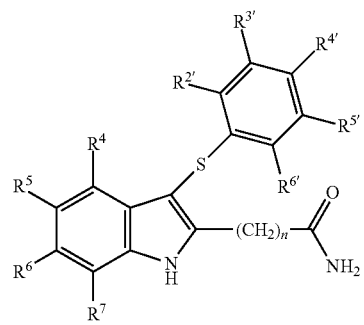

wherein
$R^4$, $R^5$, $R^6$, $R^7$, $R^{2'}$, $R^{3'}$, $R^{4'}$, $R^{5'}$, and $R^{6'}$ are independently selected from the group consisting of H, $C_1$-$C_6$ alkyl, halo, cyano, nitro, $C_1$-$C_6$ haloalkyl, $OR^a$, $SR^a$, $NR^mR^n$, $NR^aCOR^b$, $SOR^b$, $SO_2R^b$, $COR^b$, $COOR^a$, aryl, heteroaryl, $C_3$-$C_7$ cycloalkyl, 3-7 membered heterocycloalkyl, cycloalkylalkyl, heterocycloalkylalkyl, arylalkyl, and heteroarylalkyl;

$R^a$ and $R^b$ are each independently selected from the group consisting of H, $C_{1-6}$ alkyl, $C_{1-6}$ haloalkyl, $C_2$-$C_6$ alkenyl, $C_2$-$C_6$ alkynyl, cycloalkyl, heterocycloalkyl, aryl, heteroaryl, cycloalkylalkyl, heterocycloalkylalkyl, arylalkyl, heteroarylalkyl;

$R^m$ and $R^n$ are independently selected from the group consisting of H, $C_1$-$C_6$ alkyl, cycloalkyl, cycloalkylalkyl, heterocycloalkylalkyl, arylalkyl, and heteroarylalkyl; or $R^m$ and $R^n$, together with the nitrogen atom to which they are attached, form a 4-7 membered heterocycloalkyl group; and n is 0, 1, 2, 3, 4, or 5;

or a composition thereof, or a pharmaceutically acceptable salt thereof, wherein said compound reduces, inhibits, or abrogates activity of a DNA polymerase of said poxvirus.

18. The method of claim 17, wherein n is 1, 2, or 3.

19. The method of any one of claims 17 and 18, wherein $R^4$, $R^5$, $R^6$, $R^7$, $R^{2'}$, $R^{3'}$, $R^{4'}$, $R^{5'}$, and $R^{6'}$ each independently are H, $C_1$-$C_6$ alkyl, or halo.

20. The method of any one of claims 17 and 18, wherein $R^4$, $R^5$, $R^6$, and $R^7$ each independently are H or $CH_3$.

21. The method of any one of claims 17 and 18, wherein $R^4$, $R^5$, and $R^7$ are H, and $R^6$ is $CH_3$.

22. The method of any one of claims 17 and 18, wherein $R^{2'}$, $R^{3'}$, $R^{4'}$, $R^{5'}$, and $R^{6'}$ each independently are H or halo.

23. The method of any one of claims 17 and 18, wherein $R^{2'}$, $R^{3'}$, $R^{4'}$, $R^{5'}$, and $R^{6'}$ are H.

24. The method of any one of claims 17 and 18, wherein $R^{2'}$, $R^{4'}$, and $R^{6'}$ are H, and $R^{3'}$ and $R^{5'}$ are chloro.

25. The method of any one of claims 17 and 18, wherein the compound is
- 3-(3-((3,5-dichlorophenyl)thio)-6-methyl-1H-indol-2-yl)propanamide;
- 2-(3-((3,5-dichlorophenyl)thio)-6-methyl-1H-indol-2-yl)acetamide; or
- 4-(3-((3,5-dichlorophenyl)thio)-6-methyl-1H-indol-2-yl)butanamide.

26. The method of any one of claims 17 and 18, wherein the compound is
- 2-(6-methyl-3-(phenylthio)-1H-indol-2-yl)acetamide;
- 3-(6-methyl-3-(phenylthio)-1H-indol-2-yl)propanamide; or
- 4-(6-methyl-3-(phenylthio)-1H-indol-2-yl)butanamide.

27. The method of any one of claims 17 and 18, wherein the compound is
- 2-(3-((4-chlorophenyl)thio)-6-methyl-1H-indol-2-yl)acetamide;
- 3-(3-((4-chlorophenyl)thio)-6-methyl-1H-indol-2-yl)propanamide; or
- 4-(3-((4-chlorophenyl)thio)-6-methyl-1H-indol-2-yl)butanamide.

28. The method of any one of claims 17 and 18, wherein said poxvirus is a vaccinia virus.

29. The method of any one of claims 17 and 18, wherein said poxvirus is a variola.

30. The method of any one of claims 17 and 18, wherein said poxvirus is a molluscum contagiosum virus.

31. The method of any one of claims 17 and 18, wherein said inhibiting a poxvirus infection in a subject comprises the step of inhibiting DNA synthesis of said poxvirus.

32. The method of any one of claims 17 and 18, wherein said DNA polymerase is an E9 DNA polymerase or a homologue thereof from a different species.

33. The method of any one of claims 17 and 18, wherein said compound reduces, inhibits, or abrogates interaction of said DNA polymerase with a processivity factor.

34. The method of claim 33, wherein said processivity factor is an A20 or D4R processivity factor or a homologue thereof from a different species.

35. The method of any one of claims 17 and 18, wherein said subject is a human.

* * * * *